United States Patent [19]
Kudo et al.

[11] Patent Number: 5,836,869
[45] Date of Patent: Nov. 17, 1998

[54] IMAGE TRACKING ENDOSCOPE SYSTEM

[75] Inventors: Masahiro Kudo, Hino; Kuniaki Kami, Machida; Hiroki Hibino, Hachioji; Hitoshi Mizuno, Koganei; Akihiro Horii, Akishima; Susumu Takahashi, Iruma; Noriyuki Tateyama, Hachioji, all of Japan

[73] Assignee: Olympus Optical Co., Ltd., Tokyo, Japan

[21] Appl. No.: 551,713

[22] Filed: Nov. 1, 1995

[30] Foreign Application Priority Data

| Dec. 13, 1994 | [JP] | Japan | 6-308740 |
| May 15, 1995 | [JP] | Japan | 7-115995 |
| Jun. 8, 1995 | [JP] | Japan | 7-142133 |
| Aug. 23, 1995 | [JP] | Japan | 7-214824 |

[51] Int. Cl.$^6$ ............................................ A61B 1/04
[52] U.S. Cl. ........................ 600/173; 600/118; 600/102; 600/168
[58] Field of Search ................... 600/102, 109, 600/112, 117, 118, 173, 168; 128/653.1; 348/65, 73, 76

[56] References Cited

U.S. PATENT DOCUMENTS

| 4,588,294 | 5/1986 | Siegmund | 600/117 X |
| 4,601,284 | 7/1986 | Arakawa et al. | 600/113 |
| 5,049,988 | 9/1991 | Sefton et al. | 358/93 |
| 5,279,309 | 1/1994 | Taylor . | |
| 5,313,306 | 5/1994 | Kuban et al. | 348/65 |
| 5,402,801 | 4/1995 | Taylor . | |
| 5,506,912 | 4/1996 | Nagasaki et al. | 600/103 X |
| 5,547,455 | 8/1996 | McKenna et al. | 600/113 |
| 5,572,999 | 11/1996 | Funda et al. | 128/653.1 |

FOREIGN PATENT DOCUMENTS

| 54-31390 | 5/1954 | Japan . |
| 1-280438 | 11/1989 | Japan . |
| 1-172015 | 12/1989 | Japan . |
| 2-103023 | 4/1990 | Japan . |
| 4-102437 | 4/1992 | Japan . |
| 5-337117 | 12/1993 | Japan . |
| 5-337118 | 12/1993 | Japan . |
| WO 94/03113 | 2/1994 | WIPO . |

*Primary Examiner*—John P. Leubecker
*Attorney, Agent, or Firm*—Frishauf, Holtz, Goodman, Langer & Chick

[57] ABSTRACT

An endoscope system having an endoscope, a scope holder holding the endoscope, a magnetic three-dimensional position sensor, and a TV monitor. The sensor detects the position of an object and generates data representing this position. According to the data, the view field of the endoscope is switched.

7 Claims, 56 Drawing Sheets

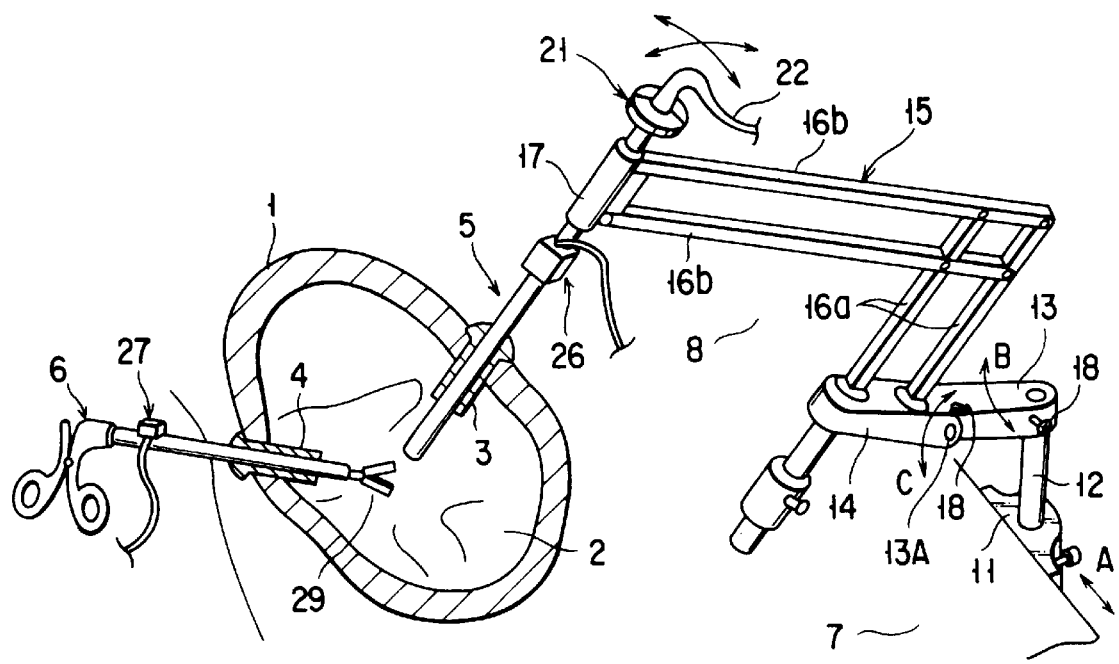
F I G. 1
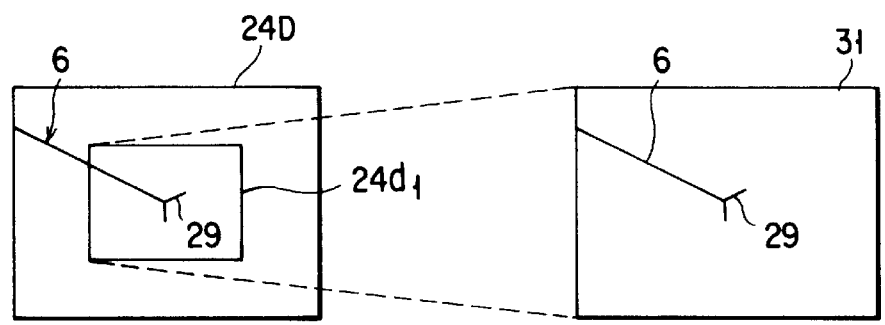
F I G. 2A
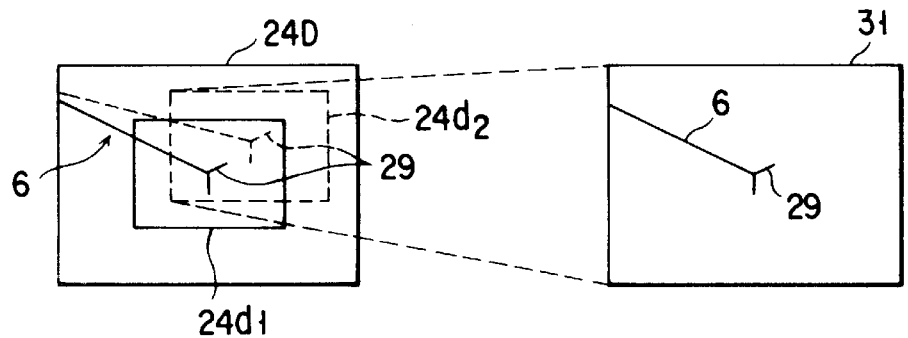
F I G. 2B

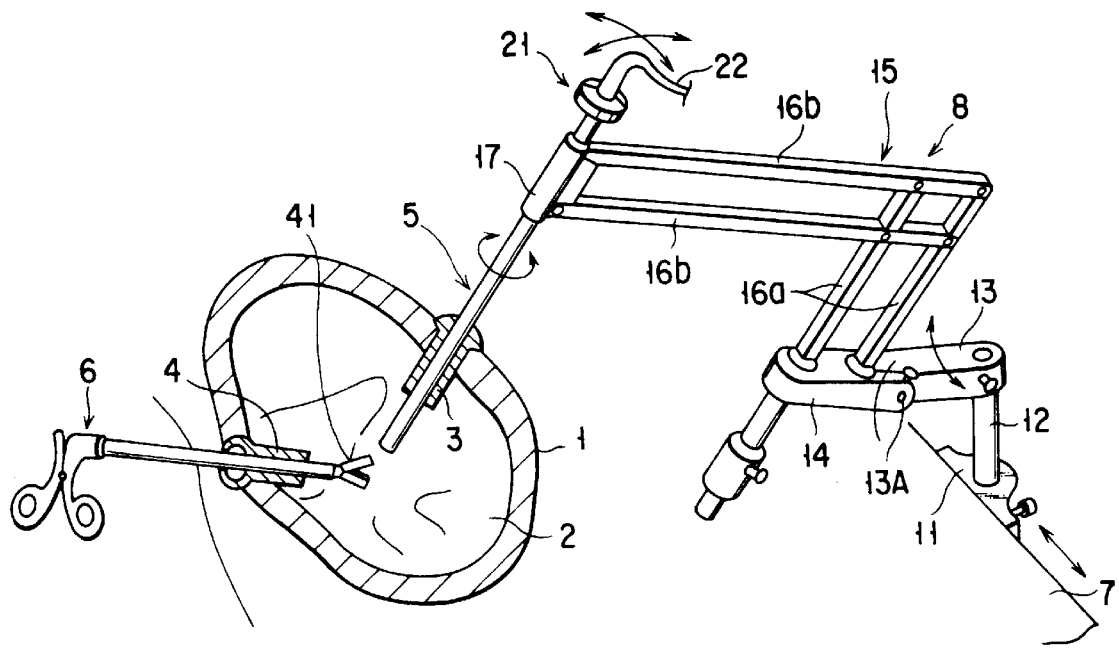
F I G. 4
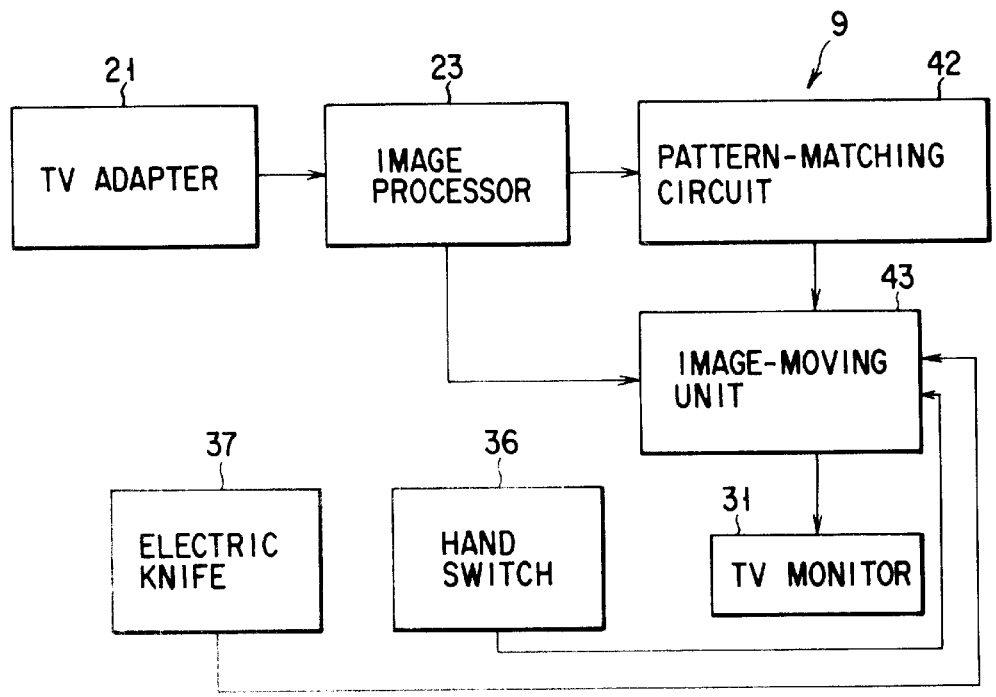
F I G. 5

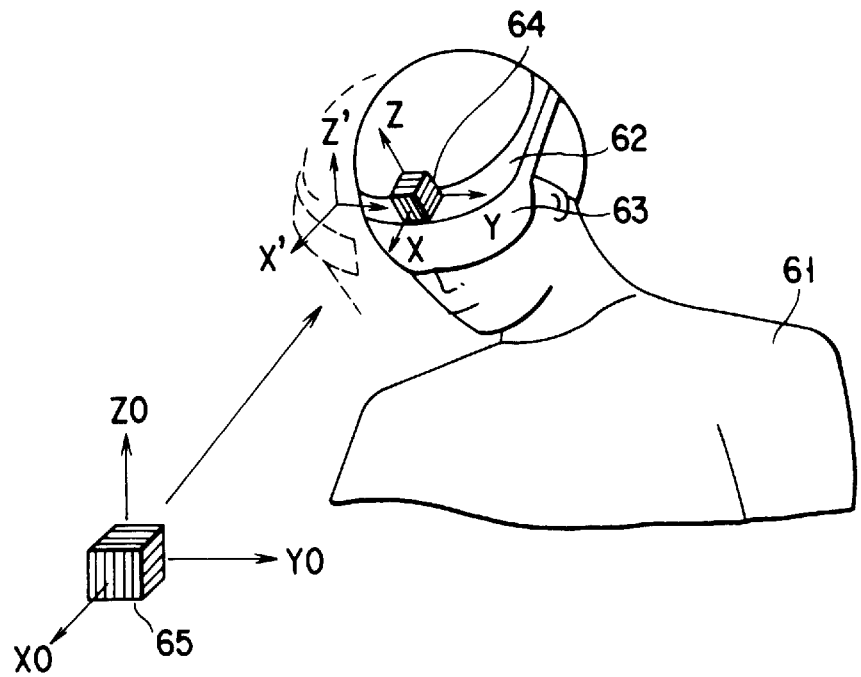
FIG. 7A
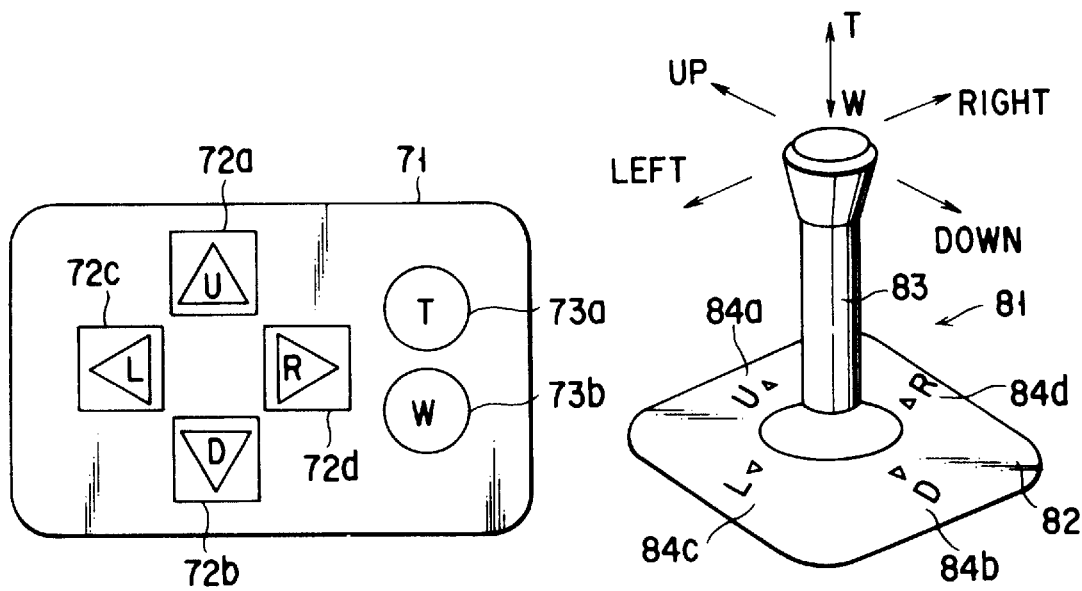
FIG. 7B
FIG. 7C

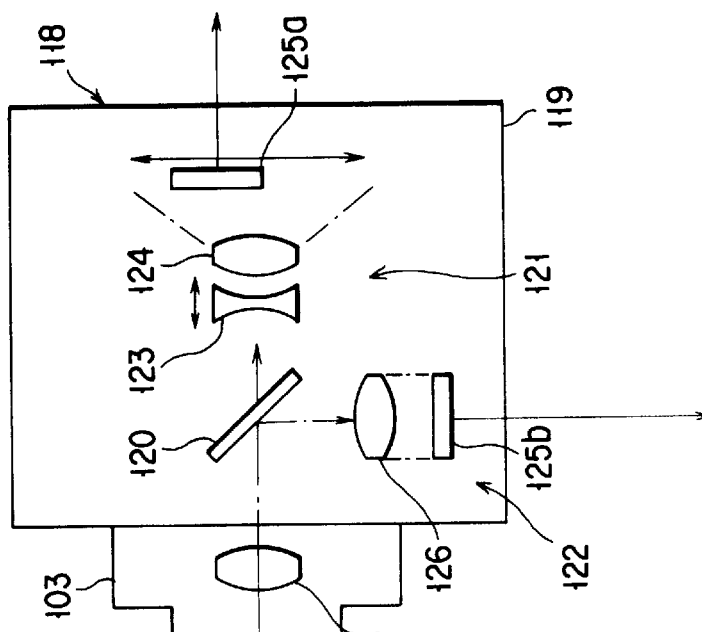
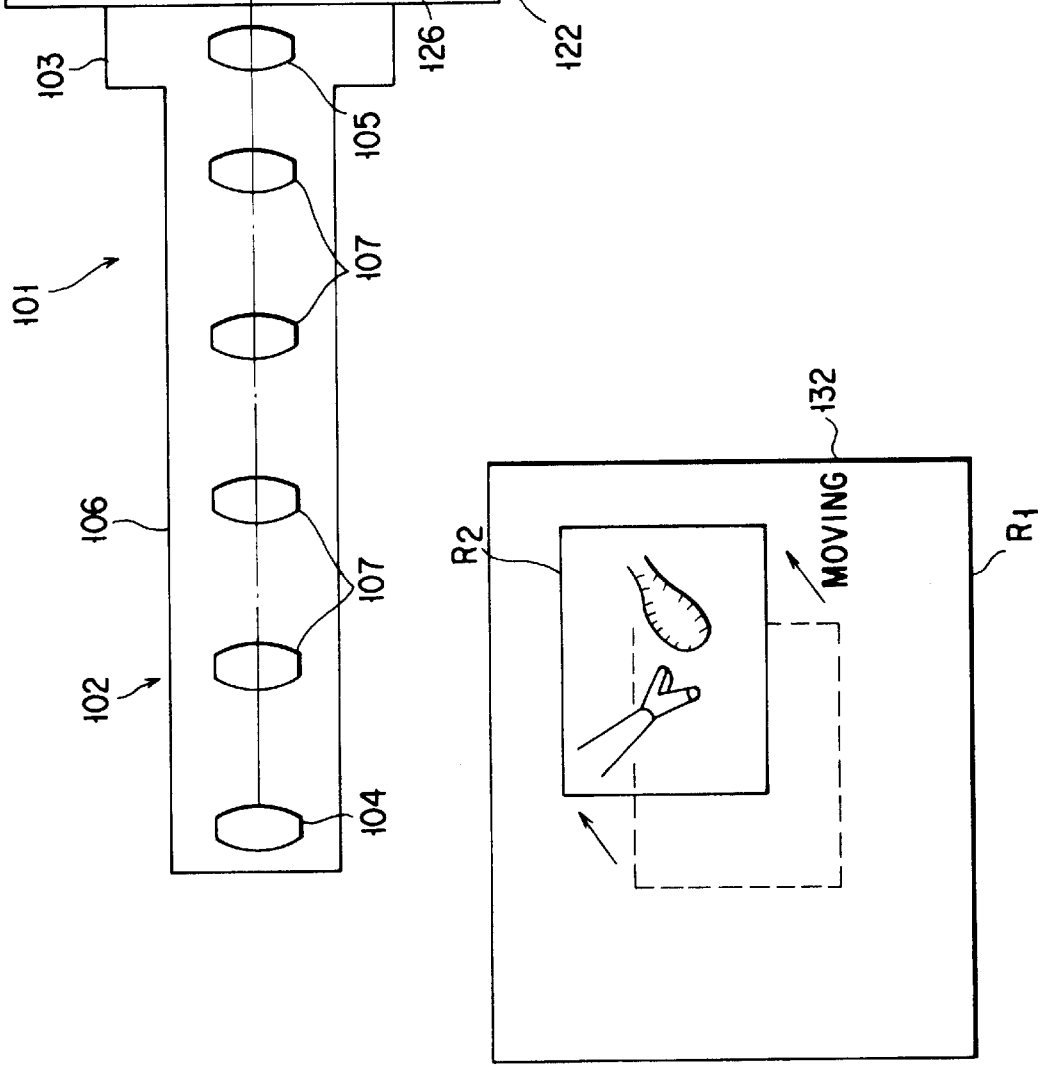
FIG. 10A
FIG. 10B

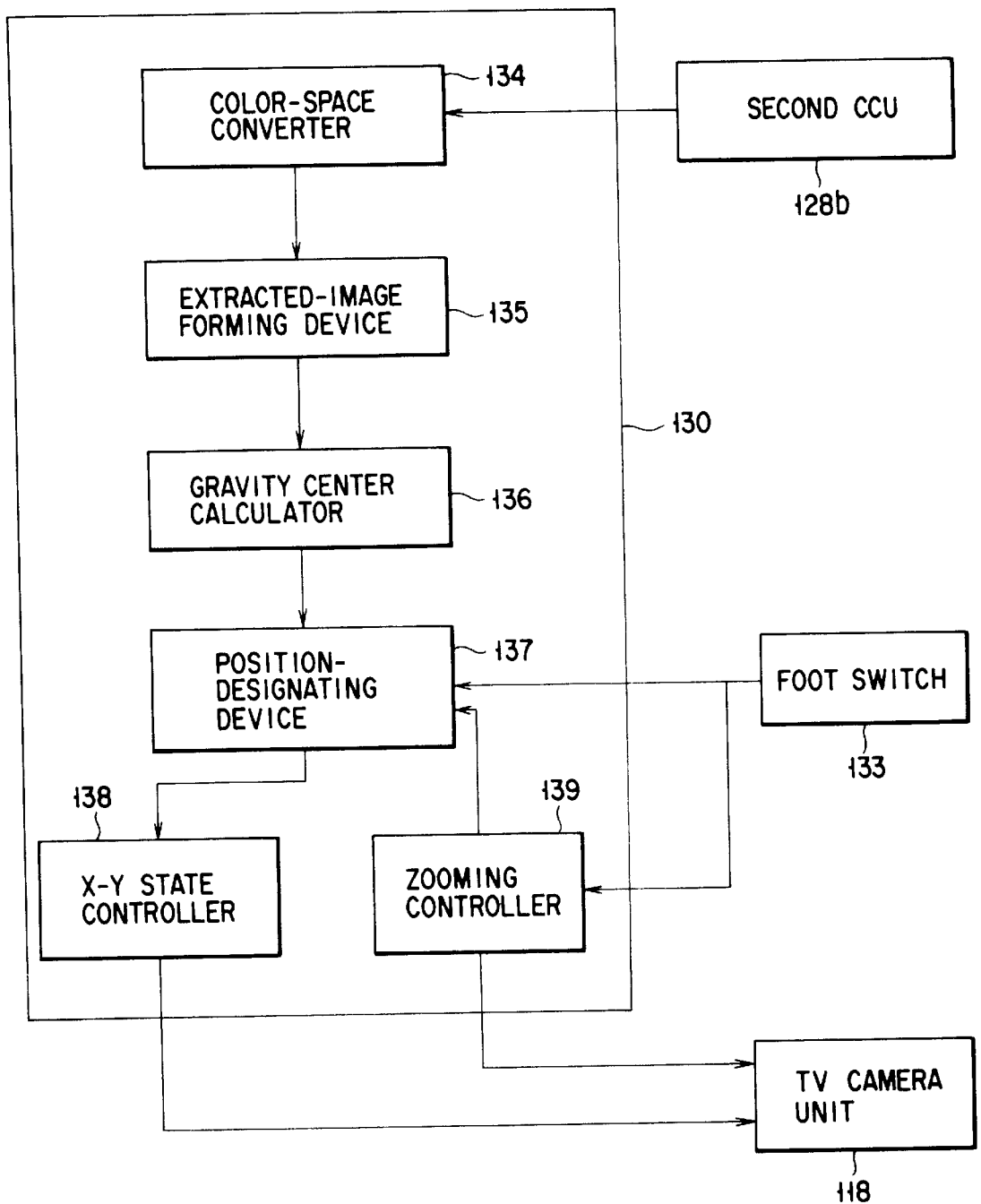
F I G. 11

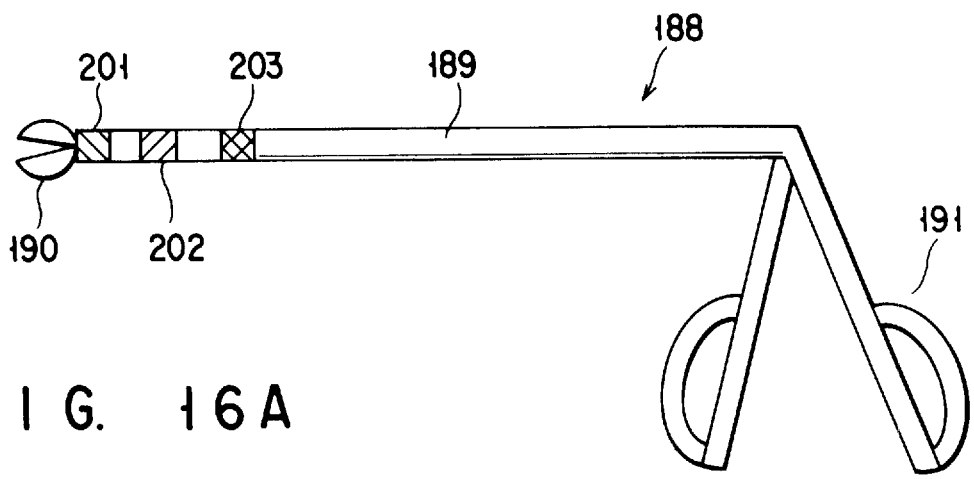
F I G. 16A
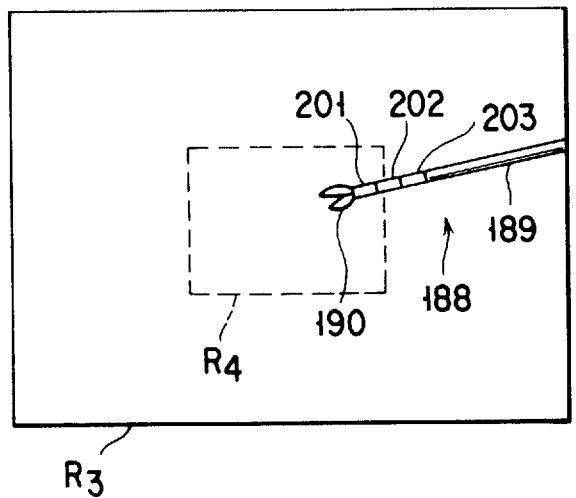
F I G. 16B
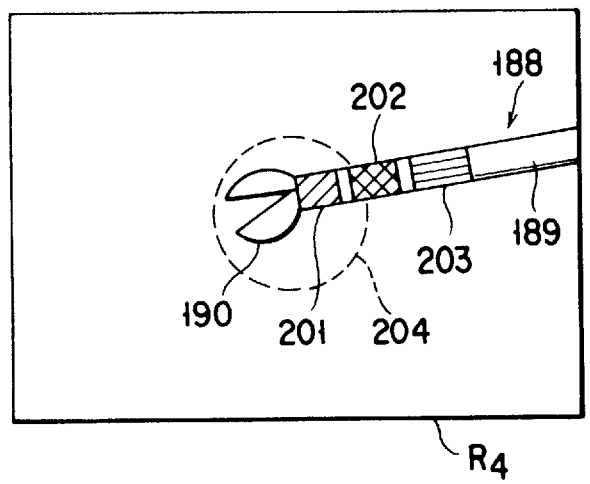
F I G. 16C

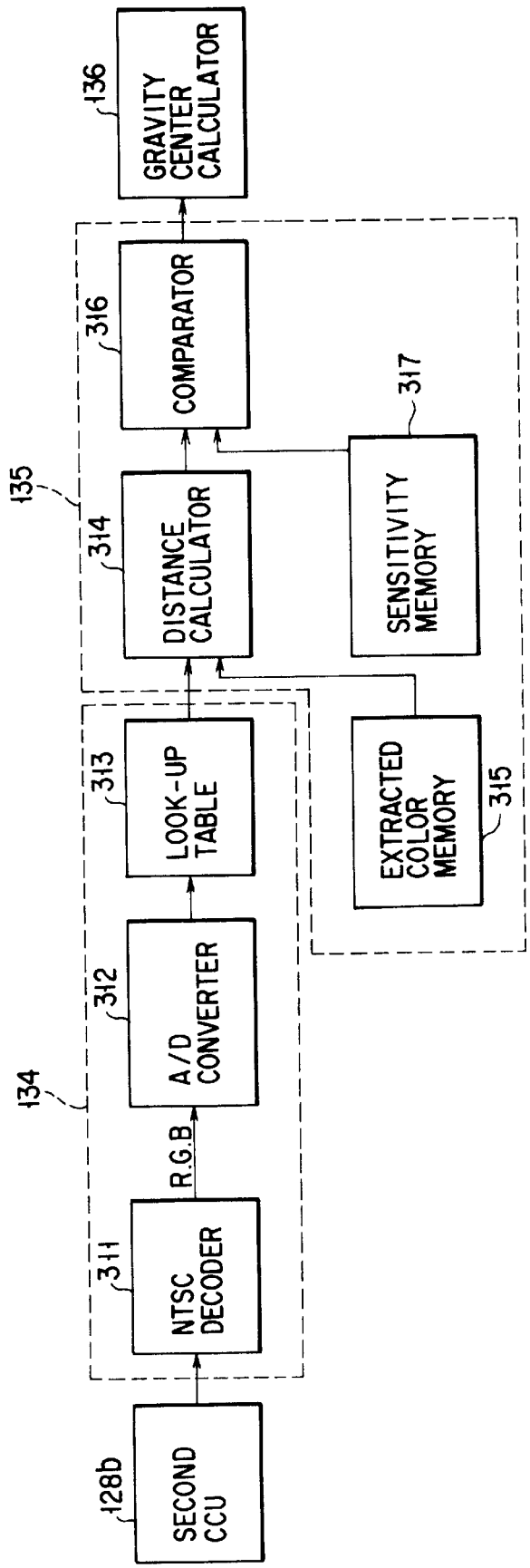
F I G. 26

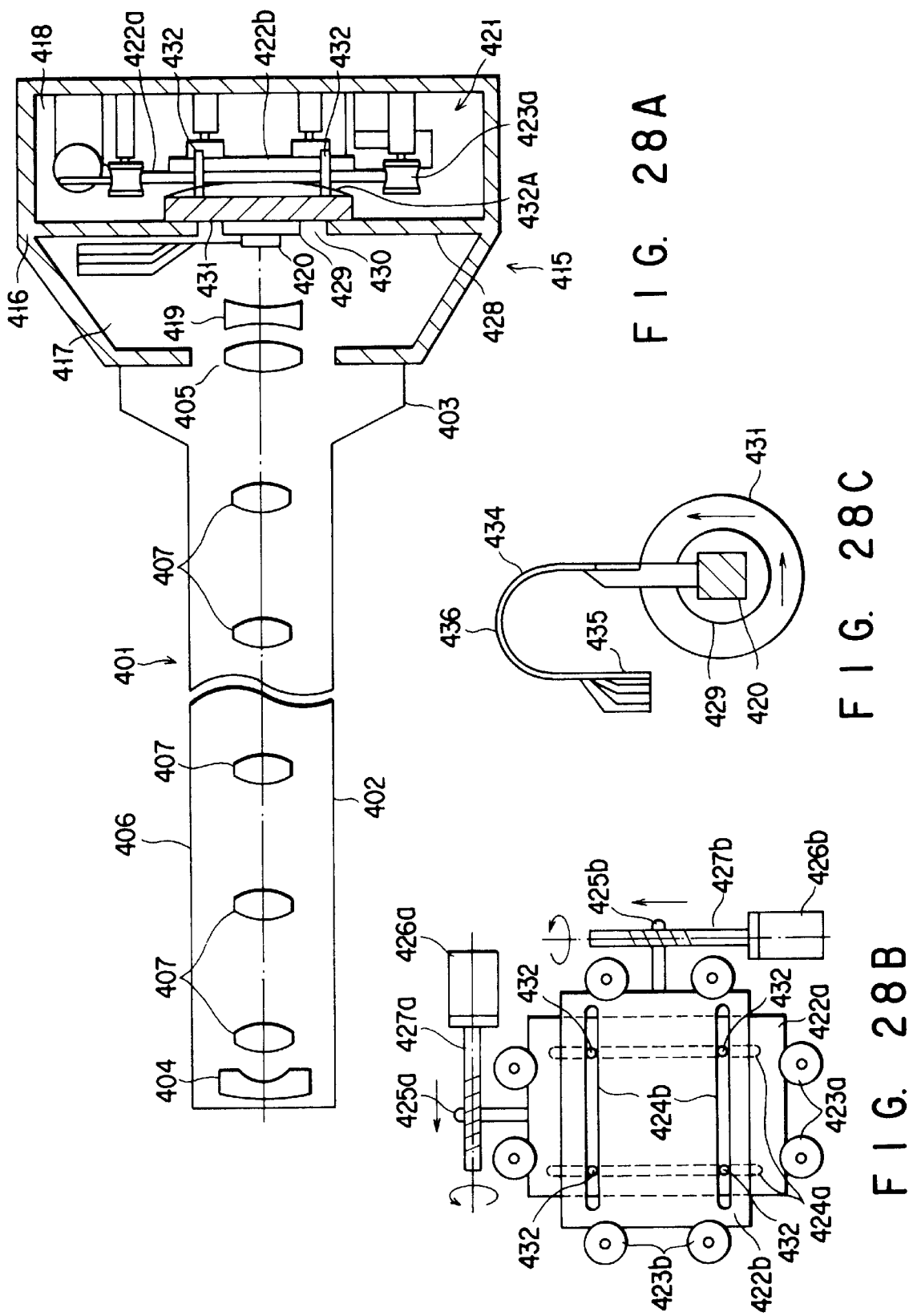

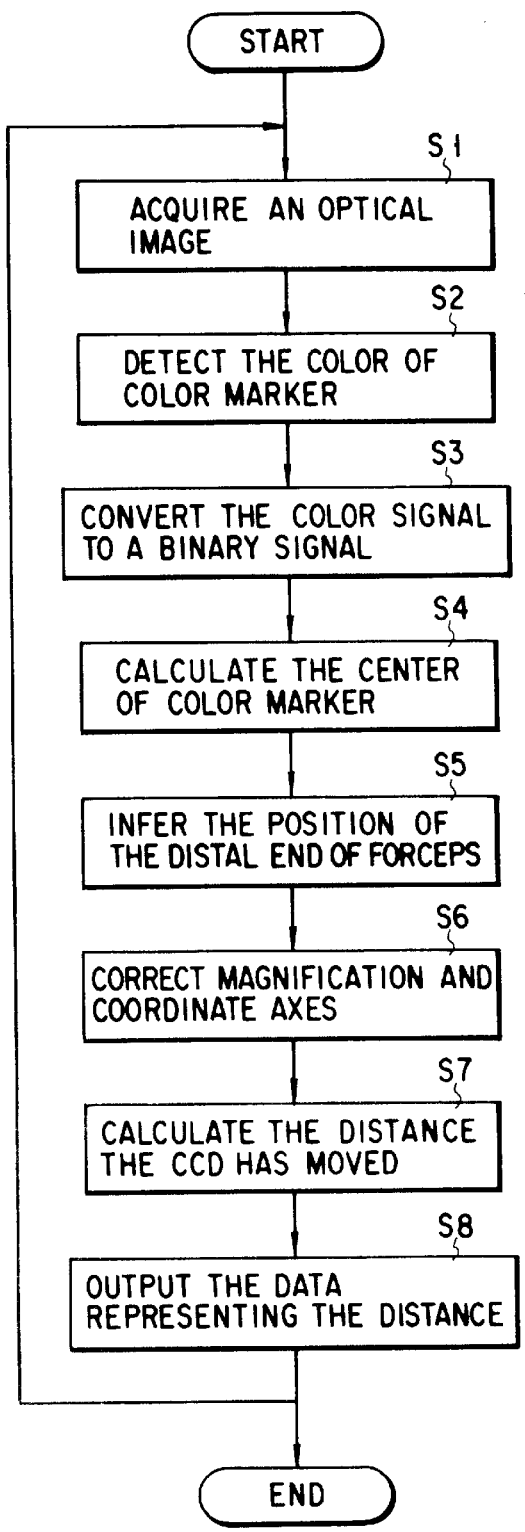
F I G. 30
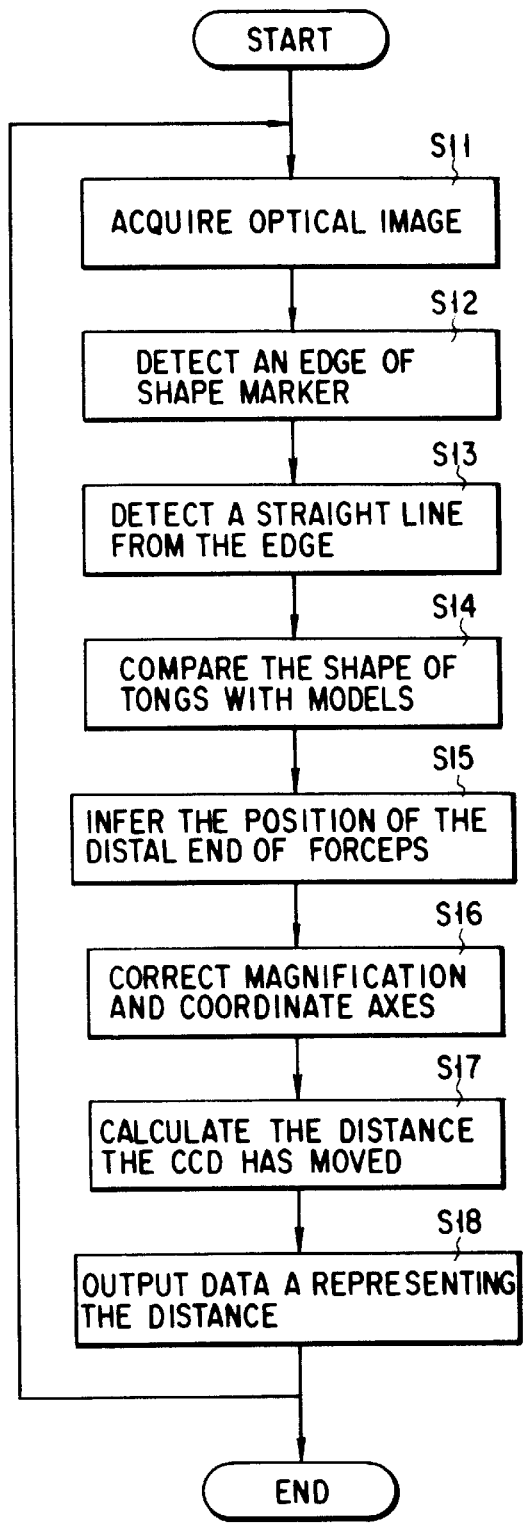
F I G. 31

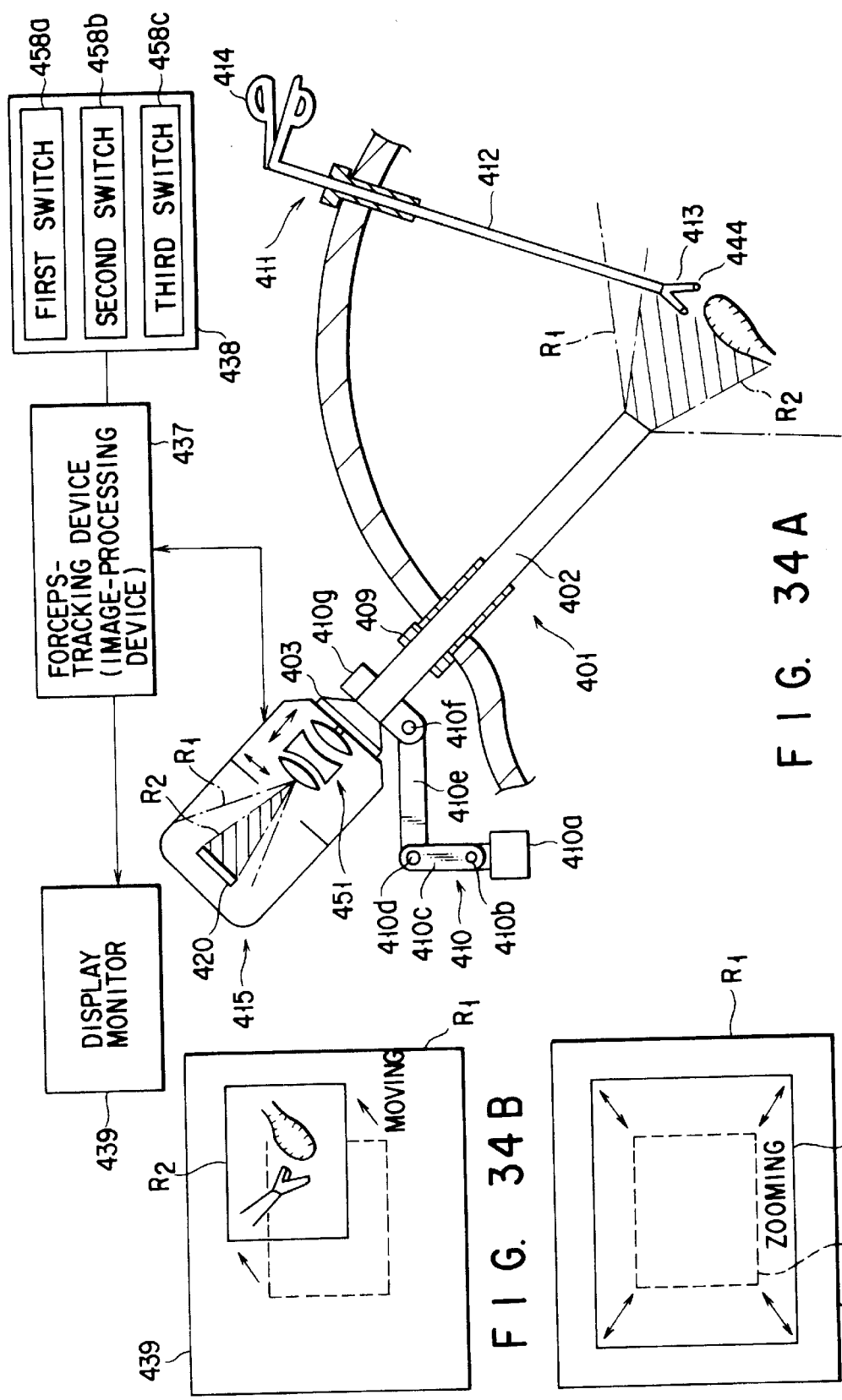

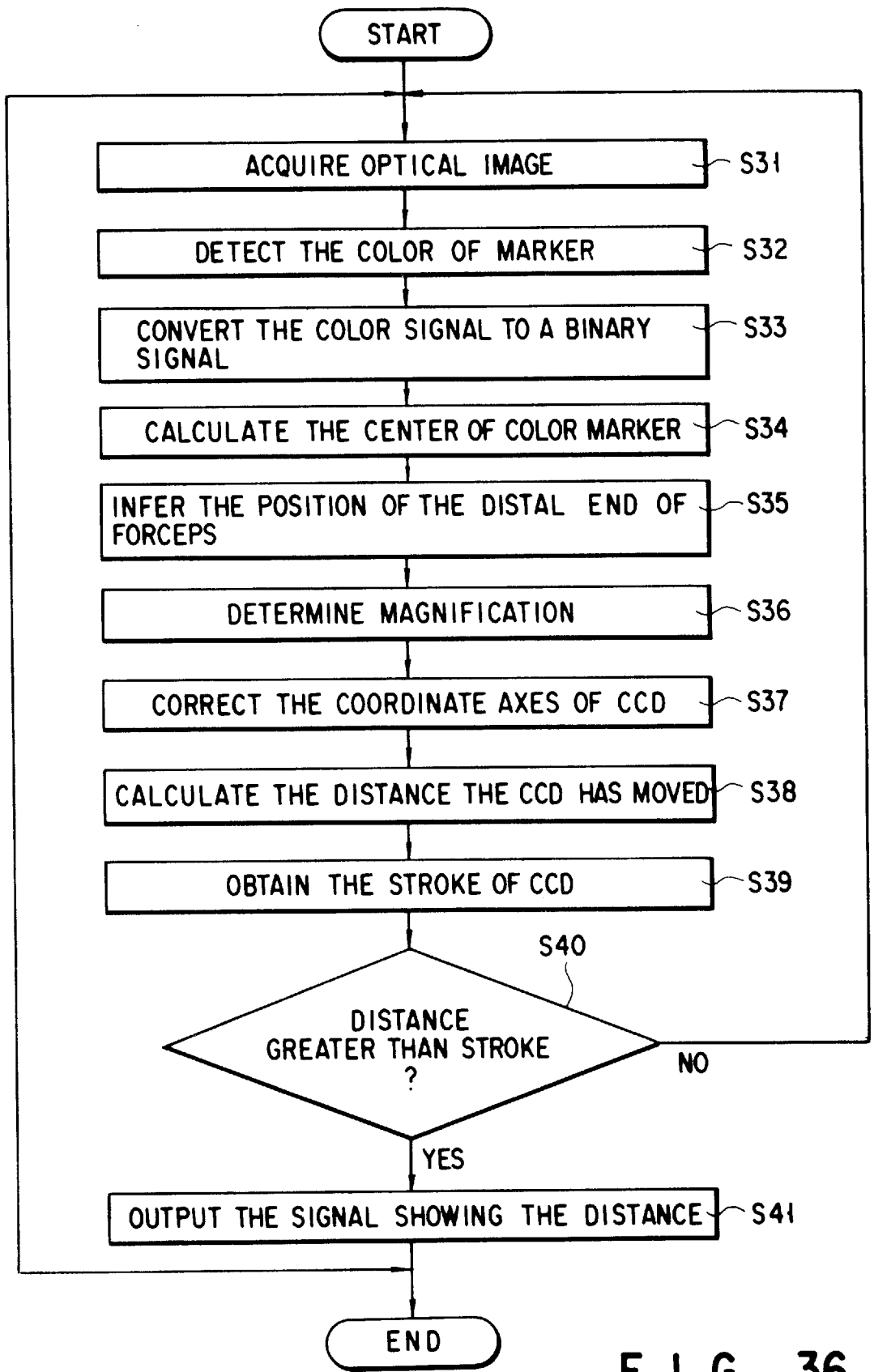
F I G. 36

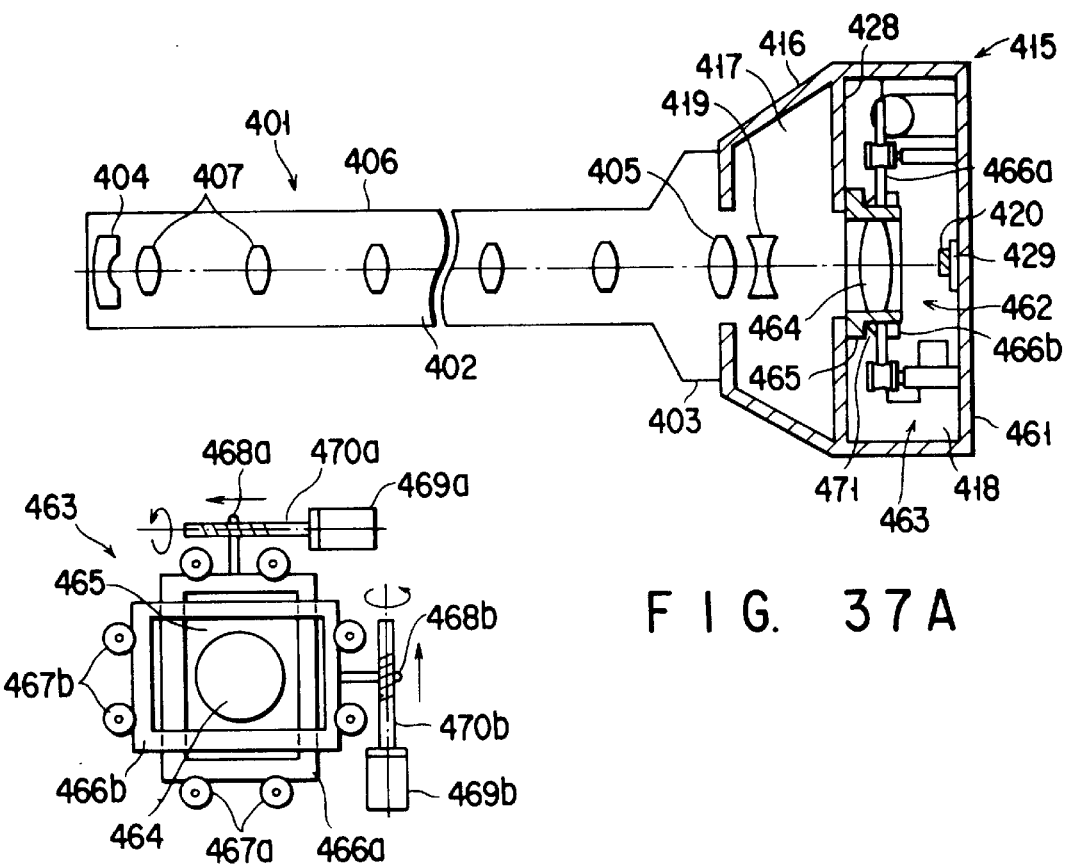
FIG. 37A
FIG. 37B
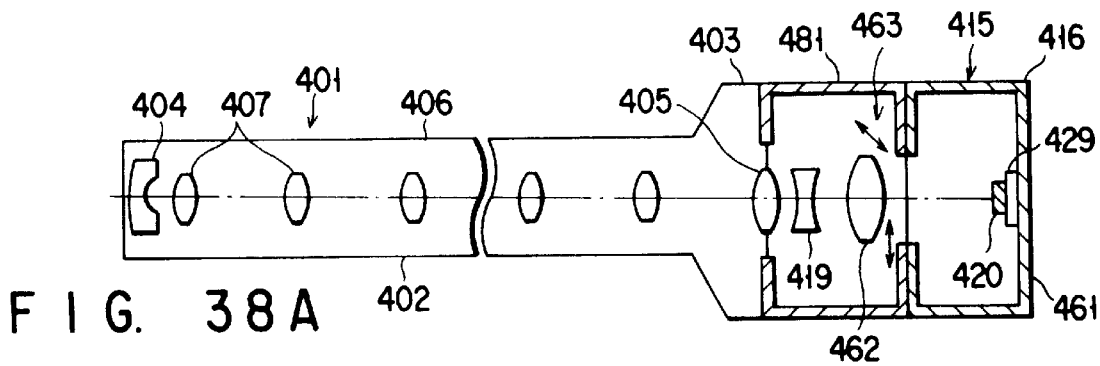
FIG. 38A
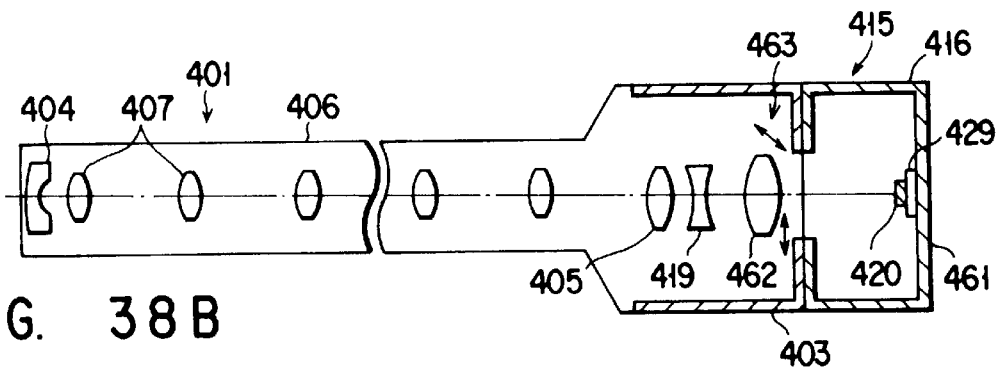
FIG. 38B

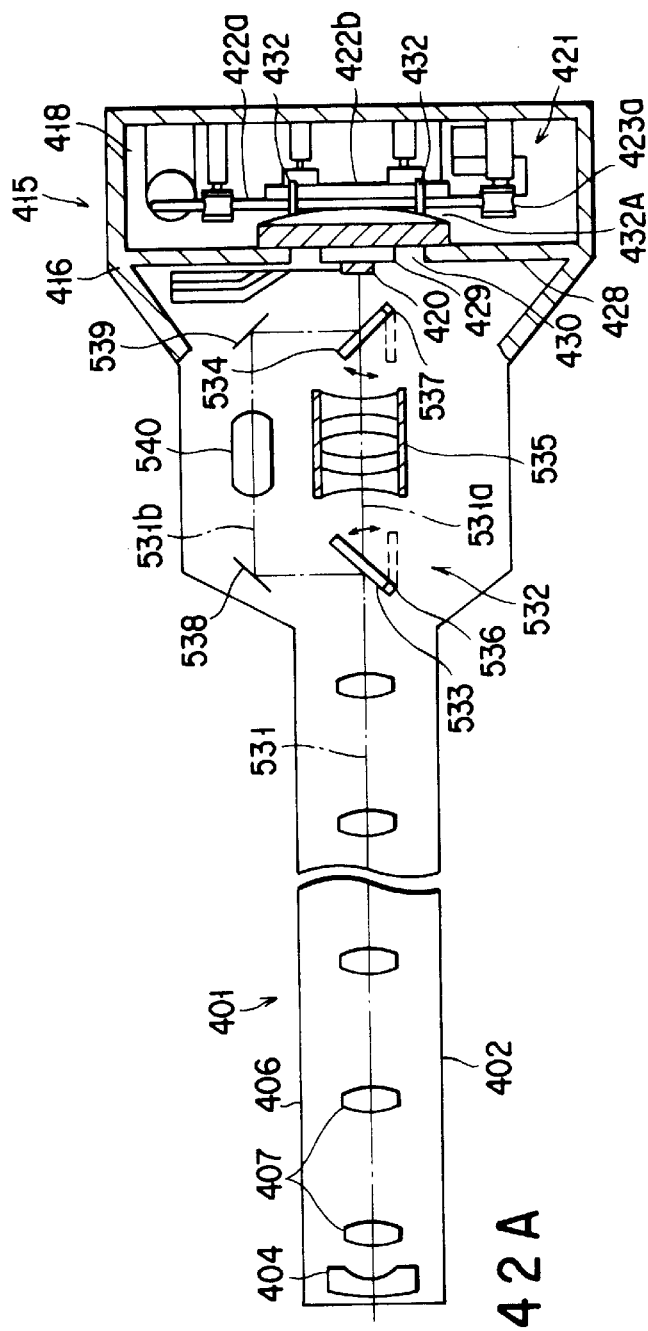
FIG. 42A
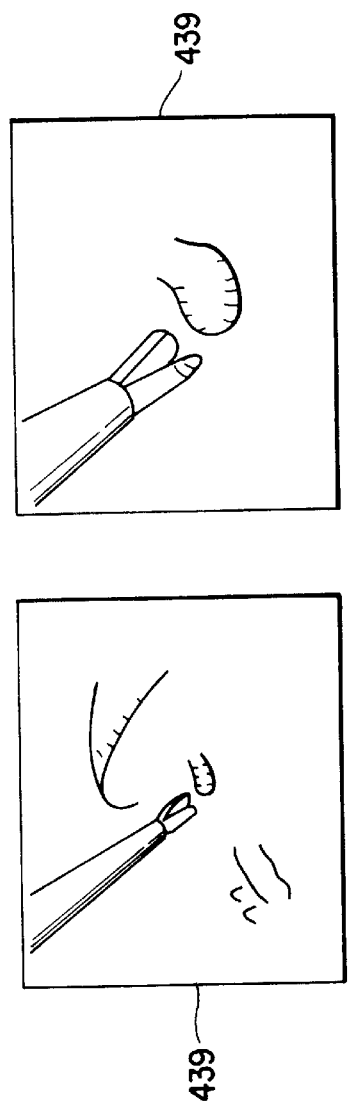
FIG. 42B
FIG. 42C

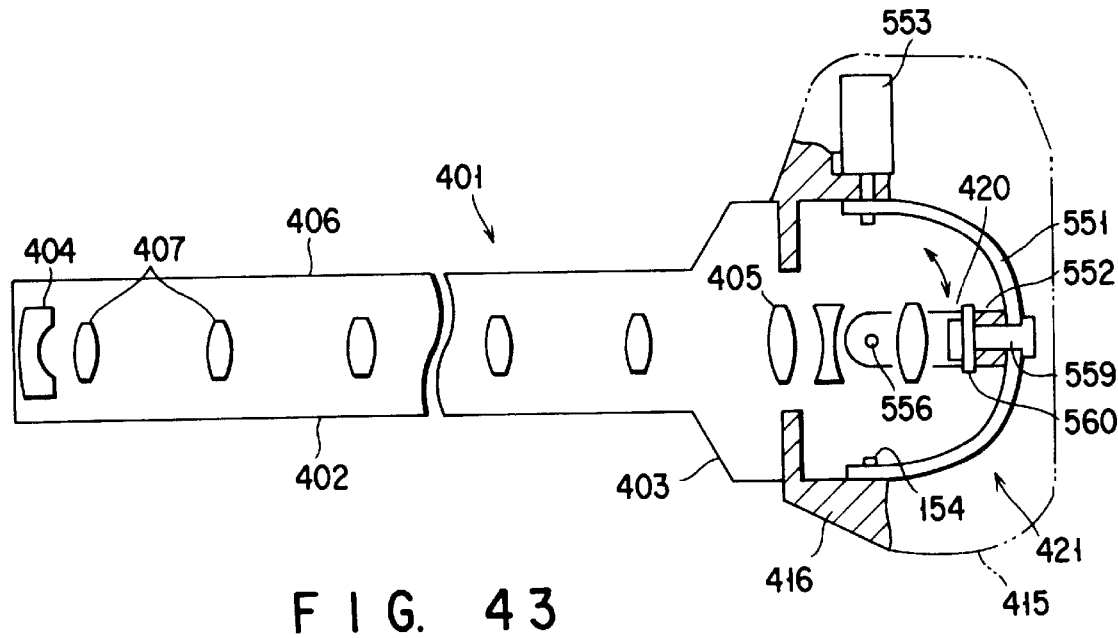
F I G. 43
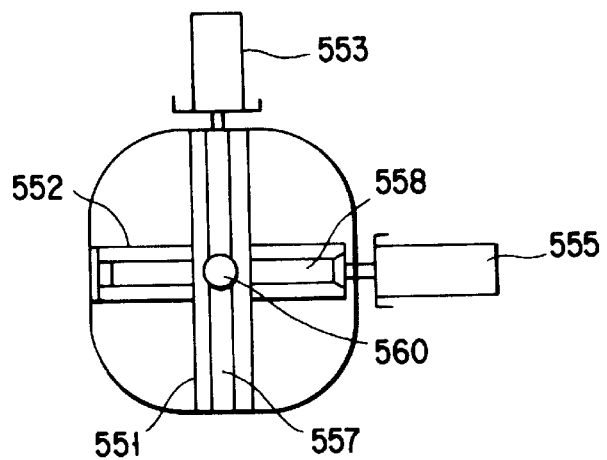
F I G. 44

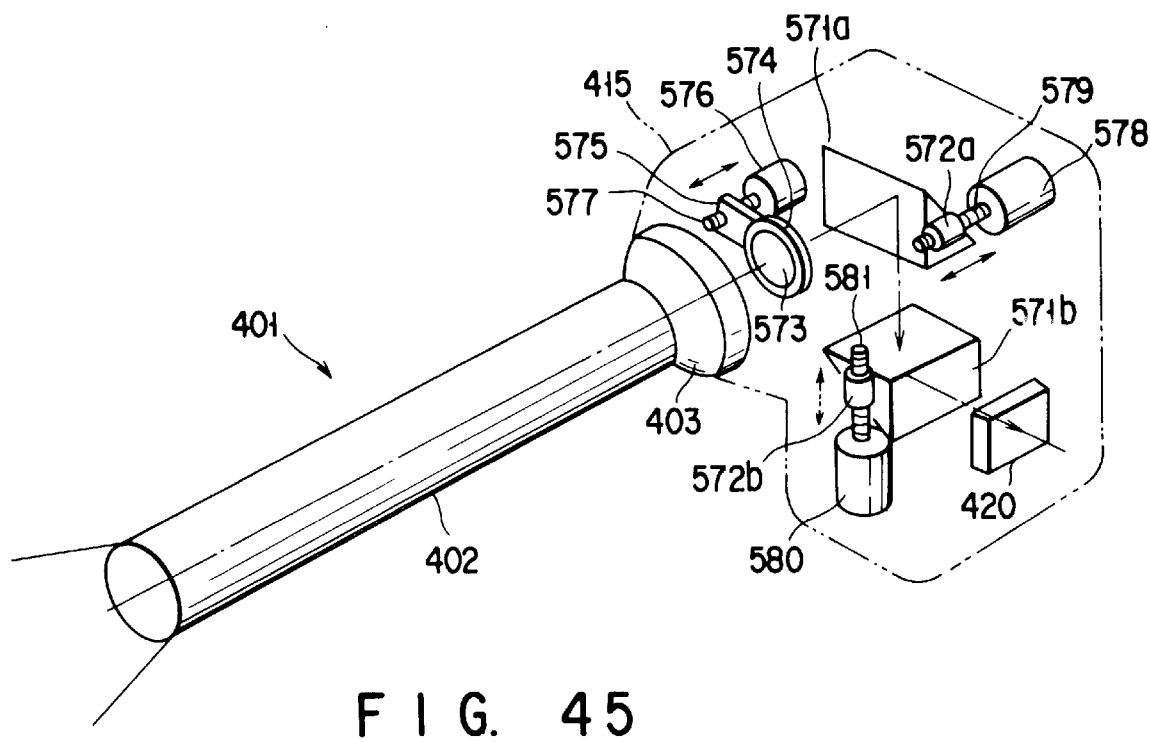
F I G. 45
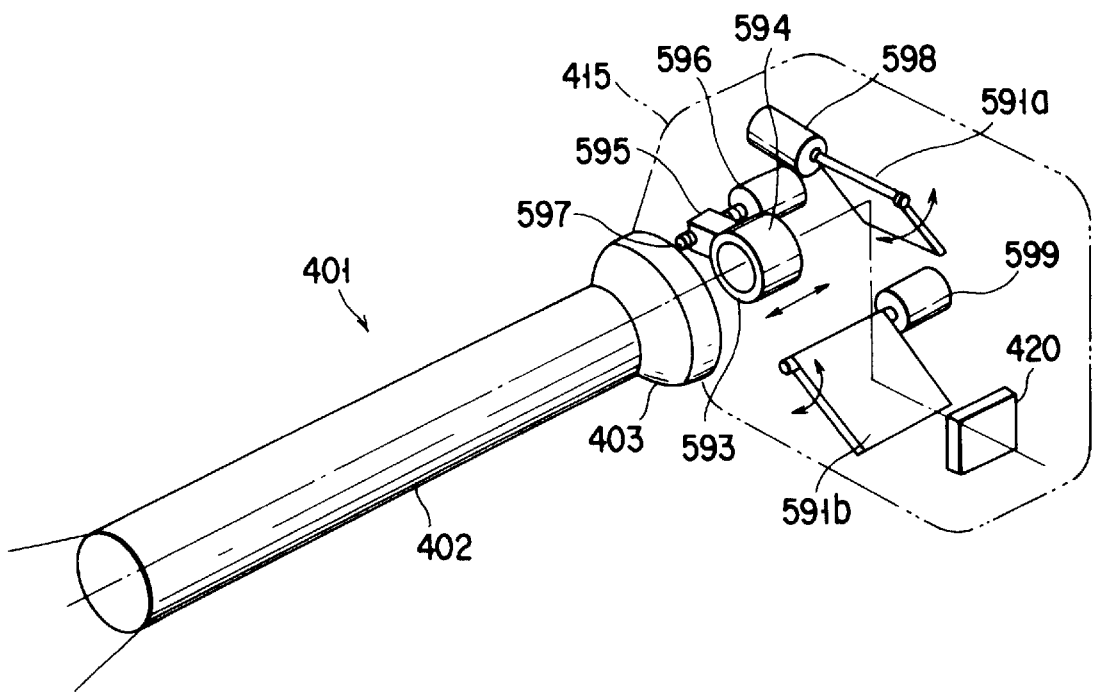
F I G. 46

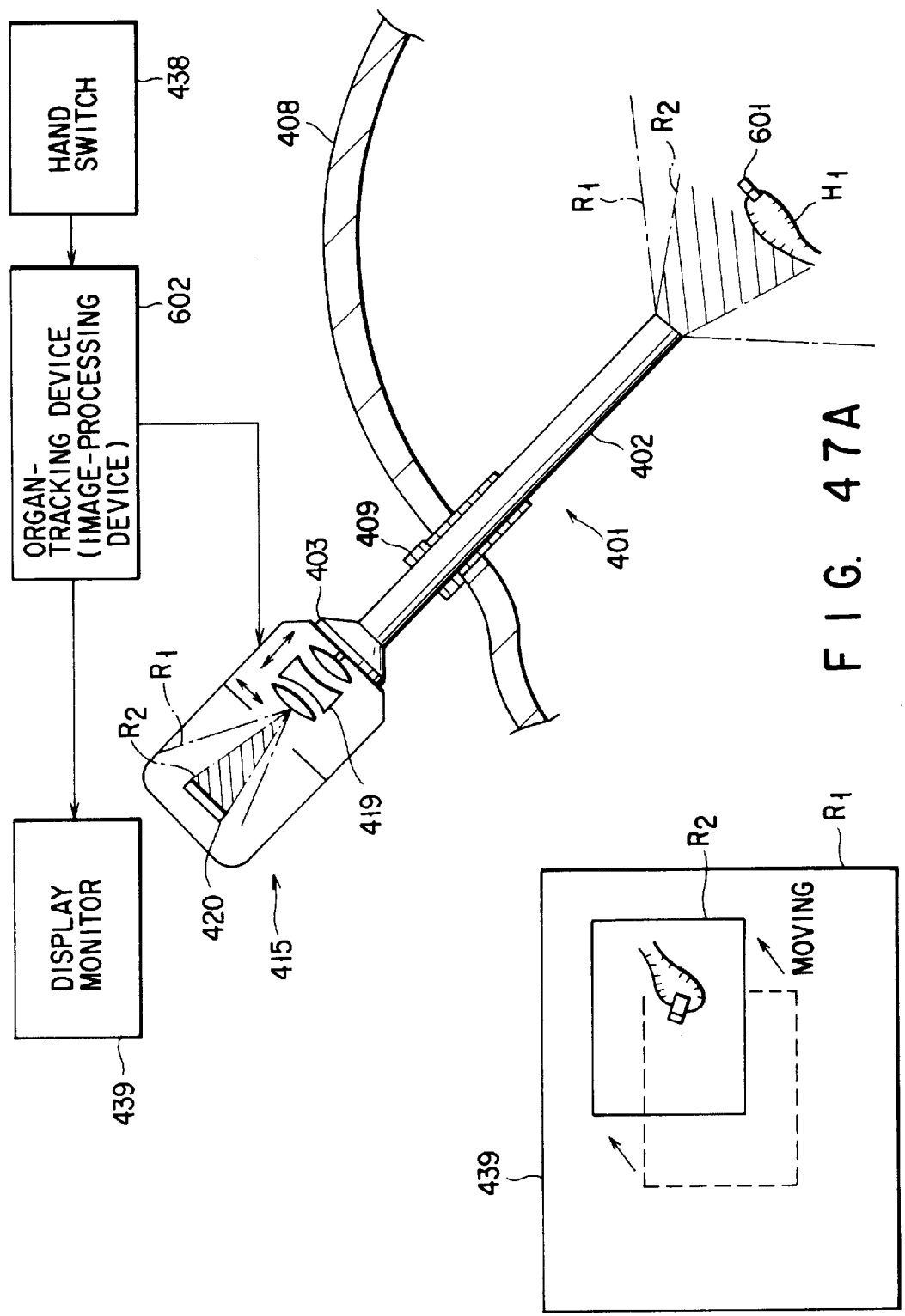

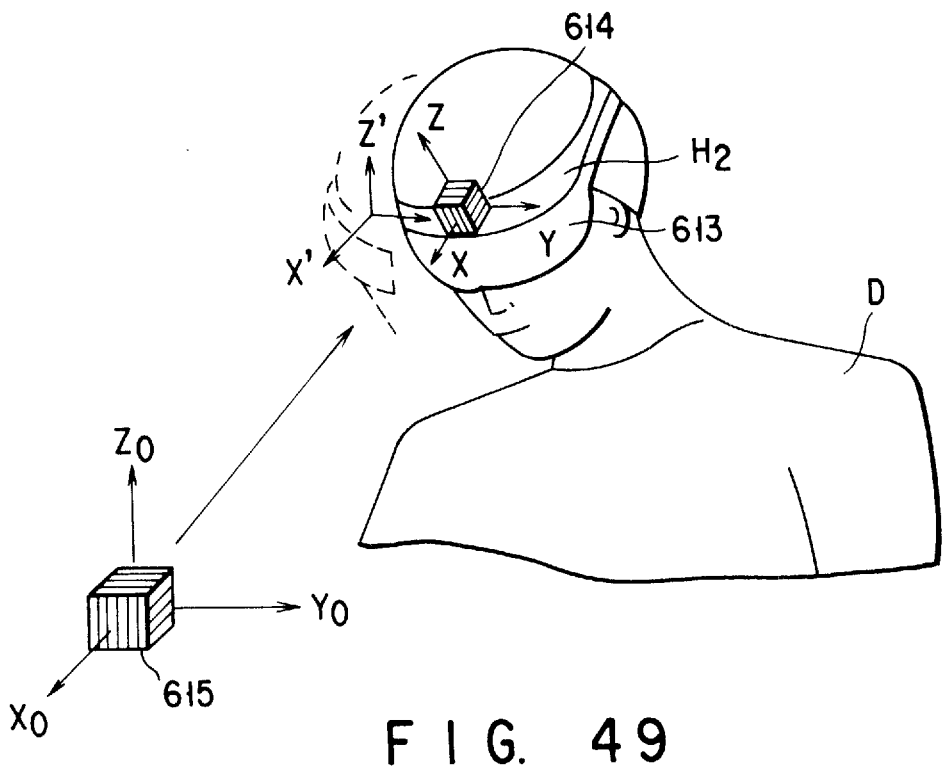
F I G. 49
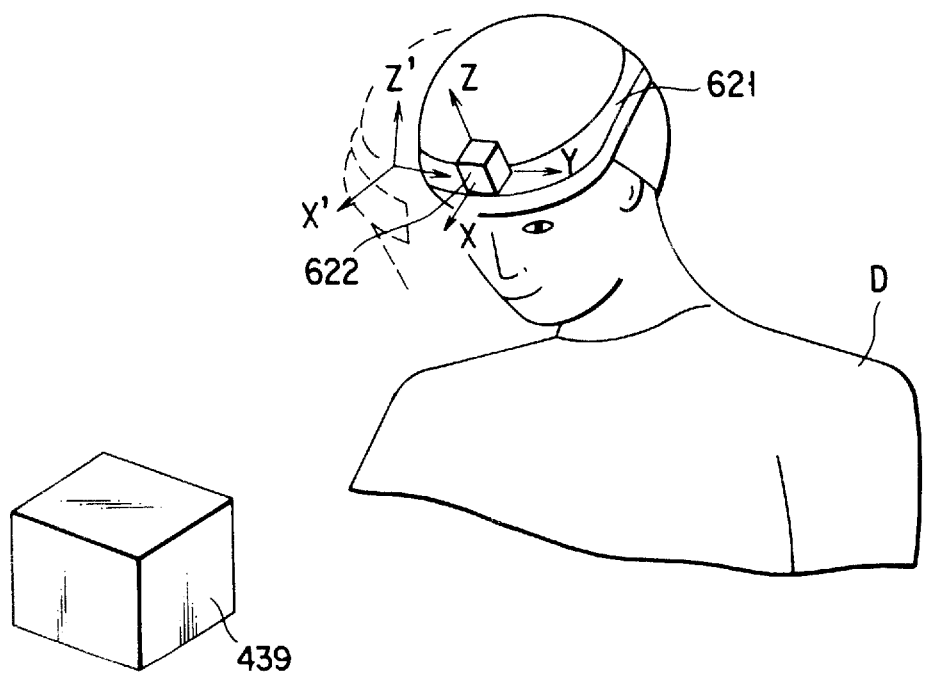
F I G. 50

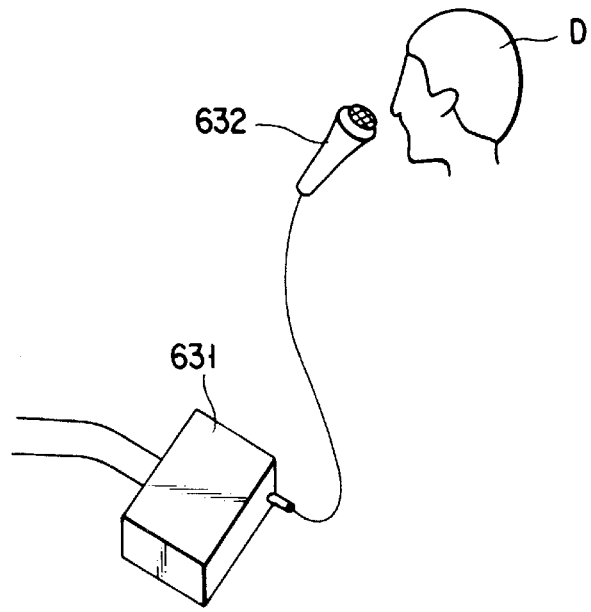
FIG. 51
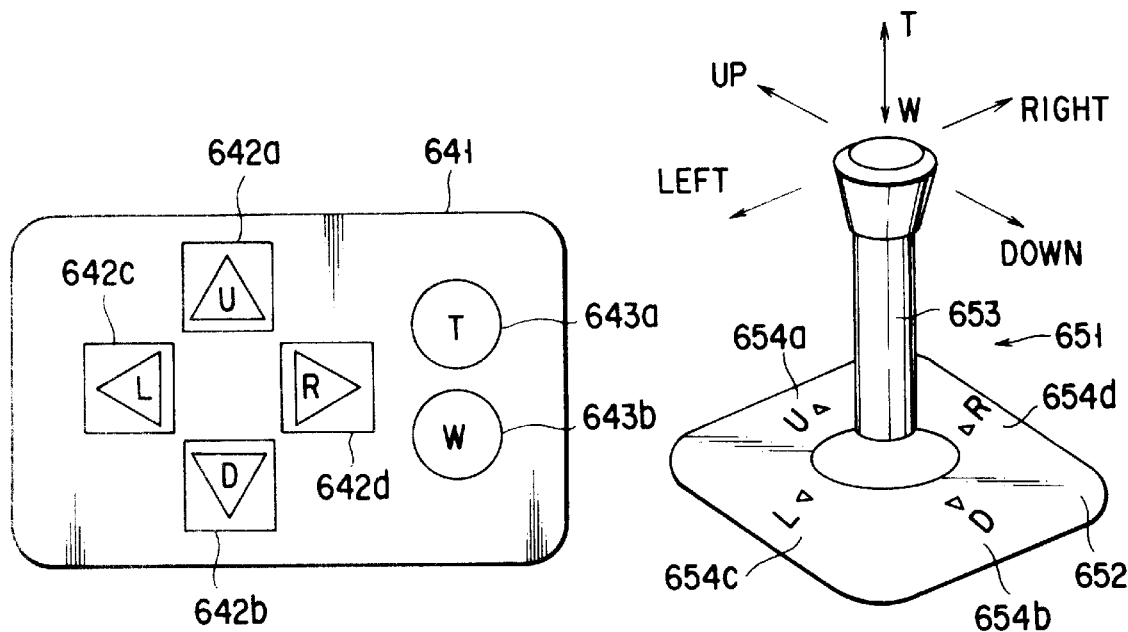
FIG. 52A
FIG. 52B

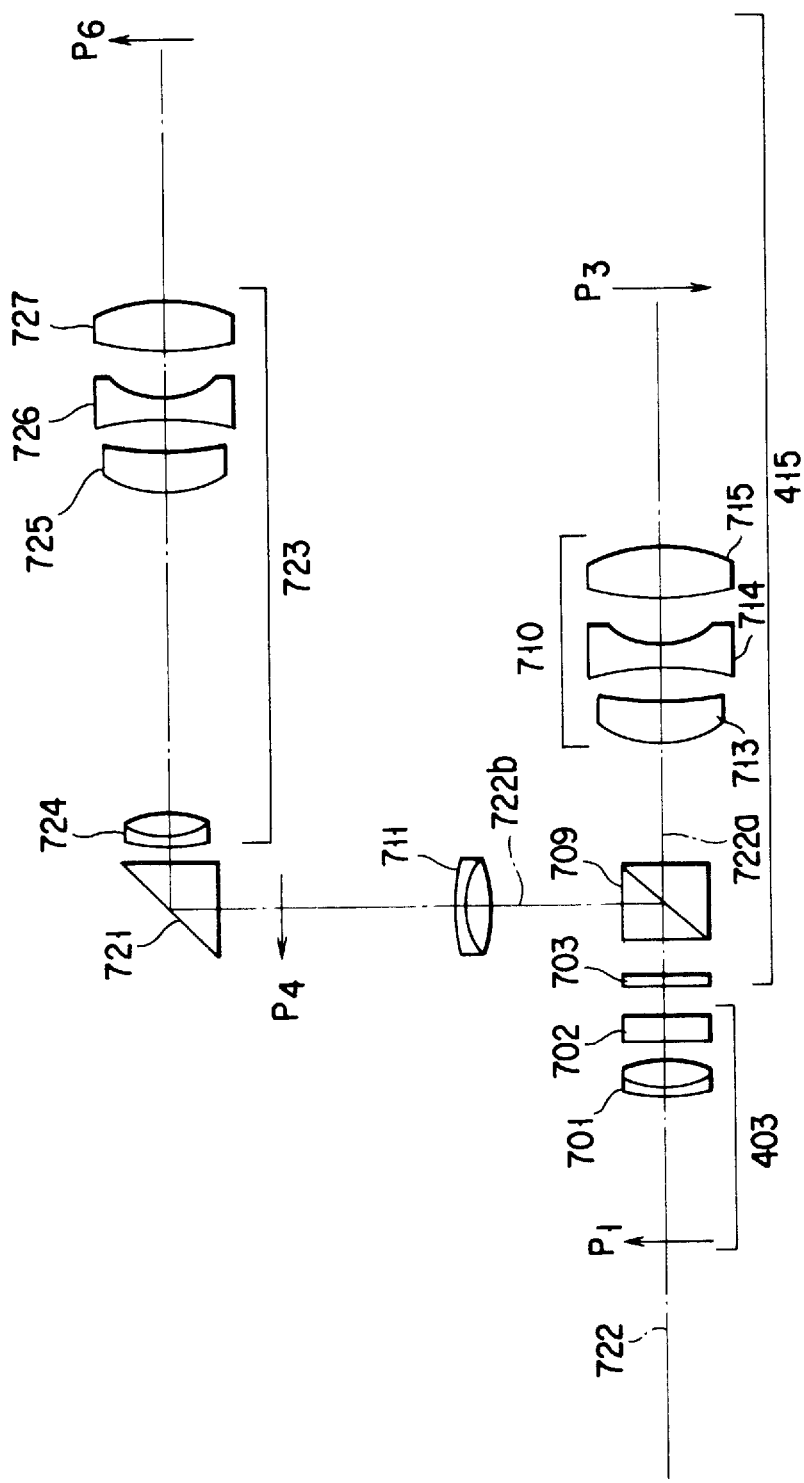
F I G. 55

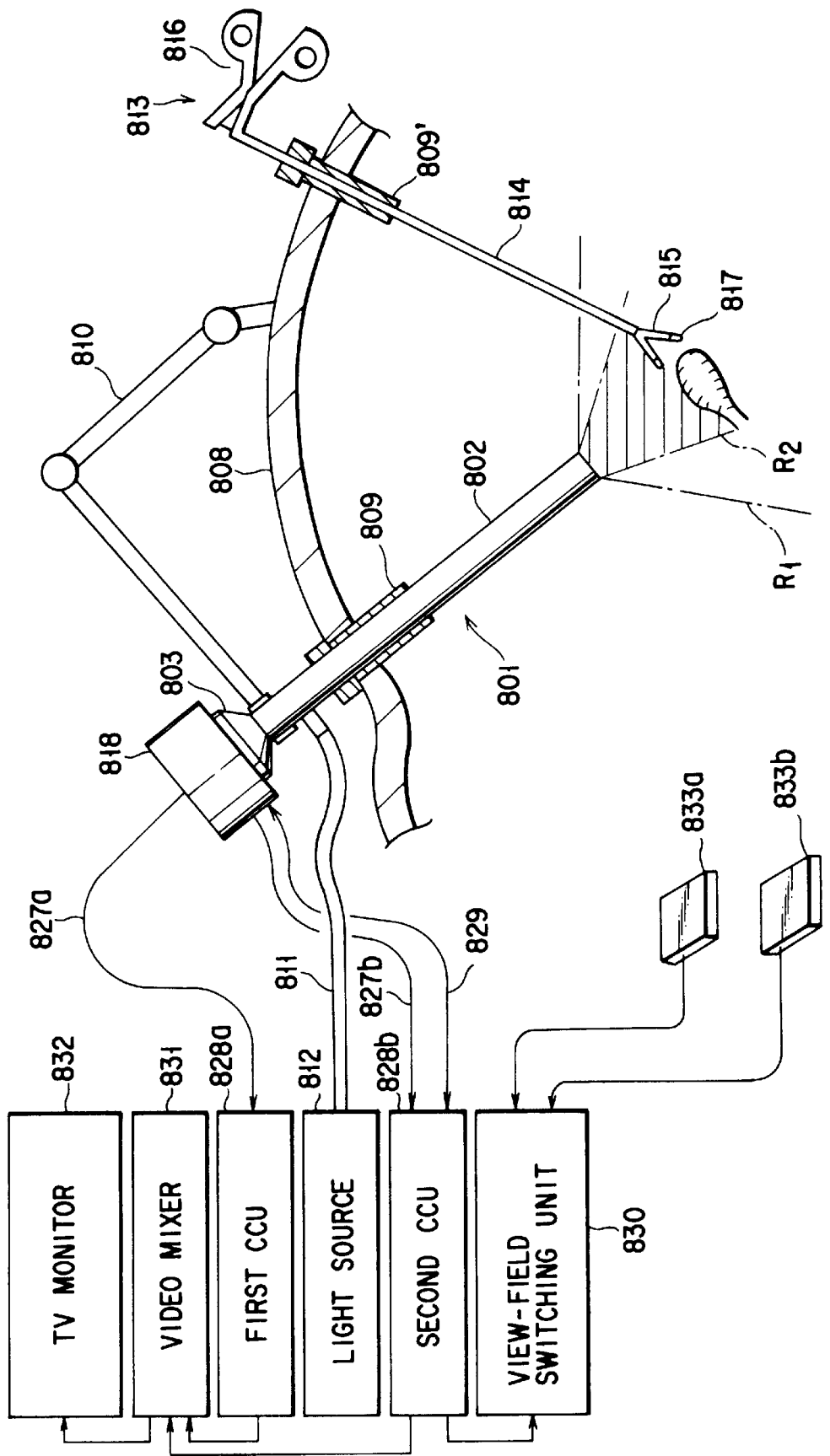
F I G. 57

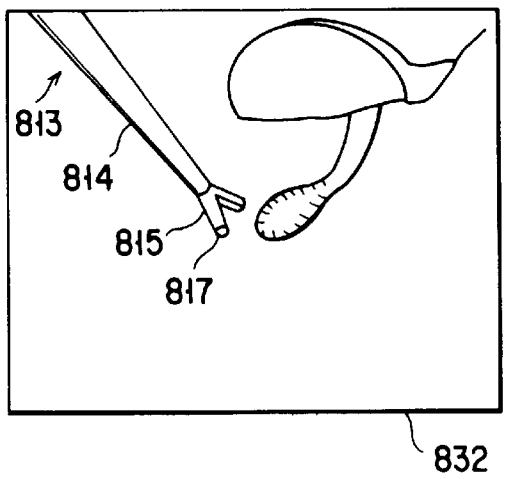
F I G. 60A
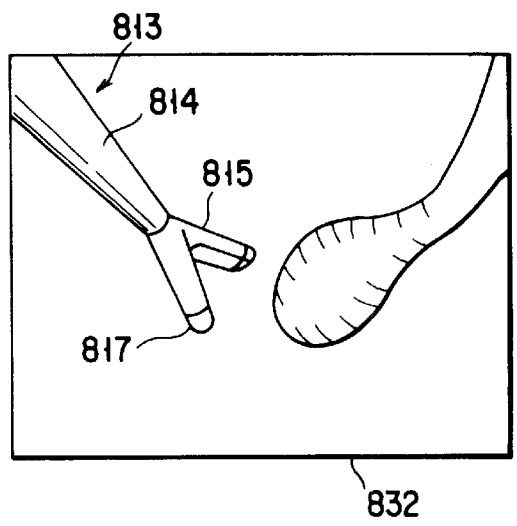
F I G. 60B
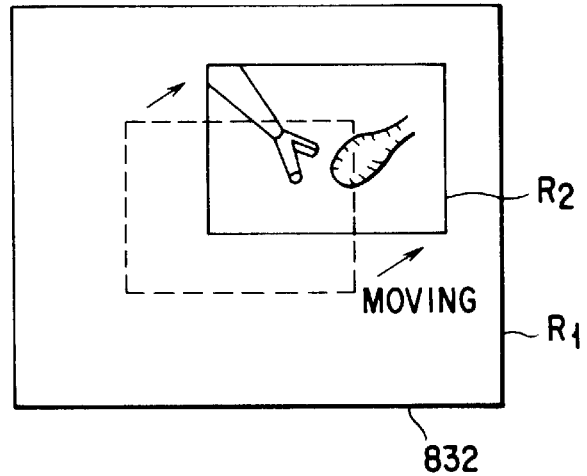
F I G. 60C
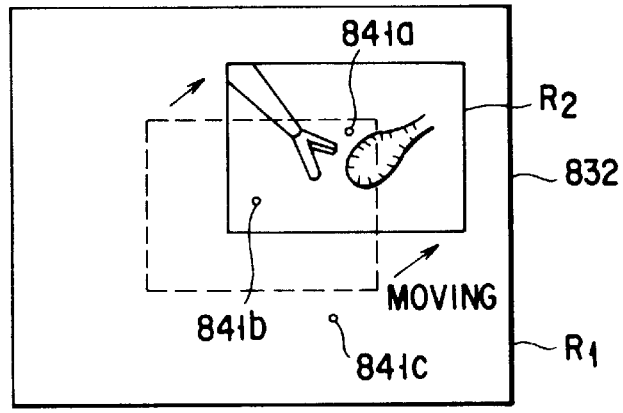
F I G. 61

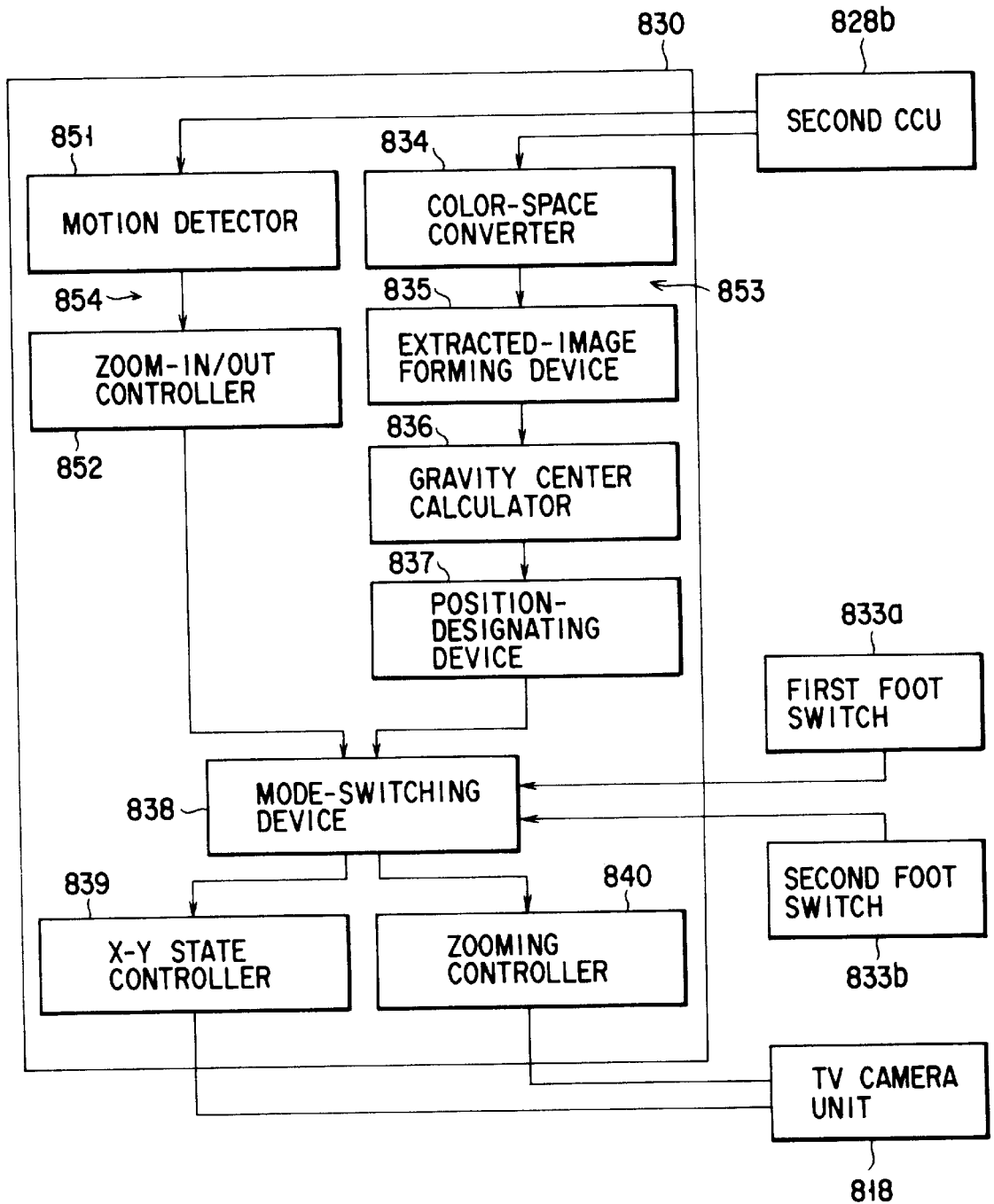
F I G. 62

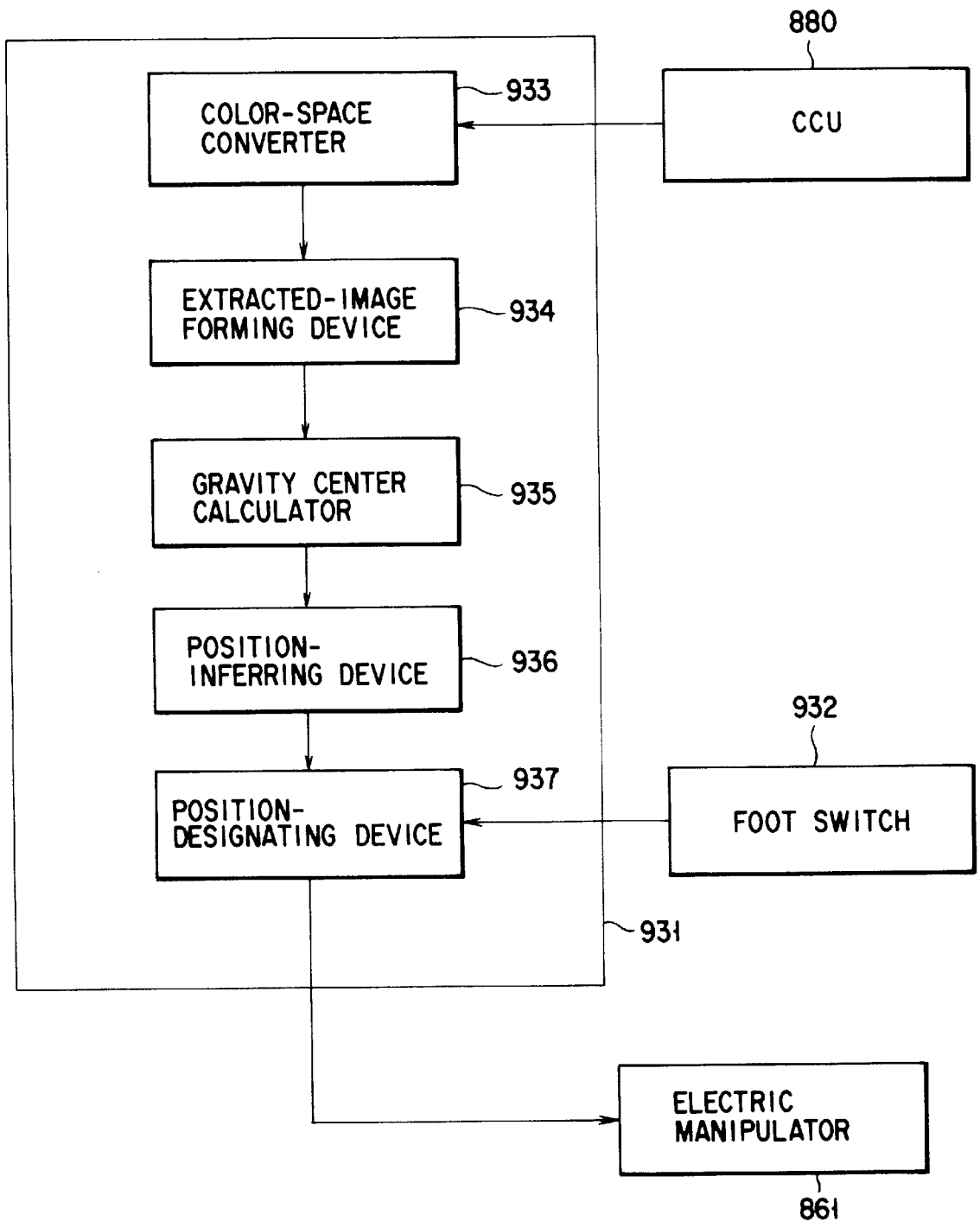
F I G. 65

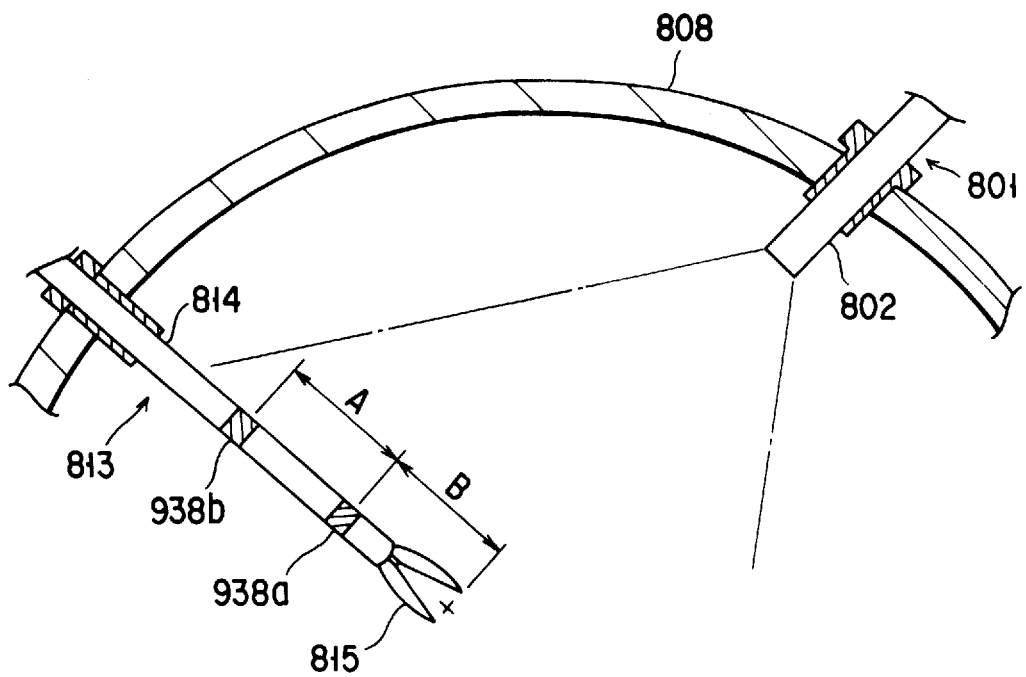
F I G. 66
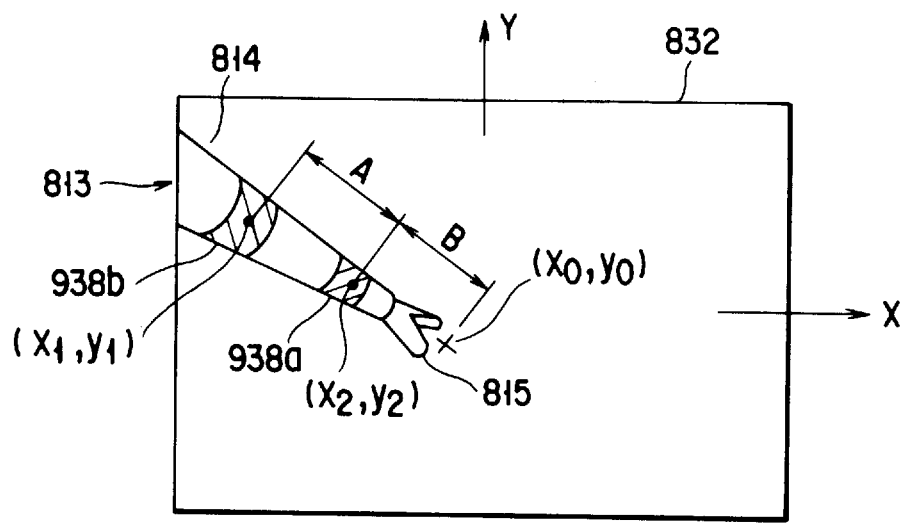
F I G. 67

IMAGE TRACKING ENDOSCOPE SYSTEM

BACKGROUND OF THE INVENTION

1. Field of the Invention

The present invention relates to an endoscope system in which an endoscope is inserted in part into a body cavity of a patient so as to enable a surgeon to observe an image of the interior of the body cavity.

2. Description of the Related Art

Recently so-called endoscope surgery has been put to practice. To perform endoscope surgery, a medical instrument and the insertion section of an endoscope are inserted, in part, into a patient's body cavity. The endoscope provides an image of the inserted part of the instrument and an affected tissue present in the body cavity. Observing the images of the instrument and the tissue, a surgeon manipulates the medical instrument, thereby treating the affected tissue. Endoscopic surgery is less invasive to the patient than surgery which begins with laparotomy or thoracotomy by using a knife. This is why endoscope surgery is now practiced frequently. In particular, laparoscope surgery using a laparoscope is performed often.

In endoscope surgery, the surgeon inserts the distal section of a medical instrument and the insertion section of the endoscope into the body cavity. A surgeon's assistant holds the endoscope. The endoscope provides the images of the medical instrument and affected tissue, both present in the body cavity. The images are displayed on a TV monitor. Seeing the images displayed, the surgeon manipulates the medical instrument, treating the affected tissue in the body cavity by, for example, cutting and extracting the affected tissue from the body cavity.

Whenever necessary, the surgeon may instruct the assistant to move the endoscope in a desired direction, so as to have the images of the instrument and affected tissue displayed at different positions on the TV monitor screen. Usually the surgeon wants the distal section of the instrument displayed in the center part of the monitor screen. In some cases he or she may need to have the distal section displayed at another position on the monitor screen.

For the assistant it is often difficult to move the endoscope in the specific direction the surgeon has designated. The assistant must be skillful to move the endoscope exactly in accordance with the surgeon's instructions. Further, it is very hard for the assistant to hold the endoscope for a long time until the endoscope surgery comes to an end. In most cases, other assistants need to participate, one after another.

Jpn. Pat. Appln. KOKAI Publication No. 5-337118 discloses a scope-holding device for holding an endoscope. The scope-holding device comprises an electrically driven manipulator and a motion-detecting unit. The manipulator is designed to hold and move an endoscope. The motion-detecting unit is devised to detect the distance and direction in which a medical instrument has been moved. During endoscope surgery, the manipulator holding an endoscope is moved for the distance and in the direction, which the motion-detecting unit has detected. The endoscope is therefore moved in the same way as the surgeon has moved the medical instrument. As a result, the image provided by the endoscope and displayed on a TV monitor is automatically switched as the surgeon moves the medical instrument.

PCT International Publication No. WO94/3113 discloses a scope-holding device of another type. This device comprises a drive unit and an input unit. The drive unit is designed to hold and move a surgery device such as an endoscope. The input unit has a foot switch or the like. When controlled by a signal output from the input unit, the drive unit moves the endoscope to a desired position so that the endoscope may provide an image of an object present at that position.

The scope-holding devices described above are disadvantageous in two respects. First, they are large and expensive, inevitably because they comprise a drive unit (e.g., an electrically driven manipulator) for moving an endoscope and a control unit for controlling the drive unit. Second, it takes much time to set an endoscope on the drive unit, and to connect the control unit to the drive unit.

SUMMARY OF THE INVENTION

In view of the foregoing, the present invention has been made. Its object is to provide an endoscope system which is compact, inexpensive and easy to set up.

According to the invention, there is provided an endoscope comprising: an endoscope; endoscope-holding means holding the endoscope; image pickup means having an optical system for receiving an endoscopic image from the endoscope; position-detecting means for detecting a position of an object observed trough the endoscope and for generating position data representing the position detected; display means for displaying the endoscopic image provided by the image pickup means; and view field switching means for switching a view field of the endoscope without moving the endoscope, in accordance with the position data.

The image of the object of interest can therefore be displayed at the same position on the screen of the display means even when the object moves in the body cavity. Further, the image of any other object located near the object of interest in the body cavity can be displayed at a designated position on the screen of the display means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 is a perspective view showing an endoscope surgery system according to a first embodiment of the present invention;

FIG. 2A is a diagram explaining how an image represented by a part of the image data stored in the image memory embodiment is displayed in a specified region of a TV monitor screen, in the endoscope surgery system shown in FIG. 1;

FIG. 2B is a diagram explaining how an image represented by another part of the image data is displayed at the same position on the TV monitor screen as the image represented by the first-mentioned part of the image data;

FIG. 4 is a perspective view showing an endoscope surgery system which is a second embodiment of this invention;

FIG. 5 is a block diagram of the control section incorporated in the endoscope surgery system shown in FIG. 4;

FIG. 7A is a diagram showing a modification of the position detector used in the second embodiment;

FIG. 7B is a plan view a remote-control panel for use in the second embodiment, in place of the hand switch;

FIG. 7C is a perspective view a joy stick for use in the second embodiment, in place of the hand switch;

FIG. 10A is a schematic diagram of the TV camera unit used in the fourth embodiment;

FIG. 10B is a diagram explaining how an image is displayed at the same position on the TV monitor screen incorporated in the fourth embodiment;

FIG. 11 is a block diagram showing the view-field switching unit incorporated in the fourth embodiment;

FIG. 16A is a side view of a medical instrument used in a endoscope surgery system according to a sixth embodiment of the present invention;

FIG. 16B is a front view of the TV monitor incorporated in the sixth embodiment, showing the wide-angle image displaying screen of the TV monitor;

FIG. 16C is a front view of the TV monitor shown in FIG. 16B, showing the enlarged-image displaying screen of the TV monitor;

FIG. 26 is a block diagram of a modification of the view-field switching unit according to the fourth embodiment;

FIG. 28A is a longitudinal sectional view of the TV camera connected to the ocular section of the scope incorporated in the tenth embodiment;

FIG. 28B is a diagram showing the CCD-driving mechanism provided in the tenth embodiment;

FIG. 28C is a side view of the flexible printed board connected to the CCD incorporated in the tenth embodiment;

FIG. 30 is a flow chart explaining how the forceps-tracking device operates to track the distal end of a pair of forceps;

FIG. 31 is a flow chart explaining how the forceps-tracking device operates in another mode;

FIG. 34A is a diagram illustrating an endoscope surgery system according to a thirteenth embodiment of this invention;

FIG. 34B is a front view of the TV monitor provided in the thirteenth embodiment, explaining how the monitor displays an image of an instrument and an image of a tissue as the endoscope tracks the instrument;

FIG. 34C is a front view of the TV monitor shown in FIG. 34B, explaining how the monitor displays an image of an instrument and an image of a tissue as the endoscope performs zooming operation;

FIG. 36 is a flow chart explaining how the thirteenth embodiment operates;

FIG. 37A is a longitudinal sectional view of the TV camera connected to the ocular section of the scope incorporated in an endoscope surgery system according to a fourteenth embodiment of this invention;

FIG. 37B is a diagram showing the CCD-driving mechanism incorporated in the fourteenth embodiment;

FIG. 38A is a longitudinal sectional view of the main section of an endoscope surgery system according to a fifteenth embodiment of this invention;

FIG. 38B is a longitudinal sectional view of the main section of an endoscope surgery system according to a sixteenth embodiment of this invention;

FIG. 42A is a longitudinal sectional view of the endoscope incorporated in a endoscope surgery system according to a nineteenth embodiment of the present invention;

FIGS. 42B and 42C are front views of the display monitor used in the nineteenth embodiment, explaining how the view field of the scope is switched;

FIG. 43 is a longitudinal sectional view of the scope incorporated in a endoscope surgery system according to a twentieth embodiment of the preset invention;

FIG. 44 is a schematic representation of the CCD-driving mechanism incorporated in the twentieth embodiment;

FIG. 45 is a partly sectional, perspective view of the scope used in an endoscope surgery system according to a twenty-first embodiment of the invention;

FIG. 46 is a partly sectional, perspective view of the scope used in an endoscope surgery system according to a twenty-second embodiment of this invention;

FIG. 47A is a diagram showing an endoscope surgery system according to a twenty-third embodiment of this invention;

FIG. 47B is a front view of the TV monitor provided in the twenty-third embodiment;

FIG. 49 is a perspective view showing the position-designating device and the view field controller, both incorporated in the twenty-fourth embodiment;

FIG. 50 is a perspective view showing the main section of an endoscope surgery system according to a twenty-fifth embodiment of this invention;

FIG. 51 is a perspective view showing the main section of an endoscope surgery system according to a twenty-sixth embodiment of the invention;

FIG. 52A is a plan view of a remote-control panel used in an endoscope surgery system according to a twenty-seventh embodiment of the present invention;

FIG. 52B is a perspective view of the joy stick used in an endoscope surgery system according to a twenty-eighth embodiment of this invention;

FIG. 55 illustrates the optical system provided in an endoscope surgery system according to a thirty-first embodiment of the invention;

FIG. 57 is a diagram representing an endoscope surgery system according to a thirty-third embodiment of this invention;

FIG. 60A is a plan view of the TV monitor used in the thirty-third embodiment, showing a wide-angle image displayed on the screen of the TV monitor;

FIG. 60B is a plan view of the TV monitor used in the thirty-third embodiment, showing an enlarged image displayed on the screen of the TV monitor;

FIG. 60C is a plan view of the TV monitor used in the thirty-third embodiment, explaining how the view field of the scope is switched;

FIG. 61 is a plan view of the TV monitor used in the thirty-third embodiment, showing the images of organs each having a portion colored with pigment;

FIG. 62 is a block diagram of the view field control unit incorporated in an endoscope surgery system according to a thirty-fourth embodiment of the present invention;

FIG. 65 is a block diagram of the view field control unit incorporated in the thirty-sixth embodiment;

FIG. 66 is a diagram showing the medical instrument used in the thirty-sixth embodiment and the color markers provided on the distal end portion of the instrument; and FIG. 67 is a plan view of the TV monitor used in the thirty-sixth embodiment, showing the image provided by the rigid scope.

DETAILED DESCRIPTION OF THE PREFERRED EMBODIMENTS

Embodiments of the present invention will be now described in detail, with reference to the accompanying drawings.

Figure 3:
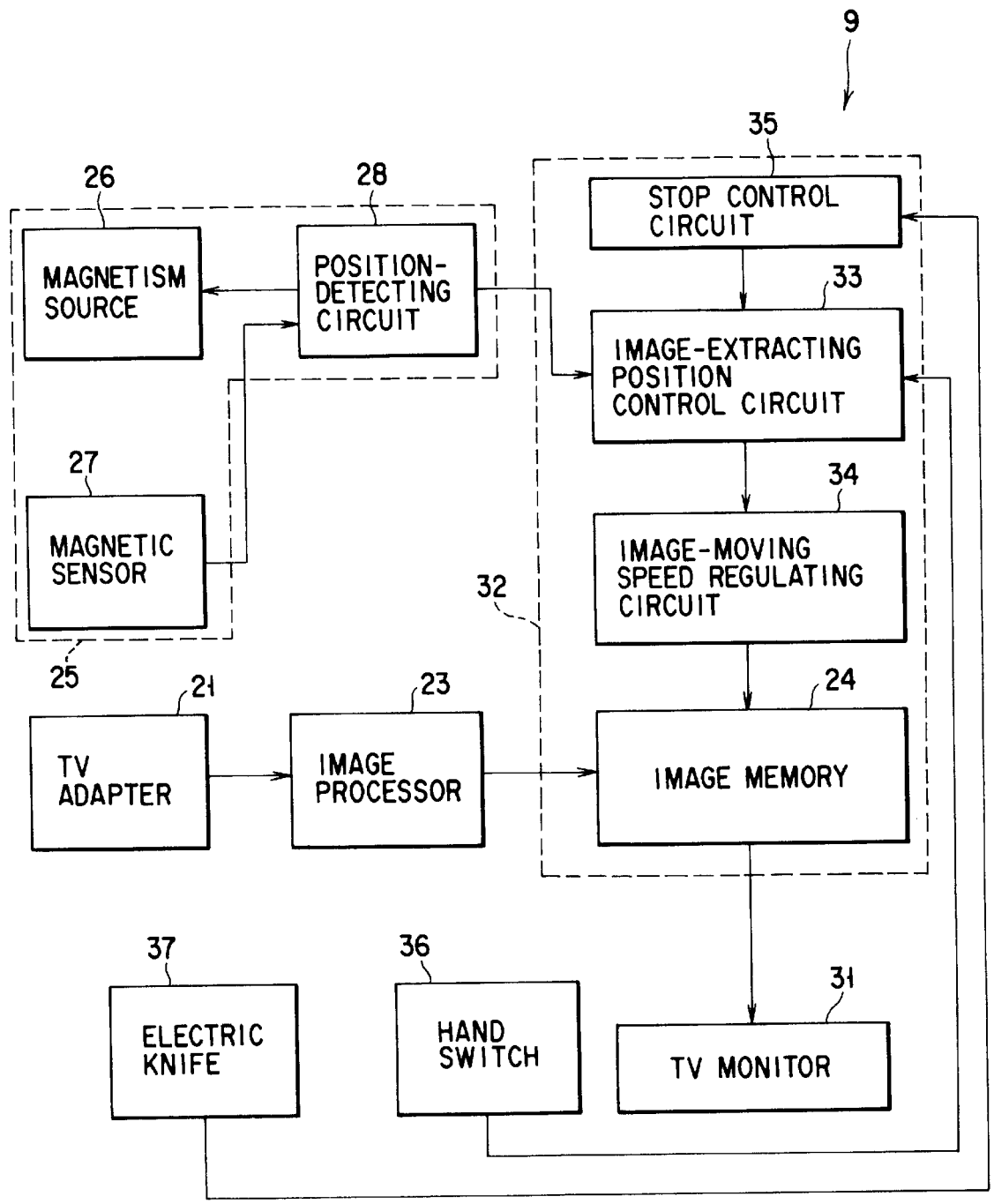
FIG. 3 is a block diagram of the control section incorporated in the endoscope surgery system shown in FIG. 1.

FIGS. 1 to 3 show an endoscope surgery system which is the first embodiment of the invention. FIG. 1 explains how the endoscope surgery system is operated. As shown in FIG. 1, a pneumoperitoneal stylus pierces the abdominal wall 1 into the peritoneal cavity 2 of a patient. Through the pneumoperitoneal stylus gas such as carbon dioxide gas is supplied into the peritoneal cavity 2, thereby performing pneumoperitoneum. The cavity 2 is therefore expanded.

Two trocars 3 and 4 are set in the openings incised in the abdominal wall 1. The rigid insertion section of an endoscope 5 is inserted through the first trocar 3 into the peritoneal cavity 2. An medical instrument 6 is inserted through the second trocar 4 into the peritoneal cavity 2.

A scope-holding device 8 is fastened to one side of an operating table 7. The device 8 holds the endoscope 5 in a desired position. The scope-holding device 8 has a base 11 which can slide on the side of the table 7 in two opposite directions indicated by arrows A. A post 12 stands upright on the base 11. A base arm 13 is connected at one end to the upper end of the post 12. The base arm 13 extends in a substantially horizontal direction. It can rotate around the post 12 in a horizontal plane, in the direction of arrow B. To the other end of the base arm 13 a holding arm 14 is connected by a pin 13A. The arm 14 can rotate around the pin 13A in a vertical plane, in the direction of arrow C. The arm 14 holds a link mechanism 15.

The link mechanism 15 comprises vertical parallel links 16a and horizontal parallel links 16b. The links 16a and 16b are coupled together, constituting a parallel link chain. The vertical links 16a are coupled at lower end to the base arm 13 and can rotate in a vertical plane. Connected to the free ends of the horizontal links 16b is a holder 17, which holds the endoscope 5.

The movable components of the scope-holding device 8 (e.g. the arms 13 and 14, the vertical links 16a, the horizontal links 16b and the holder 17) are held in place due to the friction between them and by fastening screws 18. Hence, when a force is applied to the scope-holding device 8, the arms 13 and 14 are rotated and the link mechanism 15 is deformed, whereby the holder 17 and, hence, the endoscope held by the holder 17 can be set at any desired position.

As shown in FIG. 1, a TV adapter 21 is attached to the ocular section of the endoscope 5. The TV adapter 21 incorporates a CCD. The CCD receives the light reflected by any object present in the field of view of the endoscope 5 and converts the light into electric image signals which represent an image of that object. The image signals output from the TV adapter 21 are supplied via a signal cable 22 to the control section 9 which is provided in the endoscope surgery system.

As shown in FIG. 3, the control section 9 comprises an image processor 23, a magnetic three-dimensional position sensor 25, and an image-moving unit 32. The position sensor 25 has a magnetism source 26, a magnetic sensor 27, and a position-detecting circuit 28. The image-moving unit 32 has an image memory 24, an image-moving speed regulating circuit 34, an image-extracting position control circuit 33, and a stop control circuit 35.

In the control section 9, the image signals are supplied to the image processor 23. The processor 23 processes the signals into image data, which is supplied to the image-moving unit 32. In the unit 32, the image data is stored into the image memory 24.

As shown in FIG. 1, the magnetism source 26 of the magnetic three-dimensional position sensor 25 is removably connected to the proximal portion of the endoscope 5, which is not inserted in the peritoneal cavity 2. Thus, the magnetism source 26 is located outside the patient. The magnetic sensor 27 of the position sensor 25 is removably mounted on the proximal portion of the medical instrument 6, which is not inserted in the peritoneal cavity 2. In other words, the sensor 27 is provided outside patient.

The magnetism source 26 has three coils whose axes are X, Y and Z axes, intersecting with one another at right angles. Similarly, the magnetic sensor 27 has three coils whose axes are X, Y and Z axes. Three pulse signals, each having a time lag with respect to any other, are supplied to the coils of the magnetism source 26, which generate three magnetic fields. These magnetic fields are detected by the coils of the magnetic sensor 27, respectively. The sensor 27 generates three electric signals from the magnetic fields. The electric signals are supplied to the position-detecting circuit 28.

The position-detecting circuit 28 processes the three electric signals input, thereby calculating the position the magnetic sensor 27 assumes with respect to the position of the magnetism source 26 which is regarded as a fixed point (i.e., reference point). To be more precise, the X-axis coordinate, Y-axis coordinate and the Z-axis coordinate of the sensor 27 and the angles through which the sensor 27 has been rotated around the X, Y and Z axes. The position which the magnetic sensor 27 takes outside the patient is thereby determined. From the position of the sensor 27, thus determined, the position which the distal end 29 of the instrument 6 in the peritoneal cavity 2 is calculated by means of rotational/parallel coordinate transform.

Thus, the position sensor 25, which comprises the magnetism source 26, the magnetic sensor 27 and the position-detecting circuit 28, acquires data which represents the position the distal end of the medical instrument 6 takes in the peritoneal cavity 2.

As seen from FIG. 3, the endoscope surgery system further comprises a TV monitor 31, a hand switch 36, and an electric knife 37. The TV monitor 31, which is used as an image display, is connected to the image memory 24 incorporated in the image-moving unit 32. The image-moving unit 32 extracts a part of the image data stored in the image memory 24, which represents the image of the distal end 29 of the instrument 6 and the image of any other object located near the distal end 29. That part of the image data is supplied from the unit 32 to the TV monitor 31, which displays the image of the distal end 29 and the image of the other object. The image-moving unit 32 is designed to cause the TV monitor 31 to display these images at the same position on the screen even if the distal end 29 of the instrument 6 moves in the peritoneal cavity 2.

In the image-moving unit 32, the image-moving speed regulating circuit 34 and the stop control circuit 35 are connected to the image-extracting position control circuit 33. The image-moving speed regulating circuit 34 is connected to the image memory 24.

As shown in FIG. 3, the position-detecting circuit 28 provided in the position sensor 25 is connected to the image-extracting position control circuit 33. The circuit 33 receives the data representing the position of the distal end 29 of the instrument 6, which the position-detecting circuit 28 has detected. In accordance with this position data, the circuit 33 extracts that part of the image data stored in the image memory 24 which represents the image of the distal end 29 and the image any object near the distal end 29. The part of the image data, thus extracted, is supplied to the TV monitor 31. The image-extracting position control circuit 33 also generates an image-enlarging signal, which is supplied to the TV monitor 31. The image-moving speed regulating circuit 34 regulates the speed at which the images will move on the screen of the TV monitor 31.

The image-moving unit 32 starts operating when the hand switch 36 is closed. The stop control circuit 35 prevents the image-extracting position control circuit 33 and the image-moving speed regulating circuit 34, while a surgeon is treating an affected tissue in the peritoneal cavity 2 with the electric knife 37, applying electric energy to the tissue.

It will now be explained how endoscope surgery is performed by using the endoscope surgery system shown in FIG. 1.

At first, the surgeon inserts the rigid insertion section of the endoscope 5 into the peritoneal cavity 2 through the first trocar 3, and the distal section of the medical instrument 6 into the cavity 2 through the second trocar 5. The endoscope 5 is secured at its proximal end to the holder 17 of the scope-holding device 8. Then, the magnetism source 26 is connected to the proximal portion of the endoscope 5, with one of its three coordinate axes aligned with the optical axis of the endoscope 5. The position which the source 26 will assume in the image provided by the endoscope 5 is thereby related to the position of the source 26 which the magnetic sensor 27 will detect.

Next, the magnetic sensor 27 is attached to the proximal portion of the medical instrument 6. The magnetic sensor 27 detects the positions which its three axes take with respect to the reference point (i.e., the position of the magnetism source 26). The sensor 27 detects the angles through which it is rotated around the three axes. More precisely, the three coils of the sensor 27 generate three electric signals from the magnetic fields emanating from the three coils of the magnetism source 26. The electric signals are supplied from the magnetic sensor 27 to the position-detecting circuit 28. The circuit 28 processes the three electric signals, thereby calculating the position which the distal end 29 of the instrument 6 by means of rotational/parallel coordinate transform.

The CCD incorporated in the TV adapter 21 receives the light reflected by the distal end 29 of the instrument 6 and the affected tissue, both present in the field of view of the endoscope 5. The CCD converts the light into electric image signals representing an image of the distal end 29 and the tissue. The image signals are supplied from the TV adapter 21 to the control section 9 through the signal cable 22. The section 9 generates image data representing the image of the distal end 29 and the image of the affected tissue. The image data is supplied to the TV monitor 31, which displays the images of the distal end 19 and the affected tissue.

Seeing these images displayed on the screen of the TV monitor 31, the surgeon manipulates the medical instrument 6. As the distal end 29 of the instrument 6 moves, the image-moving unit 32 operates as will be described below.

The CCD in the TV adapter 21 receives the light reflected from the instrument 6 and the affected tissue, both caught in the field of view of the endoscope 5. The CCD converts the light into image signals, which are supplied to the image processor 23. The image processor 23 processes the signals into image data 24D. The image data 24D is stored into the image memory 24.

The image-extracting position control circuit 33 supplies a control signal to the image memory 24 via the image-moving speed regulating circuit 34. That part of the image data 24D which represents an image $24d_1$ is extracted from the image memory 24 as shown in FIG. 2A. The image $24d_1$ includes the image of the distal end 29 and the image any object located near the distal end 29. This part of the image data 24D is supplied to the TV monitor 31. The TV monitor 31 displays the image $24d_1$ in an enlarged size.

Meanwhile the position-detecting circuit 28 generates the position data representing the position of the distal end 29. The position data is supplied to the image-extracting position control circuit 33. The control circuit 33 multiplies the position data by a coefficient so that the image of the distal end 29 may be displayed at a fixed position on the screen of the TV monitor 31. The multiplication produces control data, which is supplied from the control circuit 33 to the image memory 24. In accordance with the control data it is determined which part of the image data 24D should be extracted when the instrument 6 is moved and, hence, its distal end 29 moves in the peritoneal cavity 2. As a result of this, the image of the distal end 29, displayed in the enlarged size, remains at the same position on the TV monitor screen, though the distal end 29 has moved in the in the peritoneal cavity 2. In other words, as the distal end 29 of the instrument 6 moves, the image $24d_1$ represented by the extracted part of the image data 24D stored in the memory 24 is switched to an image $24d_2$ as if it tracked the distal end 29, as is illustrated in FIG. 2B. The image $24d_2$ is displayed in an enlarged size on the screen of the TV monitor 31.

If the amount of the control data which the control circuit 33 has generated per unit time exceeds a preset value, the image-moving speed regulating circuit 34 divides the control data into blocks and supplies these control data blocks to the image memory 24 one after another. All control data blocks parts, but the last block, are equal in amount to the preset value. Hence, the image is not switched abruptly and moves smoothly and continuously on the screen of the TV monitor 31, even if the instrument 6 is moved quickly. The surgeon can therefore clearly understand the position which the instrument 6 assumes at present.

The tracking of the instrument 6 is achieved only while the hand switch 36 remains closed. As long as the switch 36 is closed, it supplies a control signal to the image-extracting position control circuit 33. The control circuit 33 operates in accordance with this control signal.

As long as the electric knife 37 is operated, it supplies a monitor signal to the stop control circuit 35. In response to the monitor signal, the stop control circuit 35 stops the image-extracting position control circuit 33. Thus, the control circuit 33 is held in inoperative state even if the surgeon turns on the hand switch 36 while he or she is using the electric knife 37.

The hand switch 36 can be replaced by a foot switch or a speech-recognizing input device or can be used in combination therewith. The medical instrument is not limited to the electric knife 37. It may be a laser knife or a microwave knife. Further, the magnetism source 26 can be mounted on any object other than the endoscope 5, provided that the magnetic fields it generates can be detected by the magnetic sensor 27. If this is the case, a position sensor (e.g., an angle sensor) on the scope-holding device 8 to determine the positional relationship between the device 8 and the reference point (i.e., the position of the magnetism source 26) and calculate the position of the distal end 29 of the instrument 6 from the reference coordinates of the device 8.

The endoscope surgery system shown in FIG. 1 is advantageous in the following respects.

The position which the distal end 29 of the instrument 6 assumes is detected, and the image $24d_1$ represented by the extracted part of the image data 24D stored in the memory 24 is switched to an image $24d_2$ by electronic means. A mechanical unit, an electrically drive holder or a manipulator need not be used to move the endoscope 5 as the instrument 6 is moved, unlike in conventional endoscope surgery systems.

Further, the scope-holding device 8 is of the type commercially available and can yet serve to track the distal end 29 of the instrument 6 so that the image displayed by the TV monitor 31 may be switched to another. Since the device 8 is a commercially available one, the endoscope surgery system can be compact and relatively inexpensive and can be easy to set up and operate.

Moreover, the control signal used in the control section 9 contains no noise while to achieve the switching of the image since the stop control circuit 35 prevents the image displayed on the TV monitor 31 from being switched to another while the surgeon is using the electric knife 37. Therefore, no errors will occur while the image data is processed to perform the switching of image.

Another endoscope surgery system, which is the second embodiment of this invention, will be described with reference to FIGS. 4 and 5. FIG. 4 is a perspective view of this endoscope surgery system. FIG. 5 is a block diagram of the control section 9 incorporated in the system. This system differs from the first embodiment shown in FIG. 1 in that a shape marker 41 is used in place of the magnetism source 26 and magnetic sensor 27 of the three-dimensional position sensor 25. Except for this feature, the system is basically identical to the first embodiment (FIG. 1).

As shown in FIG. 4, the shape marker 41 is mounted on the distal end portion of a medical instrument 6. It has a shape different from any object that may exist in the peritoneal cavity 2 of a patient and can therefore distinguished easily.

As shown in FIG. 5, the control section 9 comprises a TV adapter 21, an image processor 23, a pattern-matching circuit 42, and an image-moving unit 43. The system has a TV monitor 31, a hand switch 36 and an electric knife 37, all connected to the image-moving unit 43. The pattern-matching circuit 42 is designed to detect the position of the distal end of the instrument 6. The circuit 42 is connected to the image processor 23 and the image-moving unit 43. The image-moving unit 43 is identical to the image-moving unit 32 incorporated in the first embodiment (FIG. 1).

The pattern-matching circuit 42 receives the image data provided by the endoscope 5. From the image data, the circuit 42 determines how the shaped marker 41 has moved. To detect the position of the marker 41, the circuit 42 converts the image data to binary image data and performs outline-emphasis on the binary image data. Then, the circuit 42 compares the outline-emphasized image data with the image data representing the marker 41, determining that the outline-emphasized image data represents the marker 41. Thus, the pattern-matching circuit 42 generates data representing the position of the distal end of the instrument 6 and, as if the endoscope 5 tracked the distal end of the medical instrument 6.

The image data generated by the pattern-matching circuit 42 is input to the image-moving unit 43. The image-moving unit 43 performs exactly the same function as the image-moving unit 32 provided in the first embodiment (FIG. 1).

The operation of the second embodiment, or the endoscope surgery system shown in FIG. 4, will now be explained.

The CCD (not shown) in the TV adapter 21 receives the light reflected from the medical instrument 6 which is caught in the field of view of the endoscope 5. The CCD converts the light into image signals, which are supplied to the image processor 23. The image processor 23 processes the signals into image data. The image data is supplied to the pattern-matching circuit 42 and the image-moving unit 43.

The pattern-matching circuit 42 converts the image data to binary image data, performs outline-emphasis on the binary image data, and compares the outline-emphasized image data with the image data representing the shape marker 41. It determines that the outline-emphasized image data represents the marker 41 and generates data representing the position of the distal end of the instrument 6. Namely, the circuit 42 detects the position of the distal end of the medical instrument. The data generated by the circuit 42 is supplied to the image-moving unit 43.

The image-moving unit 43 extracts a part of the image data supplied from the image processor 23. The extracted part of the image data is supplied to the TV monitor 31. The TV monitor 31 displays the image of the distal end portion of the instrument 6 in an enlarged size. Thus, the image displayed on the screen of the TV monitor 31 is switched to another, as if the endoscope 5 tracked the distal end of the medical instrument 6.

In the endoscope surgery system shown in FIG. 4, the shape marker 41 is mounted on the distal end portion of the instrument 6, and the pattern-matching circuit 42 process the image data, thereby detecting the position of the distal end of the instrument 6. Therefore, the system is more compact than the first embodiment in which the magnetic sensor 27 is attached on the instrument 6 and connected by a cable to the position-detecting circuit 28. With the system shown in FIG. 4, too, the distal end of the medical instrument 6 can be racked.

The shape marker 41 may be replaced by a color marker. In this case, the pattern-matching circuit 42 is replaced by a color-correlation circuit which is designed to extract data representing the color marker, compares this data with the data representing the color of the marker, and detects the position of the color marker. The position the distal end of the medical instrument 6 assumes can therefore be detected.

A color-extracting position detecting circuit may be used which converts the image signal into a color space (e.g., a YIQ (color-difference signal) space, an HCV space, an HSI space or an L*a*b* space), extracts the color part set in the color space thus obtained may be extracted and calculates the gravity center of the color part. In this case, the position of the distal end of the instrument 6 can be detected if the color of the color marker is set in the color-extracting position detecting circuit, as the color which is to be extracted.

Alternatively, the shape marker 41 may be replaced by a brightness marker. If this is the case, the pattern-matching circuit 42 is replaced by a linear brightness correlation circuit which is designed to extract data representing the brightness marker, compares this data with the brightness of the marker, and detects the position of the brightness marker. The position distal the distal end of the instrument 6 assumes can therefore be detected.

Figures 6A, 6B:
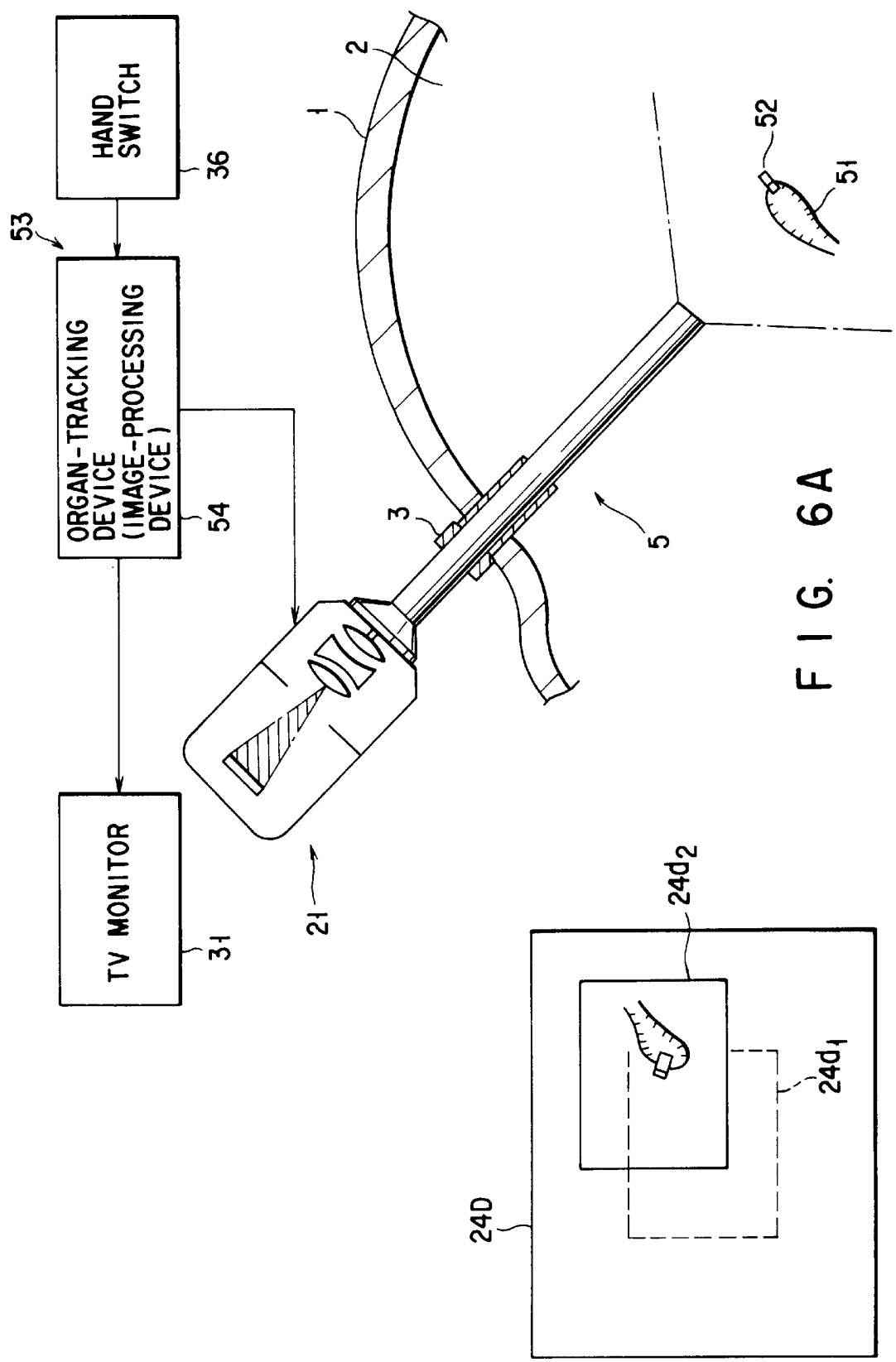
FIG. 6A is a schematic representation of a modification of the second embodiment.
FIG. 6B is a diagram explaining how an image is displayed at the same position on the TV monitor screen incorporated in the modified endoscope surgery system.

FIGS. 6A and 6B illustrate a modification of the second embodiment. FIG. 6A is a schematic representation of the modified endoscope surgery system, and FIG. 6B is a diagram explaining how an image is displayed at the same position on the TV monitor 31.

As shown in FIGS. 6A and 6B, a marker 52, either a shape marker or a color marker, is attached to the objecting organ 51 present in the patient's peritoneal cavity 2, not to the distal end of the medical instrument 6 as in the second embodiment. Thus, the image displayed on the screen of the TV monitor 31 is switched to another, as if the endoscope 5 tracked the marker 52 attached to the organ 51.

As shown in FIG. 6A, the control section 53 of the modified system incorporates an organ-tracking device 54. As in the second embodiment, the image memory 24 (not shown) stores the image data 24D representing the image provided by the endoscope 5. The organ-tracking device 54 extracts that part of the image data 24D which represents the image of the marker 52. Further, the device 54 compares the extracted data with the shape or color of the marker 52, and detects the position of the marker 52. In accordance with the position of the marker 52, thus detected, the device 54 processes the image data 24D such that the image of the organ 51 is displayed in the center part of the screen of the TV monitor 31.

While the organ-tracking device 54 is tracking the marker 52 on the specified organ 51, the image $24d_1$ represented by the extracted part of the image data 24D is switched to an image $24d_2$ by electronic means, as is illustrated in FIG. 6B. The image provided by the endoscope 5 can be automatically switched, without using a medical instrument 6.

FIG. 7A shows an HMD (Head Mounting Display) 63 for use in the second embodiment, in place of the TV monitor 31, and a position detector for detecting the position of the HMD. The position detector comprises a sense coil 64 and a source coil 65. The sense coil 64 is secured to the HMD 63 placed on the head 62 of the surgeon 61. Alternatively, the sense coil 64 may be held on the surgeon's head 62 by means of a headband. The source coil 65 is held at a specific position in the endoscope surgery system.

The sense coil 64 and the source coil 65 have three coil elements each, which are wound around three axes (X axis, Y axis, and Z axis) intersecting at right angles to one another. A position sensor (not shown) is provided to determine the positional relationship between the coils 64 and 65 from the mutual inductance of the coils 64 and 65. The position sensor outputs a control signal which represents the position of the surgeon's head 62.

The modified endoscope surgery system incorporating the HMD 63 comprises an image control device (not shown). The image control device is designed to electronically process the extracted part of the image data 24D stored in the image memory 24 in accordance with the control signal output from the position sensor. As the extracted part of the data 24D is so processed, the image represented by the extracted part is moved and switched to another on the screen of the HMD 63.

While seeing the image displayed on the HMD 63, the surgeon 61 may nod or turn his or her head to look at an object which is not displayed and which he or she needs to examine. Then, the HMD 63 displays the image of the object on its screen. The image on the screen is magnified as the surgeon 61 moves his or her head forward. The image is reduced as the surgeon 61 moves the head backward.

As mentioned above, the image provided by the endoscope 5 and displayed on the screen of the HMD 63 is switched in accordance with the control signal representing the position of the surgeon's head 62. In other words, the image is automatically switched as the surgeon 61 moves his or her head. The switching of the image does not interfere with the surgeon's manipulating of a medical instrument at all. The modified system incorporating the HMD 63 can therefore help the surgeon 61 to perform surgery with high efficiency.

In the second embodiment (FIG. 4), the hand switch 36 may be replaced by a remote-control panel 71 illustrated in FIG. 7B. The panel 71 is attached to the operation section of the instrument 6, the floor of the operating room, or a side of the operating bed.

As shown in FIG. 7B, the remote-control panel 71 has two sets of buttons. The first set consists of an up-button 72a, a down-button 72b, a left-button 72c, and a right-button 72d. The surgeon may push these buttons 72a, 72b, 72c and 72c to move the image upwards, downwards, leftward and rightward on the screen of the TV monitor 31. The second set consists of an image-enlarging button 73a and an image-reducing button 73b. The surgeon may push these buttons 73a and 73b to drive the zoom lens built in the endoscope 5, thereby to enlarge and reduce the image displayed on the screen of the TV monitor 31.

As the surgeon operates the buttons 72a to 72d and buttons 73a and 73b, all on the remote-control panel 71, the image displayed by the TV monitor 31 is moved and enlarged or reduced by electronic means. The process of moving, enlarging or reducing the image does not interfere with the surgeon's manipulating of the medical instrument 6 at all. The remote-control panel 71 helps the surgeon to perform surgery with high efficiency.

In the second embodiment (FIG. 4), the hand switch 36 may be replaced by a joy stick 81 of the type shown in FIG. 7C. The joy stick 81 is attached to the operation section of the instrument 6, the floor of the operating room, or a side of the operating bed.

As shown in FIG. 7C, the joy stick 81 comprises an operation panel 82 and a rod 83 protruding upwards from the center part of the panel 82. Four position labels 84a to 84d are put on the panel 82, indicating upward, downward, leftward and rightward directions, respectively. The rod 83 can be inclined to the position labels 84a to 84d. It can also be pulled in the direction of arrow T and pushed in the direction of arrow W. The surgeon may incline the rod 83 to the labels 84a, 84b, 84c and 84d to move the image upwards, downwards, leftward and rightward on the screen of the TV monitor 31. Furthermore, the surgeon pull and push the rod 83 to drive the zoom lens built in the endoscope 5, thereby to enlarge and reduce the image displayed on the screen of the TV monitor 31.

As the surgeon inclines, pulls or push the rod 83, the image displayed by the TV monitor 31 is moved and enlarged or reduced by electronic means. The process of moving, enlarging or reducing the image does not interfere with the surgeon's manipulating of the medical instrument 6 at all. The joy stick 81 assists the surgeon in enhancing the surgery efficiency.

Figure 8:
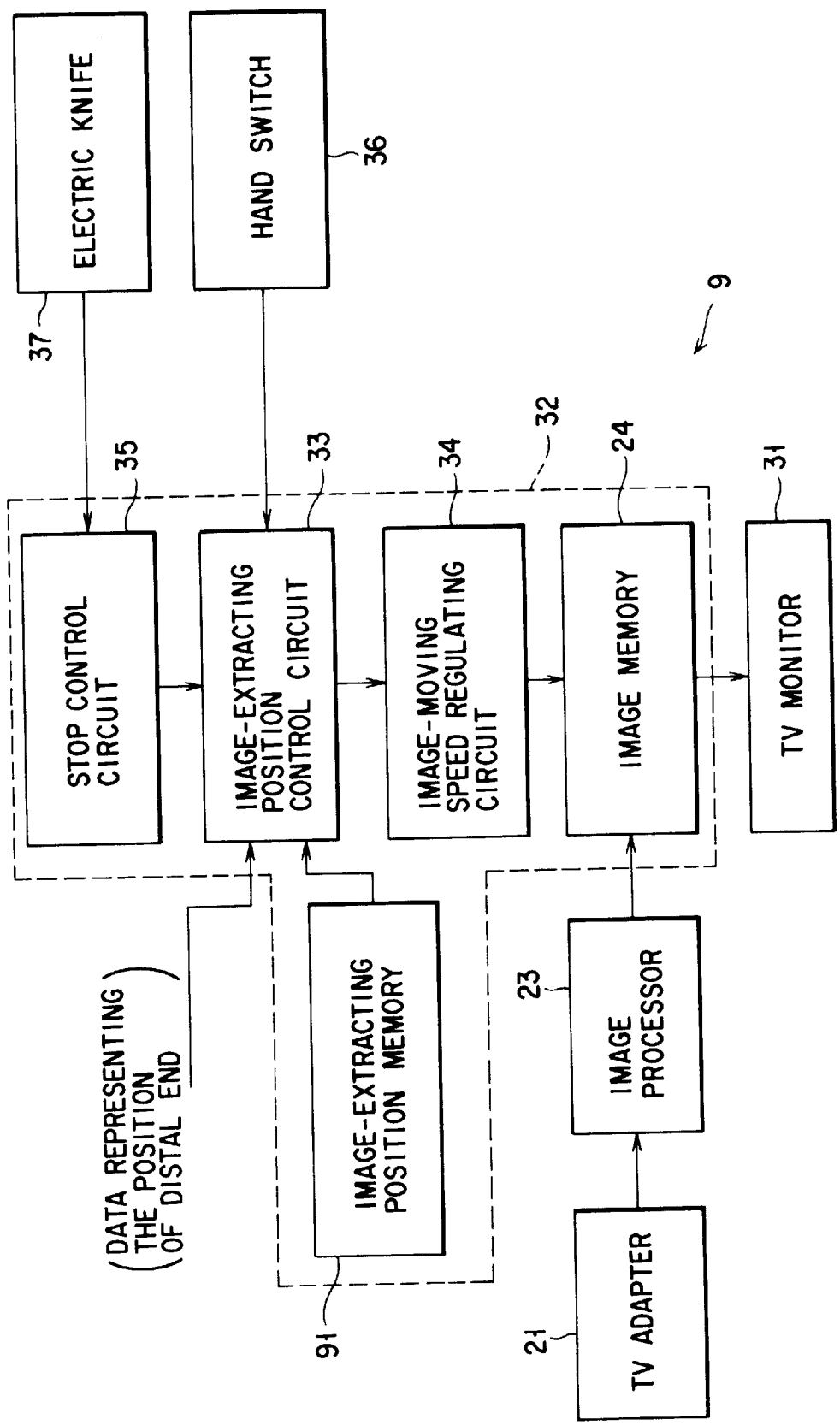
FIG. 8 is a block diagram of the control section incorporated in an endoscope surgery system according to a third embodiment of the present invention.

Still another endoscope surgery system, which is the third embodiment of the present invention, will be described with reference to FIG. 8. FIG. 8 is a block diagram of the control section incorporated in the third embodiment.

The third embodiment is identical to the first embodiment (FIGS. 1 to 3), except that an image-extracting position memory 91 is provided in the image-moving unit 32 of the control section 9.

The image-extracting position memory 91 stores the reference image-extracting position data designating that part of image data 24D which is to be initially extracted from the image memory 24. Every time the hand switch 36 is turned on during the operation of the endoscope surgery system, the reference image-extracting position data stored in the image-extracting position memory 91 is input to the image-extracting position control circuit 33. As a result, the image represented by the extracted part of the image data 24D stored in the image memory 24 is moved on the screen of the TV monitor 31, as if the distal end portion of the instrument 6 were tracked.

The operation of the third embodiment, or the endoscope surgery system shown in FIG. 8, will now be explained.

Seeing the image provided by the endoscope 5 and displayed by the TV monitor 31, the surgeon operates a key pad (not shown), generating the reference position data which represents the position of the distal end of the instrument 6. Then, the surgeon clicks the hand switch 36, whereby the reference position data is thereby stored into the image-extracting position memory 91. The reference position data will be used as the reference image-extracting position data.

Whenever the surgeon moves the medical instrument 6, bringing the distal end thereof to a desired position in the patient's peritoneal cavity, he or she clicks the hand switch 36. The moment the hand switch 36 is clicked, the image-extracting position control circuit 33 generates a control signal, which is supplied to the image-moving speed regulating circuit 34. Then, the circuit 34 fetches the reference image-extracting position data from the memory 91 and supplies this data to the image memory 24 through the image-moving speed regulating circuit 34. As a result of this, the image of the distal end portion of the instrument 6 is moved on the screen of the TV monitor 31, to the reference position which is represented by the reference position data (or the reference image-extracting position data).

The reference position may be set at the center part of the screen of the TV monitor 31. If it is so set, the image-moving unit 32 will operate to display the image of the distal end of the instrument 6 will be displayed at the center part of the TV monitor screen. Except for this respect, the third embodiment operates in the same way as the first and second embodiments.

The third embodiment is advantageous in that the image of the distal end of the instrument 6 is automatically moved to the preset reference position on the screen of the TV monitor 31 the moment the surgeon turns on the hand switch 36. Therefore, this embodiment is an endoscope surgery system which displays the distal end of the medical instrument 6 at the reference position on the TV monitor screen as if the distal end were tracked.

Figure 9:
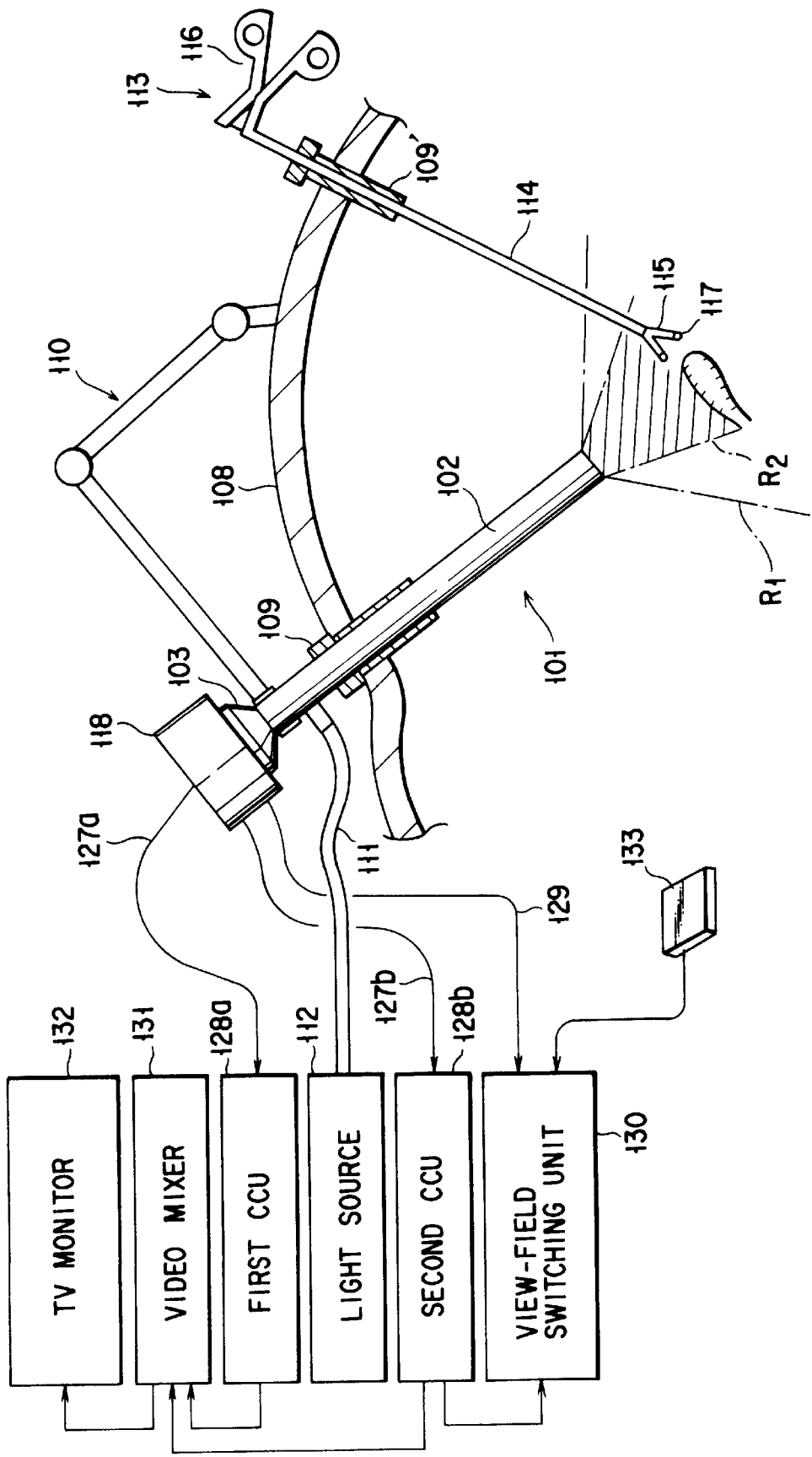
FIG. 9 is a schematic diagram illustrating a endoscope surgery system according to a fourth embodiment of the invention.

A further endoscope surgery system, which is the fourth embodiment of the invention, will be described with reference to FIGS. 9 to 11. FIG. 9 is a schematic diagram illustrating this endoscope surgery system. FIG. 10A shows the TV camera unit 118 incorporated in this embodiment.

As FIG. 9 shows, the fourth embodiment has a rigid scope 101 of direct-view type, such as a laparoscope. The rigid scope 101 comprises an insertion section 102 and an ocular section 103. As shown in FIG. 10A, the insertion section 102 contains an objective lens 104 in its distal end, and the ocular section 103 contains an ocular lens 105. The barrel 106 of the insertion section 102 contains a plurality of relay lenses 107. The relay lenses 107 are located between the objective lens 104 and they ocular lens 105. They are spaced apart from one another. The optical system of the rigid scope 101 further includes a distortion-compensating lens (not shown).

As seen from FIG. 9, a trocar 109 is set in an opening incised in the abdominal wall 108 of a patient. The insertion section 102 of the rigid scope 101 is inserted through the trocar 109 into the peritoneal cavity of the patient. The proximal portion of the insertion section 102 is movably held by a scope holder 110 which is a multi-joint structure.

The insertion section 102 of the rigid scope 101 incorporates a light guide fiber (not shown) for applying illumination light to the distal end of the insertion section 102. Connected to the light guide is one end of alight guide cable 111. The other end of the cable 111 is connected to a light source 112 located outside the rigid scope 101.

As shown in FIG. 9, another trocar 109' is set in an opening incised in the abdominal wall 108, spaced apart from the first trocar 109. A pair of forceps 113, which is a medical instrument, is inserted through the second trocar 109' into the patient's peritoneal cavity. The forceps 113 comprises an insertion section 114, a pair of tongs 115, and a handle 116. Tongs 115 are connected to the distal end of the insertion section 114. The handle 116 is connected to the proximal end of the insertion section 114. When the handle 116 is opened and closed, the tongs 115 are opened and closed by remote control.

A color marker 117 is adhered to one of the tongs 115, enabling the surgeon to recognize the position of the tongs 115 easily. The color marker 117 is biologically adapted paint. The marker 117 is of a color quite different from those of the organs, such as green, yellow or the like. The forces 113 may be replaced by any other medical instrument such as ablation forceps, scissors, a laser probe, a suturing device, an electric knife, a stylus holder, and an ultrasonic suction device.

The TV camera unit 118 is removably attached to the ocular section 103 of the rigid scope 101. The TV camera unit 118 is designed to generate image signals from the light supplied from the light supplied from the rigid scope 101. As shown in FIG. 10A, the unit 118 comprises a casing 119, a half mirror 120, a magnifying optical system 121, and a wide-angle optical system 122. The mirror 120 and both optical systems 121 and 122 are contained in the casing 119. The half mirror 120 opposes the ocular lens 105 provided in the ocular section 103 of the rigid scope 101 and is spaced apart from the ocular lens 105. The half mirror 120 splits an optical image supplied from the ocular section 103 into two images. The first image passes through the half mirror 120 and is supplied to the magnifying optical system 121, while the second image is reflected by the half mirror 120 is supplied to the wide-angle optical system 122. The half mirror 120 can be replaced by an optical reflector such as a prism.

As illustrated in FIG. 10A, the magnifying optical system 121 comprises a zoom lens 123, a focusing lens 124, and a single-plate CCD (first CCD) 125a having a mosaic filter. The wide-angle optical system 122 comprises a focusing lens 126 and a single-plate CCD (second CCD) 125b having a mosaic filter. The CCD 125a of the magnifying optical system 121 is mounted on an X-Y stage (not shown) which can move in a horizontal plane, along X axis and Y which intersect with each other at right angles. The X-Y stage is driven by an actuator (not shown, either) such as a DC servo motor, a stepping motor, a voice-coil motor, or the like. The zoom lens 123 of the magnifying optical system 121 is driven by an actuator (not shown), which may be a DC servo motor, a stepping motor, a voice-coil motor, or the like.

As shown in FIG. 9, the TV camera unit 118 is connected by video-signal cables 127a and 127b to two CCUs (Camera Control Units) 128a and 128b. The unit 118 is also connected by a control-signal cable 129 to a view-field switching unit 130. The CCU 125a incorporated in the magnifying optical system 121 is connected to the first CCU 128a by the video-signal cable 127a. The CCD 125b provided in the wide-angle optical system 122 is connected by the video-signal cable 127b to the second CCU 128b. The actuator for driving the X-Y stage and the actuator for driving the zoom lens, both incorporated in the TV camera unit 118, are connected to the view-field switching unit 130 by the control-signal cable 129.

The CCUs 128a and 128b are connected to a video mixer 131 provided outside the rigid scope 101. The vide mixer 131 is connected to a TV monitor 132. The second CCU 128b is also connected to the view-field switching unit 130. Connected to the unit 130 is a foot switch unit 133, which has a tracking switch and a zooming switch (either not shown).

FIG. 11 is a block diagram of the view-field switching unit 130. As can be understood from FIG. 11, the unit 130 comprises a color-space converter 134, an extracted-image forming device 135, a gravity center calculator 136, a position-designating device 137, an X-Y stage controller 138, and a zooming controller 139. The color-space converter 134 is connected to the second CCU 128b to received a signal supplied therefrom. The extracted-image forming device 135 is connected to the converter 134 to receive a signal supplied therefrom. The gravity center calculator 136 is connected to the device 135 for receiving a signal supplied therefrom.

The position-designating device 137 is connected to the gravity center calculator 136, foot switch 133, the X-Y stage controller 138, and the zooming controller 139. The foot switch 133 is connected to the zooming controller 139. The position-designating device 137 can receive signals output by the foot switch 133 and the gravity center calculator 136 and zooming controller 139.

The actuator for driving the X-Y stage provided in the TV camera unit 118 is connected to the X-Y stage controller 138. A control signal generated by the controller 138 is input to the actuator for driving the X-Y stage. The actuator for driving the zoom lens provided in the TV camera unit 118 is connected to the zooming controller 139. A signal generated by the foot switch 133 is supplied to the zooming controller 139. A control signal generated by the zooming controller 139 is input to the position-designating device 237 and the actuator for driving the zoom lens.

Figure 25:
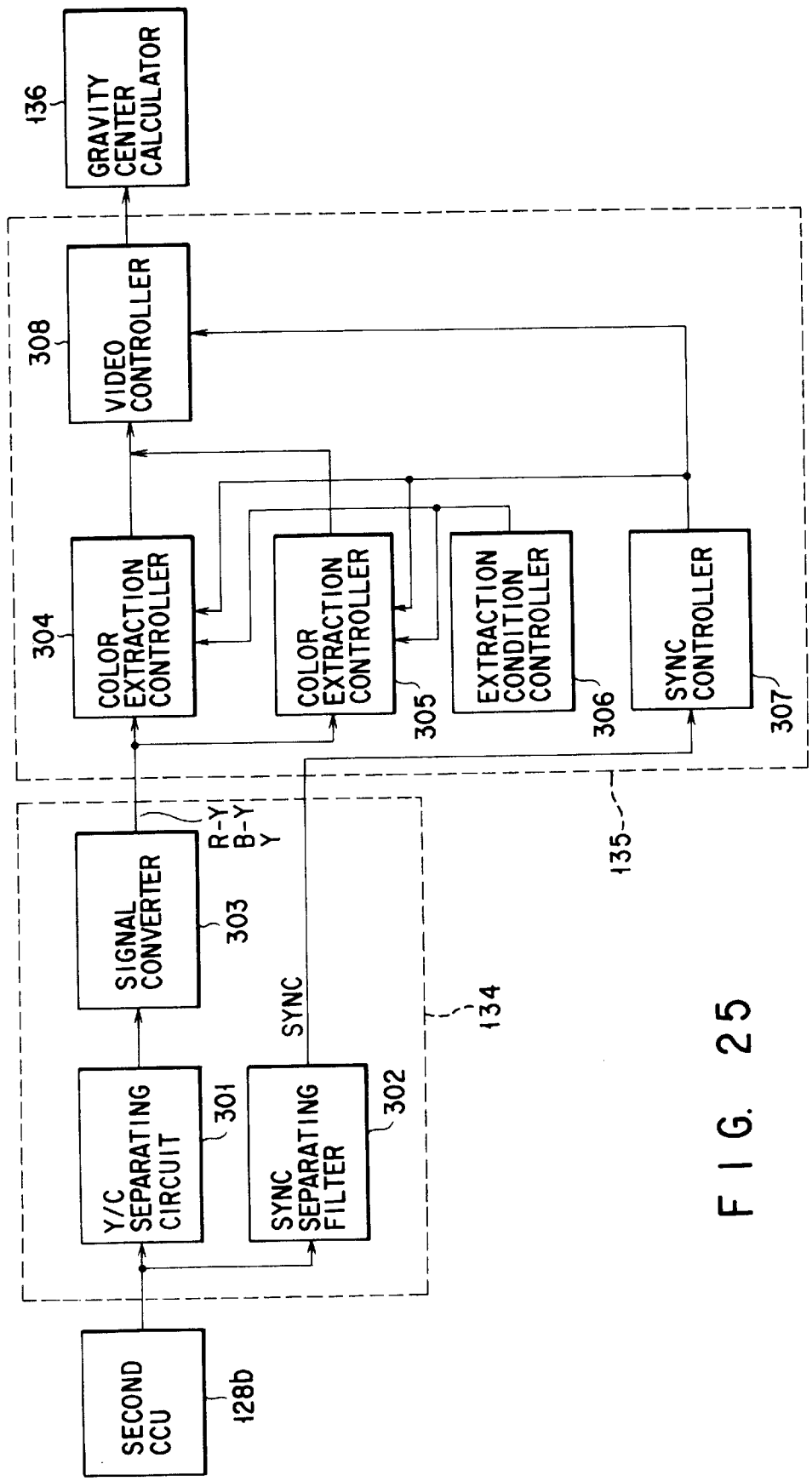
FIG. 25 is a block diagram of a color-space converter and an extracted-image forming device of the view-field switching unit according to the fourth embodiment.

As shown in FIG. 25, the color-space converter 134 comprises a Y/C separating circuit 301, a sync separating filter 302, and a signal converter 303. The extracted-image forming device 135 comprises two color extraction controllers 304 and 305, an extraction condition controller 306, a sync controller 307, and a video controller 308.

The Y/C separating circuit 301 and the sync separating filter 302 have their inputs connected to the second CCU 128b, to receive the NTSC video signal generated by the CCU 128b. The Y/C separating circuit 301 separates the NTSC video signal to a luminance signal (Y) and a chrominance signal (C). The output of the Y/C separating circuit 301 is connected at its output to the input of the signal converter 303, to supply the luminance signal (Y) and the chrominance signal (C) to the converter 303. The converter 303 converts these signals to color-difference signals R-Y, B-Y, and Y.

The output of the signal converter 303 is connected to the color extraction controllers 304 and 305, both incorporated in the extracted-image forming device 135. Thus, the output signals of the signal converter 303, i.e., the color-difference signals R-Y, B-Y, and Y are supplied to both color extraction controllers 304 and 305.

The sync separating filter 302, which is provided in the color-space converter 134, is designed to separate a horizontal sync signal Hsync and a vertical sync signal Vsync from the NTSC video signal. The filter 302 has its output connected to the input of the sync controller 307 incorporated in the extracted-image forming device 135. The output of the sync controller 307 is connected to the inputs of both color extraction controllers 304 and 305 and also to the input of the video controller 308.

The extraction condition controller 306 has its output connected to the inputs of the color extraction controllers 304 and 305. The controller 306 generates data items R-Ymin/max, B-Ymin/max and Ymin/max representing color extraction conditions. These data items are input to the color extraction controllers 304 and 305. The first color extraction controller 304 generates a binary signal from the color-difference signals R-Y, B-Y and Y in accordance with the horizontal sync signal Hsync and vertical sync signal Vsync supplied from the sync controller 307. So does the second color extraction controller 305. The binary signal generated by either color extraction controller consists of "0" bits and "1" bits. The "0" bits represent those portions of the signals R-Y, B-Y and Y which meet the color extraction conditions (R-Ymin/max, B-Ymin/max and Ymin/max), and the "1" bits represent those portions of the signals R-Y, B-Y and Y which do not meet the conditions R-Ymin/max, B-Ymin/max and Ymin/max. (This may be other way around.)

The color extraction controllers 304 and 305 have their outputs connected to the input of the video controller 308. The output of the video controller 308 is connected to the input of the gravity center calculator 136. The video controller 308 superposes the binary signals output from the color extraction controllers 304 and 305, producing a signal which represents an extracted color. This signal is input to the gravity center calculator 136. Two different set of color extractions may be set in the controllers 304 and 305, making it possible to extract two colors simultaneously. The greater the number of color extraction controllers provided, the more colors can be extracted at the same time.

The operation of the fourth embodiment, or the endoscope surgery system shown in FIG. 9, will now be explained.

At first, the surgeon inserts the insertion section 102 of the rigid scope 101 held by the scope holder 110 is inserted into the patient's peritoneal cavity through the first trocar 109 set in the opening incised in the abdominal wall 108, as illustrated in FIG. 9. Next, the surgeon inserts the forceps 113 into the peritoneal cavity through the second trocar 109' set in the opening incised in the abdominal wall 108. As shown in FIG. 9, the forceps 113 is positioned such that its tongs 115 is located within the view field $R_1$ of the wide-angle optical system 121.

An optical image of the objects in the view field $R_1$ is supplied through the rigid scope 101 to the TV camera unit 118 connected to the ocular section 103 of the unit 118. In the TV camera unit 118, the half mirror 120 spits the optical image into two. The first image passing through the half mirror 120 is supplied to the magnifying optical system 121, and the second image reflected by the half mirror 120 is supplied to the wide-angle optical system 122.

In the wide-angle optical system 122, an image having the same size as the image focused by the objective lens 104 of the rigid scope 101 is formed on the light-receiving surface of the second CCD 125b. Thus, a larger image will be formed on the second CCD 125b if the objective lens 104 is replaced by a wide-angle lens. The second CCD 125b converts the second image into an electric signal, which is supplied to the second CCU 128b. The second CCU 128b generates a video signal from the electric signal. The video signal is input from the second CCU 128b to the color-space converter 134 and the video mixer 131 which are incorporated in the view-field switching unit 130.

The color-space converter 134 extracts color components for pixels from the video signal and converts each color component to color-space data (i.e., color difference, HSI, L*a*b*, and the like). If the video signal has NTSC format, the converter 134 generates color-difference signals (Y, B-Y, R-Y) from a Y signal, an $E_Q$ signal and an $E_I$ signal. Further, the converter 134 generates a color space having three stimulus values (X, Y, Z), such as an HSI (Hue, Saturation, Intensity) space or an L*a*b* space, from an RGB signal obtained from the color-difference signals. If the video has RGB format, the converter 134 generates color-difference signals and a color space, such as an HSI space or an L*a*b* space, in the same way.

The color-difference signals and the color space are input to the extracted-image forming device 135. The device 135 determines whether or not each input color-space signal represents a pixel color which falls within a preset color range. If the color-space signal represents a pixel color falling with the color range, the device 135 imparts intensity 0 to the color-space signal. Otherwise, the device 135 imparts intensity 1 to the color-space signal. In either case, each color-space signal is not saturated and output from the extracted-image forming device 135. Therefore, the device 135 outputs binary image data which consists of "0" bits representing black pixels and "1" bits representing white pixels. The values of the bits may be inverted so that each "0" bit represents a white pixel, while each "1" bits represents a black pixel.

The binary image data output from the extracted-image forming device 135 is supplied to the gravity center calculator 136. The gravity center calculator 136 calculates the center of the black portion of the image represented by the binary image data. The calculator 136 generates pixel data representing the coordinates of the black pixel located at the center of the black portion of that image. The pixel data is input to the position-designating device 137.

The position-designating device 137 obtains the difference between the coordinates of the black pixel and the coordinates of a point at which this black pixel should be displayed on the TV monitor 132, for example the very center of the TV monitor screen. The difference, thus obtained, is supplied as an image-moving signal to the X-Y stage controller 138 when the image-tracking button (not shown) mounted on the foot switch 133 is pushed. Upon receipt of the image-moving signal, the controller 138 generates and supplies a control signal to the actuator for driving the X-Y stage provided in the TV camera unit 118.

The actuator drives the X-Y stage, whereby the first CCD 125a of the magnifying optical system 121 is moved along the X and the Y axes, for the distances represented by the image-moving signal which the position-designating device 137 has generated. As a result, the black pixel located at the center of the black portion of that image is displayed at the center of the screen of the TV monitor 132.

The optical image supplied to the magnifying optical system 121 from the half mirror 120 passes through the zooming lens 123 and is focused on the first CCD 125a by the focusing lens 124. The zooming lens 123 magnifies the intra-cavity image. The image magnified is supplied to the ocular lens 105. Hence, only a part of the magnified image is formed on the first CCD 125a, and the surgeon can see an enlarged image of the objects represent in the peritoneal cavity.

As described above, the color marker 117 is adhered to one of the tongs 115 of the forceps 113 and is of a color quite different from those of the organs. If this color of the marker 117 may be designated as one to be extracted and if the tongs 115 are to be displayed at the center of the screen of the TV monitor 132, the forceps 113 is tracked as will be explained with reference to FIG. 10B.

The image of the tissue to be treated may be displayed in an edge part of the view field $R_2$ of the magnifying optical system 121 as shown in FIG. 10B, though the color marker 117 on one of the tongs 115 is within the view field $R_1$ of the wide-angle optical system 122 of the rigid scope 101. In this case, it is difficult for the surgeon to treat the tissue, while observing the image of the tissue and the image of the forceps 115, both displayed on the TV monitor screen. To have the tissue displayed at the center of the view field $R_2$, the surgeon moves the forceps 113 to the tissue and clamps the tissue with the tongs 115, and then turns on the image-tracking button on the foot switch 133. The position-designating device 137 generates an image-moving signal, which is input to the X-Y stage controller 138. The controller 138 generates a control signal, which is supplied to the actuator for driving the X-Y stage. The actuator drives the X-Y stage, and the first CCD 125a is moved along the X and the Y axes, whereby the forceps 113 and the tissue are displayed at the center of the view field $R_2$ as illustrated in FIG. 10B. In other words, the view field has been moved on the screen of the TV monitor 132 to, so to speak, track the distal end of the forceps 113.

When a zooming switch (not shown) provided on the foot switch 133 is turned on, the zooming controller 139 generates a control signal, which is supplied to the actuator (not shown) incorporated in the TV camera unit 118. The actuator moves the zooming lens 123 along the optical axis of the first CCD 125a for the distance represented by the control signal. This distance is detected by an encoder (not shown) or a potentiometer (not shown) attached to the actuator. The zooming controller 139 generates a signal representing the distance and supplies it to the position-designating device 137.

The position-designating device 137 calculates a linear weight from the distance for which the zooming lens 123 has been moved to change the zooming ratio. The device 137 applies the linear weight to the image-moving signal which is to be input to the X-Y stage controller 138. The image-moving signal, thus linearly weighted, is input to the X-Y stage controller 138. In accordance with the linearly weighted image-moving signal, the controller 138 controls the actuator. The actuator drives the X-Y stage at such a speed that the images of the forceps 113 and the tissue are moved on the TV monitor screen at the same speed despite the change in the zooming ratio.

Instead of one color marker 117, two or more markers of different colors may be adhered to the tongs 115 of two or more forceps, respectively, which are inserted in the peritoneal cavity. If this is the case, the tongs of any forceps selected can be tracked and caught in the view field $R_2$ of the magnifying optical system 121 by designating that one of the colors preset in the view-field switching unit 130 which is the color of the marker adhered to one of the tongs of the selected forceps.

The video mixer 131 receives the signals output from the first CCU 128a and the second CCU 128b. From these signals the video mixer 131 generates two image data items which respectively represent the magnified image formed by the first CCD 125a and the wide-angle image formed by the second CCD 125b. These image data items are supplied to the TV monitor 132. The TV monitor 132 displays the magnified image and the wide-angle image simultaneously. Alternatively, it displays either the magnified image or the wide-angle image. It should be noted that the magnified image is of the objects of interest, whereas the wide-angle image is of the objects of interest and other objects located near the objects of interest.

The fourth embodiment (FIG. 9) is advantageous in the following respects.

First, the objects of interest are displayed in an enlarged size, along with the wide-angle image of these objects and adjacent objects, since the TV camera unit 118 removably attached to the ocular section 103 of the rigid scope 101 has the magnifying optical system 121 and the wide-angle optical system 122.

Further, the magnified image of the objects of interest, formed by the first CCD 125a, can be quickly moved on the screen of the TV monitor 132 as the surgeon moves the forceps 113, since the view-field switching unit 130 switches the view field of the first CCD 125a to track the color marker 117 on one of the tongs 115 of the forceps 113 being moved. To switch the view field it is not necessary for the surgeon's assistant to move the rigid scope 101 as in the conventional endoscope surgery system. The magnified image of the objects of interest can, therefore, be moved easily and fast to the desired position on the screen of the TV monitor 132.

Moreover, the magnified image formed by the first CCD 125a can be moved on the TV monitor screen, without using an electrically driven manipulator which is indispensable in the conventional endoscope surgery system. The fourth embodiment can therefore be simple in structure as a whole.

Furthermore, since the wide-angle image formed by the second CCD 125b is much larger than the magnified image of the tongs 115 and the tissue being treated, which is formed by the first CCD 125a, the surgeon can quickly grasp the positional relation the tongs 115 and the tissue have with respect to the objects located near the tongs 115 and the tissue. Thus, the surgeon can easily determine whether it is necessary or not to push the image-tracking button on the foot switch 133 to move the images of the tongs 115 and the tissue to the center of the TV monitor screen.

In the fourth embodiment, the position at which the magnified image of the objects of interest is not limited to the center of the TV monitor screen. Rather, this position can be switched, if necessary. Further, the single-plate CCDs 125a and 125b may be replaced by three-plate CCDs, each having three plates for forming a red image, a green image and a blue image, respectively. Still further, the first CCD 125a may be removed from the magnifying optical system 121, and the focusing lens 124 may be attached to the X-Y stage, thereby to switch the view field of the magnifying optical system 121. The position which the distal ends of the tongs 115 assume on the TV monitor screen may be detected by means of pattern matching in which the shape (i.e., outline of the distal end of the forceps 113) is extracted from the image data, or by means of this pattern matching and the above-mentioned method of extracting data representing the color marker 117.

Furthermore, the color marker 117 may be a label which is removably attached to one of the tongs 115. The foot switch 133 may be replaced by a hand switch removably mounted on the handle 116 of the forceps 113, for switching the view field and varying the zooming ratio.

A modification of the view-field switching unit 130 according to the fourth embodiment of the present invention will be described, with reference to FIG. 26.

As in the fourth embodiment, the view-field switching unit 130 has a the color-space converter 134 and an extracted-image forming device 135. As shown in FIG. 26, the color-space converter 134 comprises an NTSC decoder 311, an A/D converter 312, and a look-up table 313. The extracted-image forming device 135 comprises a distance calculator 314, an extracted color memory 315, a comparator 316, and a sensitivity memory 317.

In the color-space converter 134, the NTSC decoder 311 has its input connected to the output of the second CCU 128b, to receive an NTSC video signal from the second CCU 128b. The NTSC decoder 311 converts the NTSC video signal to an RGB signal. The NTSC decoder 311 has its output connected to the input of the A/D converter 312. The A/D converter 312 converts the RGB signal to a digital RGB signal.

The output of the A/D converter 312 is connected to the input of the look-up table 313. The look-up table 313 is comprised of a ROM or a RAM. It converts the digital RGB signal to HSI (Hue, Saturation, Intensity) color space data. An uniform color space, such as UCS, L*a*b* or L*u*v* can be set in this HSI color space data. The look-up table 313 has its output connected to the extracted-image forming device 135, more precisely to the input of the distance calculator 314.

In the extracted-image forming device 135, the output of the extracted color memory 315 is connected to the input of the distance calculator 314. The color space data generated by the look-up table 313 is supplied to the distance calculator 314. The extracted color data stored in the memory 315 is also supplied to the distance calculator 314. The calculator 314 finds the difference between the color space data output from the look-up table 313 and the extracted color data stored in the memory 315, thereby calculating a color space distance, and generates data representing the color space distance.

The distance calculator 314 has its output connected to the input of the comparator 316. Also connected to the input of the comparator 316 is the output of the sensitivity memory 317. The color space distance data is input to the comparator 316. At the same time, the color-extracting sensitivity stored in the memory 317 is input to the comparator 316. The Comparator 316 compares the distance calculated by the calculator 314 with the sensitivity stored in the memory 317. The comparator 316 generates a "0" bit when the distance is less than the sensitivity and a "1" bit when the distance is equal to or greater than the sensitivity, or vice versa. Thus, the comparator 316 produces a binary signal representing an extracted color.

The comparator 316 has its output connected to the input of the gravity center calculator 136. The binary extracted color signal produced by the comparator 316 is therefore supplied to the gravity center calculator 136.

The second CCU 128b may be one which can generate an RGB signal. If this is the case, the RGB signal can be directly supplied to the A/D converter 312, and the NTSC decoder 311 need not be provided in the color-space converter 134.

Figure 21:
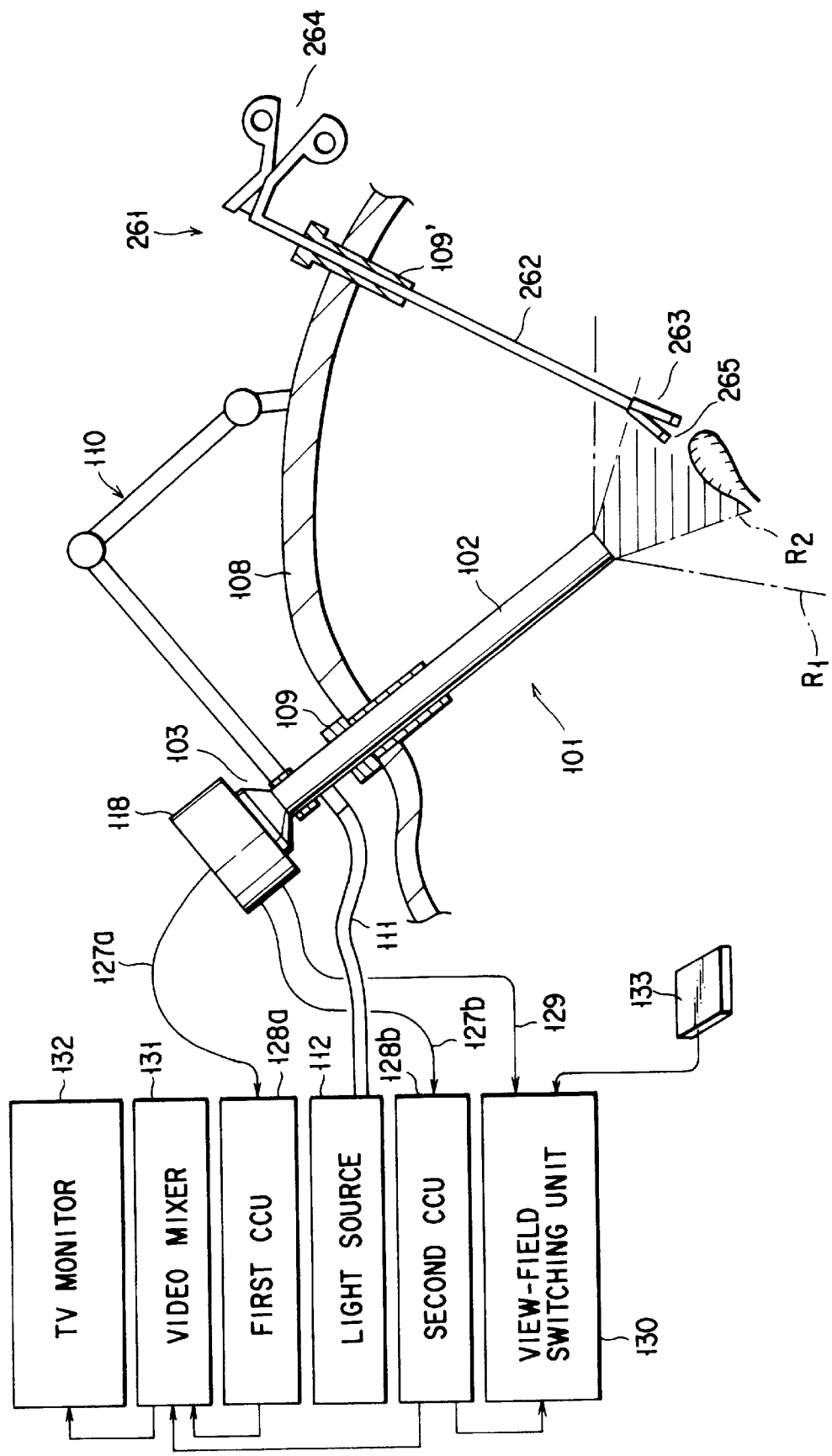
FIG. 21 is a diagram illustrating an endoscope surgery system according to a first modification of the fourth embodiment.

A further endoscope surgery system, which is a first modification of the fourth embodiment, will be described with reference to FIG. 21.

The first modification is modified of the fourth embodiment shown in FIGS. 9, 10A, 10B and 11, and incorporates a suturing device 261, instead of the holding forceps 113 (FIG. 9). As shown in FIG. 21, the suturing device 261 has its insertion section 262 inserted into the peritoneal cavity through the second trocar 109' set in an opening incised in the abdominal wall 108.

Suturing tongs 263 are attached to the distal end of insertion section 262. A handle 264 is connected to the proximal end of the insertion section 262. When the handle 264 is opened and closed, the suturing tongs 263 are opened and closed to suture a tissue present in the peritoneal cavity.

A color marker 265 is provided on the tip of one of the suturing tongs 261. The color marker 117 is formed by coating biologically adapted paint or consists of a layer of such paint and a transparent layer covering the paint layer. As the surgeon moves the suturing device 261, the view-field switching unit 130 switches the view field of the first CCD 125a to track the color marker 265 on one of the suturing tongs 263 of the forceps 261. The magnified image of the tongs 263 is therefore displayed on the screen of the TV monitor 132. Thus, the first modification can achieve the same advantages as the fourth embodiment.

An endoscope surgery system according to a second modification of the fourth embodiment of the invention will be described, with reference to FIG. 22.

The second modification is another modification of the fourth embodiment shown in FIGS. 9, 10A, 10B and 11, and incorporates an electric knife 271, instead of the holding forceps 113 (FIG. 9). The electric knife 271 comprises an insertion section 272, a hook-shaped electrode 273, a grip 274, a lead line 275, and an operation section 276.

Figure 22:
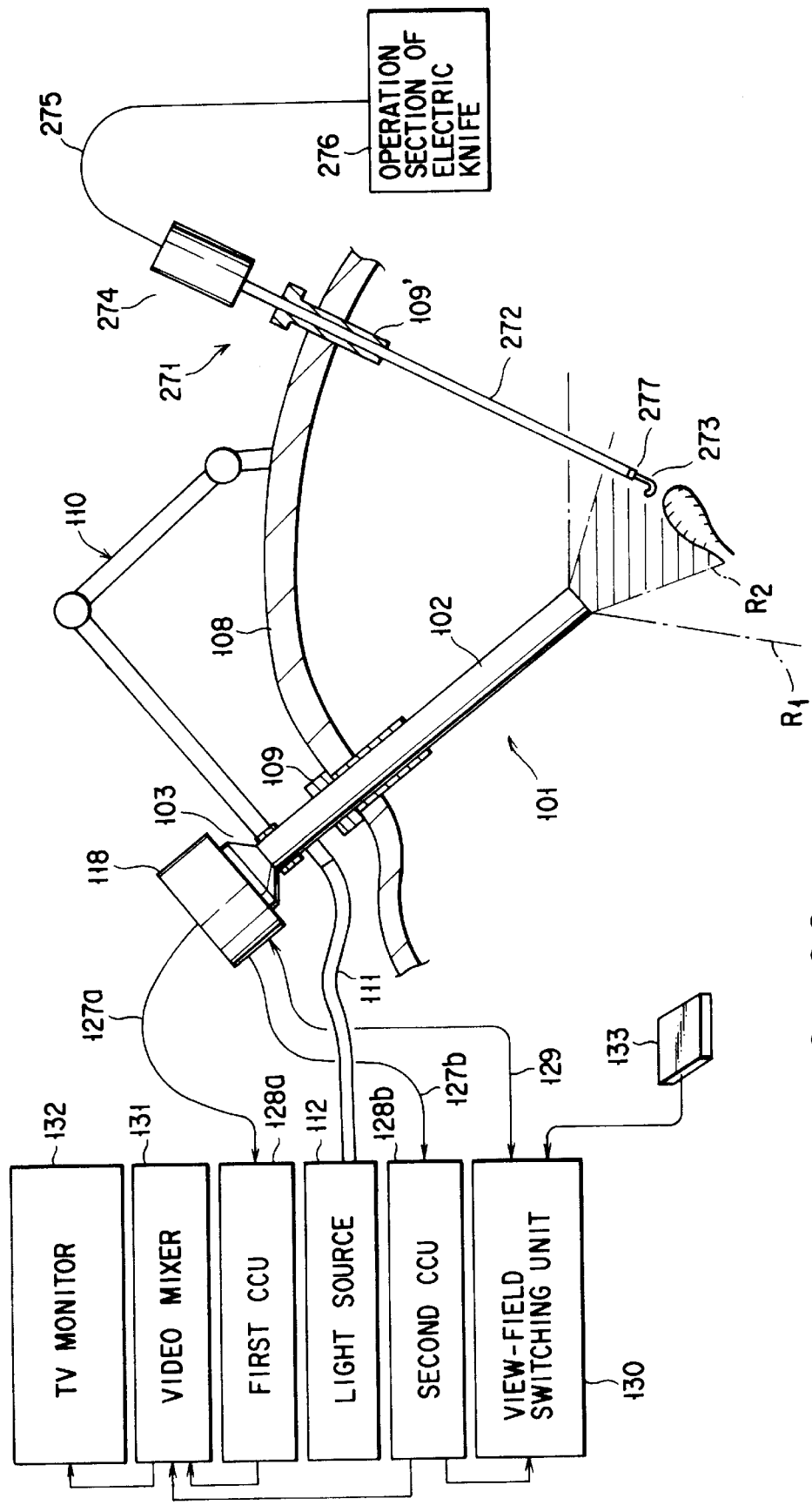
FIG. 22 is a diagram showing an endoscope surgery system according to a second modification of the fourth embodiment.

As shown in FIG. 22, the insertion section 272 is inserted into the peritoneal cavity through the second trocar 109' set in an opening incised in the abdominal wall 108. The hook-shaped electrode 273 is attached to the distal end of insertion section 272. The grip 274 is connected to the proximal end of the insertion section 272. The lead line 275 is connected at one end to the grip 274 and at the other end to the operation section 276.

A color marker 277 of the same type used in the first modification is provided on the tip of hook-shaped electrode 273. As the surgeon moves the electrode 273, the view-field switching unit 130 switches the view field of the first CCD 125a to track the color marker 277 provided on the electrode 273. The magnified image of the electrode 273 is displayed on the screen of the TV monitor 132. Thus, the second modification can attain the same advantages as the fourth embodiment.

Another endoscope surgery system, which is a third modification of the fourth embodiment of the invention will be described with reference to FIG. 23.

The third modification is another modification of the fourth embodiment shown in FIGS. 9, 10A, 10B and 11, and incorporates an ultrasonic suction device 281, instead of the holding forceps 113 (FIG. 9). The suction device 281 comprises a water-supplying sheath 282, a grip 283, a lead line 284, and an operation section 285.

Figure 23:
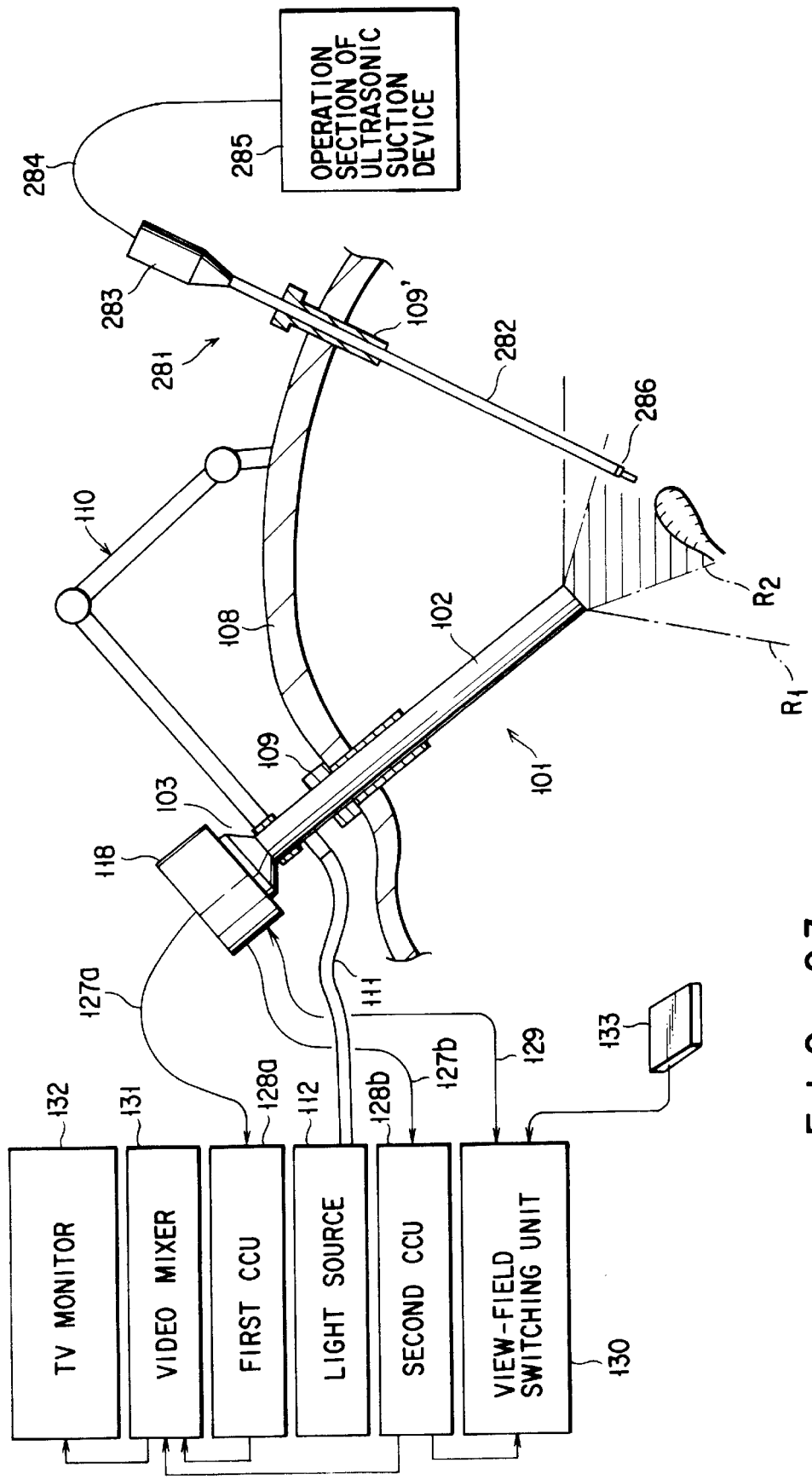
FIG. 23 is a diagram representing an endoscope surgery system according to a third modification of the fourth embodiment.

As shown in FIG. 23, the water-supplying sheath 282 is inserted into the peritoneal cavity through the second trocar 109' set in an opening incised in the abdominal wall 108. The grip 283 is connected to the proximal end of the insertion section 282. The lead line 284 is connected at one end to the grip 283 and at the other end to the operation section 285.

A color marker 286 of the same type used in the first modifications is provided on the distal end of the water-supplying sheath 282. As the surgeon moves the sheath 282, the view-field switching unit 130 switches the view field of the first CCD 125a to track the color marker 286 provided on the distal end of the sheath 282. The magnified image of the distal end portion of the sheath 282 is displayed on the screen of the TV monitor 132. Thus, the third modification can accomplish the same advantages as the fourth embodiment.

An endoscope surgery system according to a fourth modification of the fourth embodiment of the present invention will be described, with reference to FIG. 24.

The fourth modification is still another modification of the fourth embodiment shown in FIGS. 9, 10A, 10B and 11, and incorporates an laser probe 291, instead of the holding forceps 113 (FIG. 9).

Figure 24:
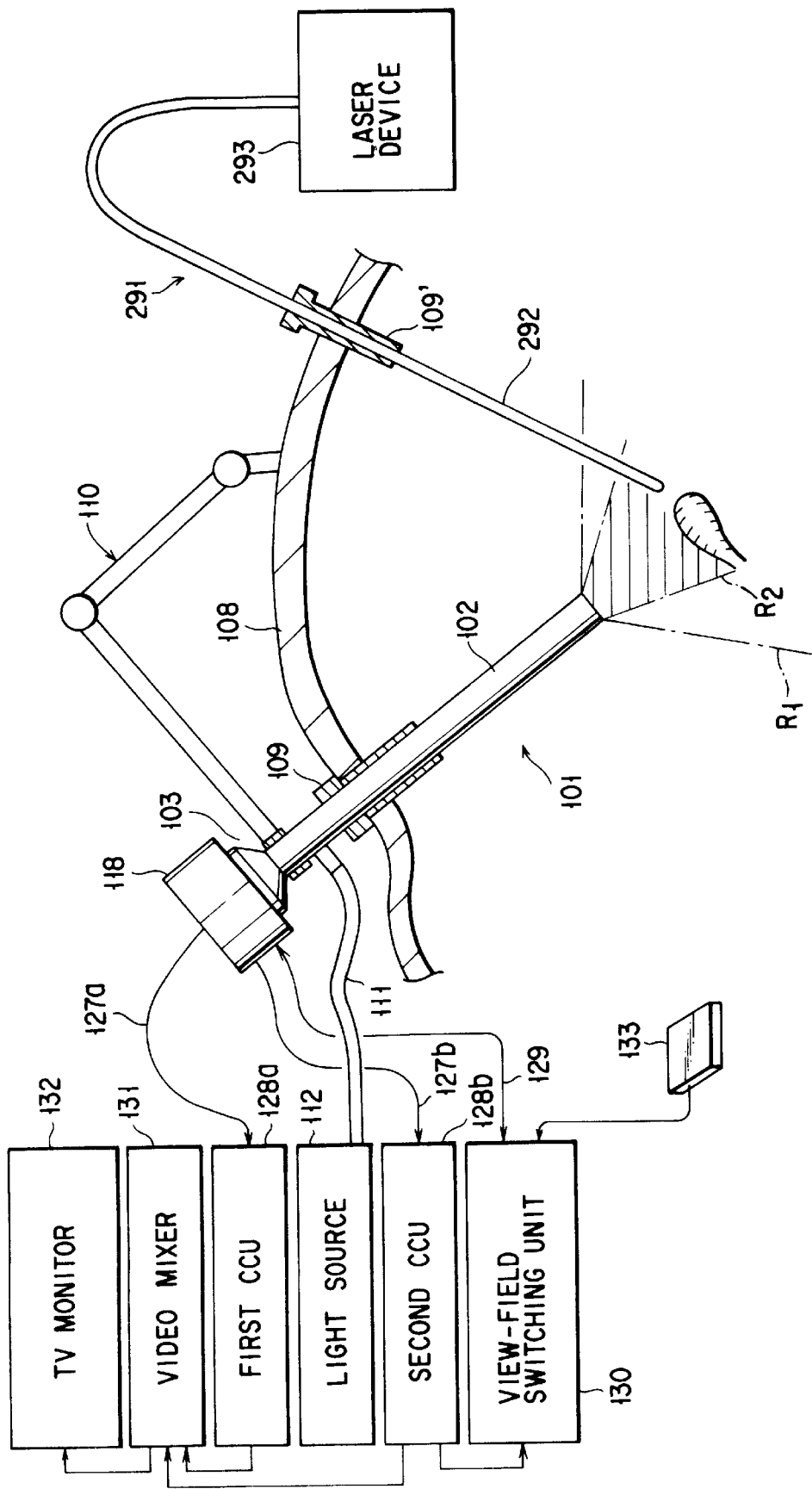
FIG. 24 is a diagram illustrating an endoscope surgery system according to a fourth modification of the fourth embodiment.

As shown in FIG. 24, the laser probe 291 comprises an insertion section 292 and a laser device 293. As shown in FIG. 24, the insertion section 292 has its distal end portion inserted into the peritoneal cavity through the second trocar 109' set in an opening incised in the abdominal wall 108. The laser device 293 is connected to the proximal end of the insertion section 292. The laser device 293 emits pilot light of the same color as the marker 265 used in the first modification (FIG. 21). The pilot light passes through the insertion section 292 and is applied from the distal end thereof. Alternatively, a color marker of the same type as the marker 265 used in the first modification may be provided on the distal end of the insertion section 292.

As the surgeon moves the insertion section 292, the view-field switching unit 130 switches the view field of the first CCD 125a to track the pilot light being emitted from the distal end of the insertion section 292. The magnified image of the distal end portion of the insertion section 292 is displayed on the screen of the TV monitor 132. Thus, the fourth modification can attain the same advantages as the fourth embodiment.

Figure 12:
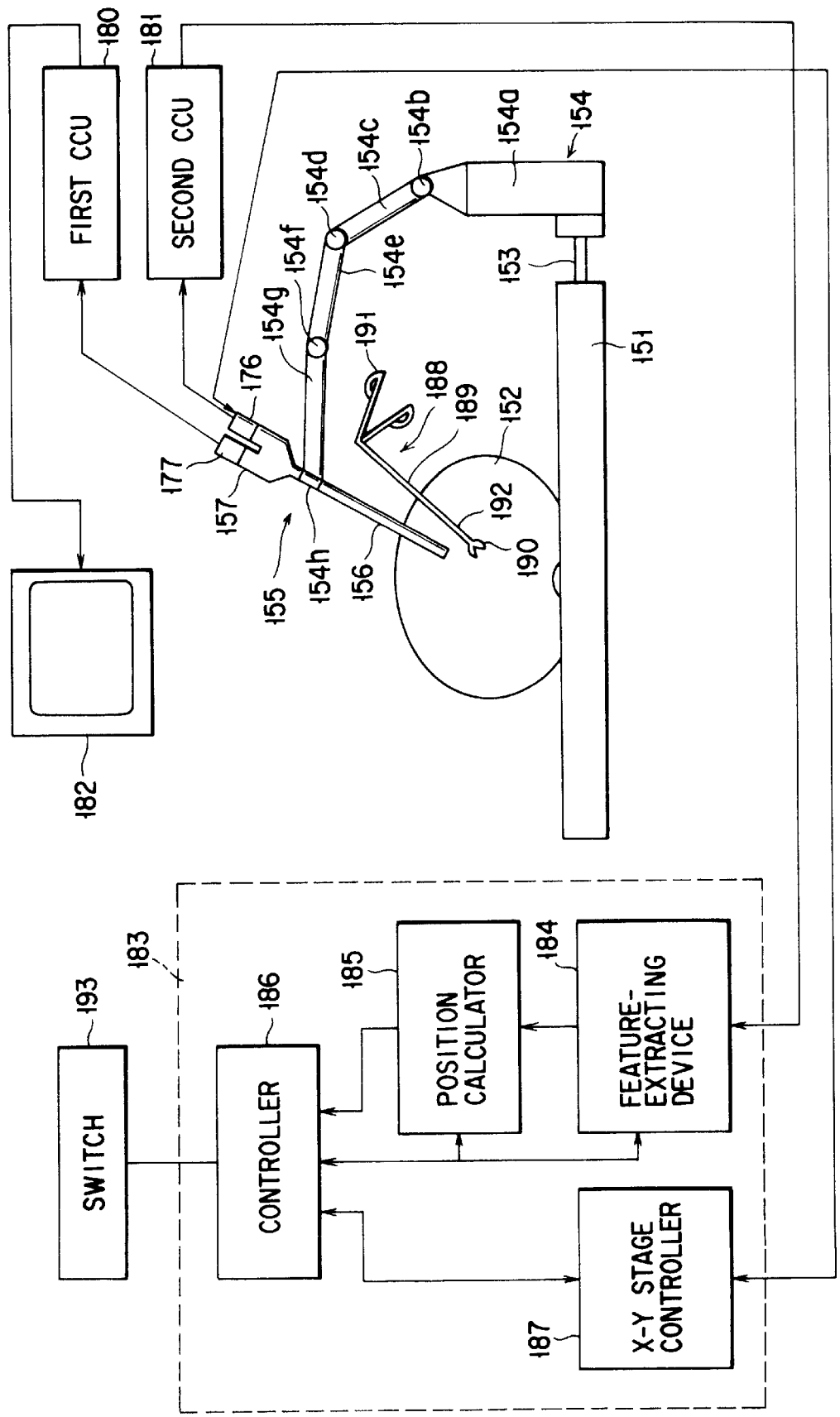
FIG. 12 is a diagram showing an endoscope surgery system according to a fifth embodiment of the present invention.

An endoscope surgery system, which is the fifth embodiment of the invention, will be described with reference to FIGS. 12, 13, 14A, 14B, 14C, 15A and 15B. FIG. 12 is a schematic representation of this endoscope surgery system.

As illustrated in FIG. 12, a patient 152 lies on his or her back on an operating table 151. A bedside rail 153 is secured to one side of the operating table 151. Attached to the beside rail 153 is a scope holder 154 of multi-joint structure.

The scope holder 154 comprises a base 154a, three joints 154b, 154d and 154f, three arms 154c and 154e and 154g, and a scope-holding member 154h. The base 154a is fastened to the beside rail 153. The first arm 154c is rotatably coupled to the base 154a by the first joint 154b. The second arm 154e is rotatably coupled to the first arm 154c by the second joint 154d. The third arm 154g is rotatably coupled at one end to the second arm 154e by the third join 154f. The other end of the third arm 154g is connected to the scope-holding member 154h.

A rigid scope 155 is removably connected to the scope-holding member 154h of the scope holder 154. Since the arms 154c, 154f and 154g can rotate at the joints 154b, 154d and 154f, the rigid scope 155 can be moved freely. The rigid scope 155 is inserted into the peritoneal cavity through the trocar (not shown) which is set in an opening incised in the abdominal wall of the patient 152. The trocar is of the same type as the trocar 109 shown in FIG. 9.

The rigid scope 155 is, for example, an endoscope of direct-view type, such as a laparoscope. The scope 155 will be described in detail, with reference to FIG. 13.

As shown in FIG. 12, the rigid scope 155 comprises an insertion section 156 and an ocular section 157. The insertion section 156 is to be inserted into a body cavity. The ocular section 157 is coupled to the proximal end of the insertion section 156. Two objective lens 158 and 159 are juxtaposed in the distal end of the insertion section 156. The lenses 158 and 159 have the same magnification.

The insertion section 156 has a hollow cylindrical sheath 160. The sheath 160 contains two sets of relay lenses. The first set consists of relay lenses 161, the foremost of which opposes the first objective lens 158 and is spaced apart therefrom. The second set consists of relay lenses 162, the foremost of which opposes the second objective lens 159 and is spaced apart therefrom.

Figure 13:
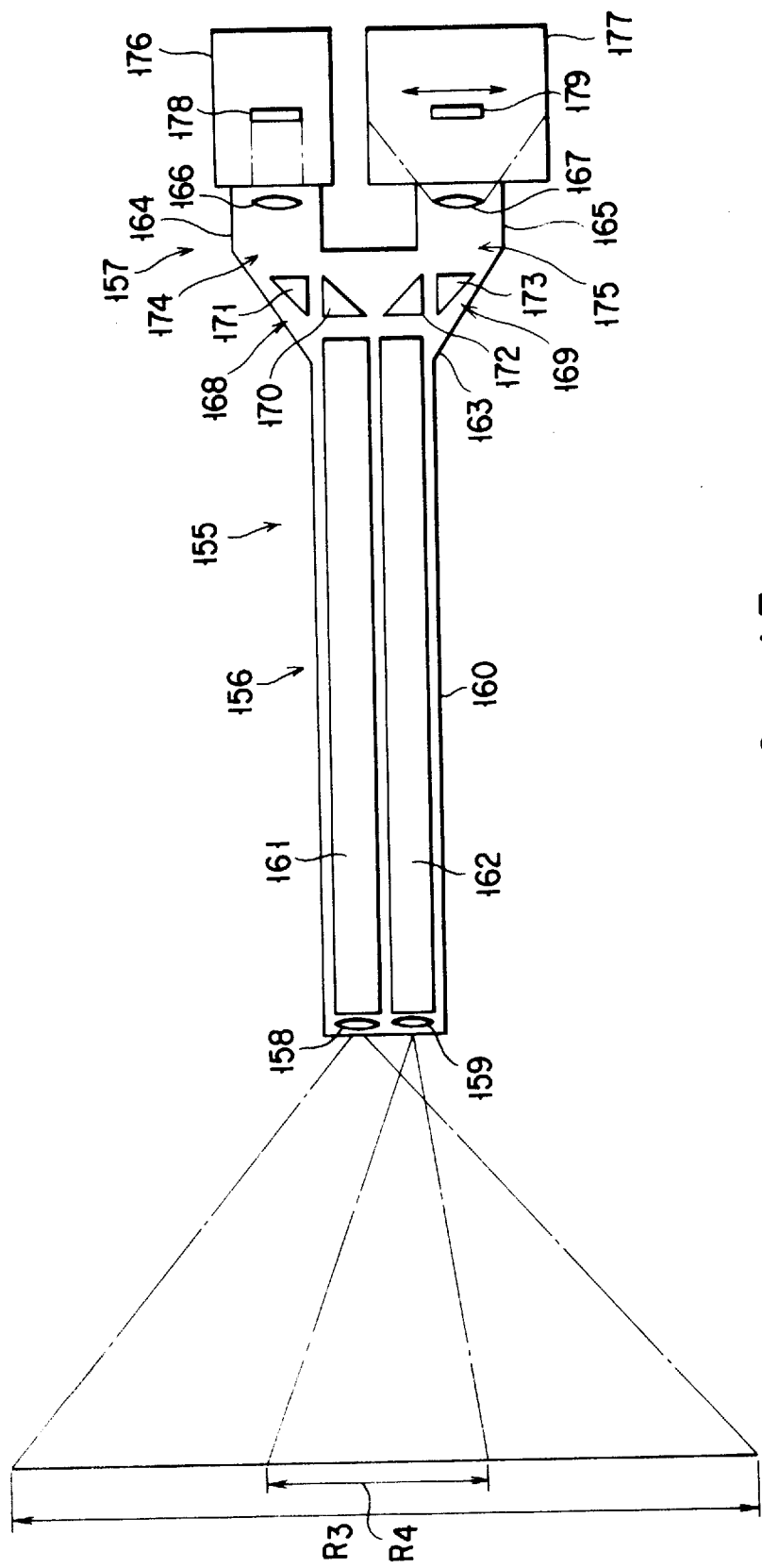
FIG. 13 is a diagram illustrating the internal structure of the endoscope incorporated in the fifth embodiment.

As shown in FIG. 13, the ocular section 157 of the rigid scope 155 comprises a coupler 163 and two barrels 164 and 165. The coupler 163 connects the barrels 164 and 165 to the proximal end of the insertion section 156. The barrels 164 and 165 extend parallel, side by side. Two ocular lenses 166 and 167 are provided in the proximal ends of the barrels 164 and 165, respectively. The first ocular lens 166 has magnification of 1, whereas the second ocular lens 167 has magnification of, for example, 2 to 3.

Two light guides 168 and 169 are provided in the coupler 163 of the ocular section 157. The first light guide 168 guides the light supplied from the first objective lens 158 via the relay lenses 161 to the first ocular lens 166. The second light guide 169 guides the light supplied from the first objective lens 159 via the relay lenses 162 to the second ocular lens 167. The first light guide 168 has two prisms 170 and 171. Similarly, the second light guide 169 has two prisms 172 and 173. The first objective lens 158, the relay lens 161, the prisms 170 and 171 of the first light guide 178, and the first ocular lens 166 constitute a wide-angle optical system 174 which can provide a wide-angle image of objects caught in the view field $R_3$ of the rigid scope 155. On the other hand, the second objective lens 159, the relay lens 162, the prisms 172 and 173 of the second light guide 179, and the second ocular lens 167 constitute a magnifying optical system 175 which can provide a magnified image of objects caught in the view field $R_4$ of the magnifying optical system 175.

A first TV camera unit 176 is removably connected to the barrel 164 which is a component of the wide-angle optical system 174. A second TV camera unit 177 is removably connected to the barrel 165 which is a component of the magnifying optical system 175. The first TV camera unit 176 contains a first CCD 178 for receiving the light supplied through the wide-angle optical system 174 to form a wide-angle image. The second TV camera unit 177 contains a second CCD 179 and an X-Y stage (not shown). The second CCD 179 is provided for receiving the light supplied through the magnifying optical system 175 to form a magnified image. The X-Y stage is used to move the second CCD 179 along X and Y axes, in a plane which intersects at right angles with the optical axis of the second CCD 179.

As illustrated in FIG. 12, the second TV camera unit 177, which is a component of the magnifying optical system 175, is connected to a first CCU (Camera Control Unit) 180. Similarly, the first TV camera unit 176, which is a component of the wide-angle optical system 174, is connected to a second CCU (Camera Control Unit) 181. The first CCU 180 is connected to a TV monitor 182. The output of the first CCU 180 is input to the TV monitor 182. The TV monitor 182 displays the magnified image formed by the second CCD 179 from the light supplied through the magnifying optical system 175.

The second CCU 181 is connected to a control section 183, which comprises a feature-extracting device 184, a position calculator 185, a controller 186, and an X-Y stage controller 187. The feature-extracting device 184 is connected to the second CCU 181, the position calculator 185, and the controller 186. The position calculator 185 is connected to the controller 186. Also connected to the controller 186 is the X-Y stage controller 187. Further, a switch 193 is provided outside the control section 183 and connected to the controller 186. The switch 193 is, for example, a foot switch or a hand switch. An electric motor (not shown) is connected to the X-Y stage controller 187, for driving the X-Y stage which supports the second CCD 179 incorporated in the second TV camera unit 177.

As shown in FIG. 12, a trocar (not shown) of the same type as the second trocar 109' shown in FIG. 9 is set in an opening incised in the abdominal wall of the patient 152. Through this trocar, a pair of forceps 188 is inserted into the peritoneal cavity. The forceps 188 comprises an insertion section 189, a pair of tongs 190, and a handle 191. The tongs 190 are connected to the distal end of the insertion section 189. The handle 191 is connected to the proximal end of the insertion section 189. When the handle 191 is opened and closed, the tongs 190 are opened and closed by remote control.

The insertion section 189 of the forceps 188 has feature portion 192 or a distal end portion. The portion 192 is painted in a specific color or has a specific pattern and can be distinguished from the other portion of the insertion section 189.

The operation of the fifth embodiment, or the endoscope surgery system shown in FIG. 12, will be explained with reference to FIGS. 12 and 13 and FIGS. 14A to 14C and 15A and 15B, each showing the screen of the TV monitor 182.

First, the surgeon inserts the insertion section 156 of the rigid scope 155 held by the scope holder 154 into the peritoneal cavity through the first trocar set in the abdominal wall. Light is applied from the distal end of the insertion section 156 into the cavity. The light reflected from the objects in the cavity is supplied through the magnifying optical system 175 of the rigid scope 155 to the CCD 179 provided in the second TV camera unit 177. The CCD 179 generates image data representing a magnified image of the objects caught in the view field $R_4$ of the magnifying optical system 175. The image data is supplied via the first CCU 180 to the TV monitor 182. The TV monitor 182 displays the magnified image.

While seeing this magnified image displayed by the TV monitor 182, the surgeon inserts the forceps 188 into the peritoneal cavity through the second trocar set in the abdominal wall, until the tongs 190 at the distal end of the forces 188 moves into the view field $R_4$ of the magnifying optical system 175 of the rigid scope 155.

The CCD 178 of the first TV camera unit 176 receives the light supplied through the wide-angle optical system 174 and generates image data representing a wide-angle image of the objects caught in the view field $R_3$ of the wide-angle optical system 174. This image data is supplied through the second CCU 181 to the control section 183.

In the control section 183, the feature-extracting device 184 receives the image data and extracts that part of the image data which represents the feature portion 192 of the forceps 188 (i.e., the distal end portion of the insertion section 189). The device 184 converts this part of the image data to binary image data.

The binary image data is supplied from the feature-extracting device 184 to the position calculator 185. The calculator 185 calculates the center of the image of the feature portion 192 and generates coordinate data representing the coordinates of the center of the image. This coordinate data is input to the controller 186.

Figure 14A:
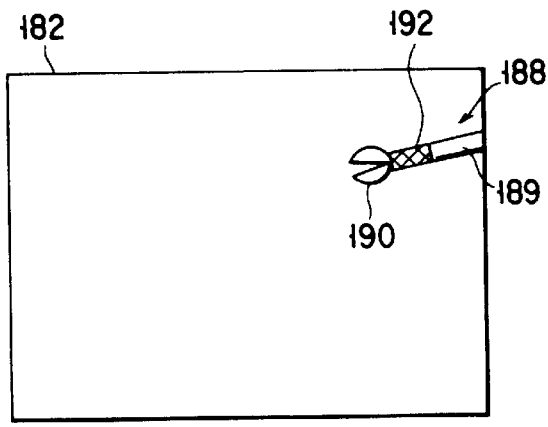
FIG. 14A is a front view of the TV monitor incorporated in the fifth embodiment, showing an image of a pair of forceps displayed on an edge portion of the TV monitor screen.
Figure 14B:
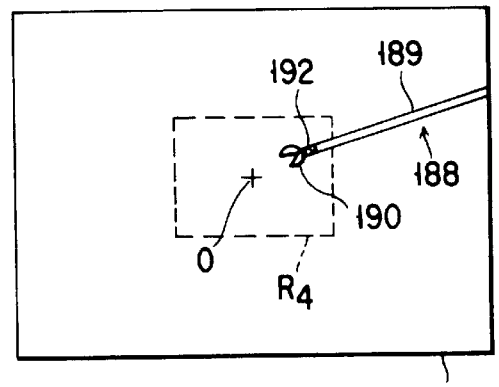
FIG. 14B is a front view of the TV monitor shown in FIG. 14A, showing an image of the forceps provided by the second CCD built in the wide-angle optical system.
Figure 14C:
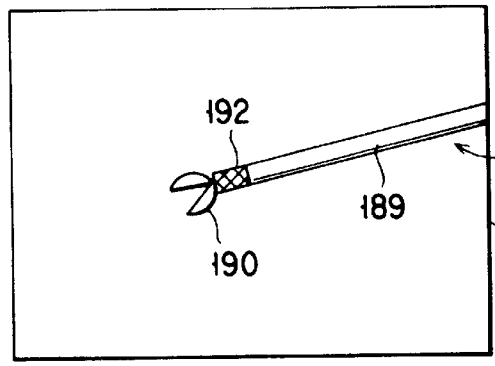
FIG. 14C is a front view of the TV monitor shown in FIG. 14A, showing an image of the forceps displayed in the center part of the enlarged-image displaying region of the TV monitor screen.

Assume that the magnified image of the feature portion 192 of the forceps 188 is displayed in an edge part of the screen of the TV monitor 182 as illustrated in FIG. 14A. Then, the wide-angle image of the forceps 188 is displayed on the TV monitor screen at the position shown in FIG. 14B. When the surgeon pushes the switch 193 in this condition, the controller 186 generates an image-moving signal and supplies the signal to the X-Y stage controller 187. In accordance with the image-moving signal, the X-Y stage controller 187 controls an electric motor (not shown). The electric motor drives the X-Y stage which supports the second CCD 179. As a result, the second CCD 179 is moved such that the image of the feature portion 192 of the forceps 188 is displayed at the center of the TV monitor screen as shown in FIG. 14C. Namely, the surgeon can see the magnified image of the interior of the cavity, with the distal end of the forceps 188 displayed at the center of the screen of the TV monitor 182.

Figure 15A:
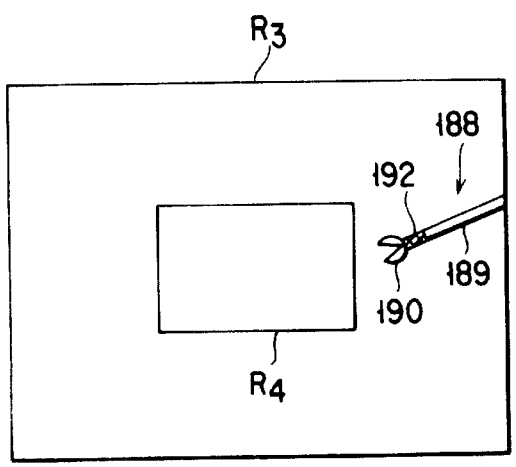
FIG. 15A is a front view of the TV monitor shown in FIG. 14A, showing an image of the forceps displayed outside the enlarged-image displaying region.
Figure 15B:
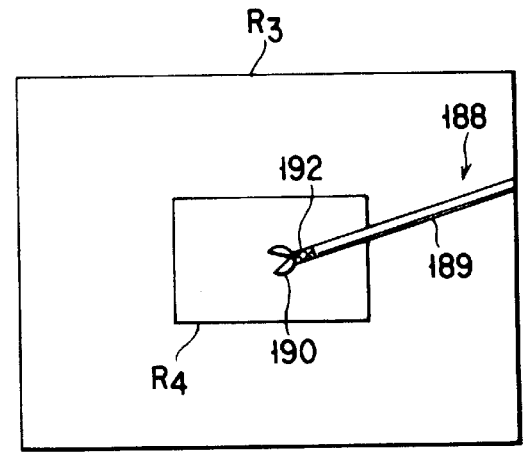
FIG. 15B is a front view of the TV monitor shown in FIG. 14A, showing an image of the forceps displayed in the center part of the enlarged-image displaying region.

The feature portion 192 of the forceps 188 may be displayed outside the view field $R_4$ of the magnifying optical system 175 as illustrated in FIG. 15A. Even if this case, the feature-extracting device 184 can extract that part of the image data which represents the feature portion 192. More precisely, the surgeon pushes the switch 193, causing the controller 186 to generates an image-moving signal, whereby the X-Y stage controller 187 controls the electric motor. The X-Y stage and, hence, the second CCD 179 are moved such that the image of the feature portion 192 is moved to the center of the TV monitor screen as shown in FIG. 15B.

The video signals output from the first CCU 180 and the second CCU 181 are supplied to a video mixer (not shown). The video mixer combines the input video signals, producing composite image data. The composite image data is input to the TV monitor 182. The TV monitor 182 displays the wide-angle image formed by the CCD 178 incorporated in the first TV camera unit 176, as well as the magnified image formed by the CCD 179 provided in the second TV camera unit 177.

The fifth embodiment (FIG. 12) is advantageous in the following respects.

Since the position which the feature portion 192 of the forceps 188 takes is detected from the wide-angle image provided by the wide-angle optical system 174, the X-Y stage provided in the second TV camera unit 177 can be driven in accordance with the image data generated by the second TV camera unit 177. The image of the feature portion 192 can thereby be moved to the center of the view field of the wide-angle optical system 174.

Further, the TV camera units 176 and 178 which have the wide-angle optical system 174 and the magnifying optical system 175, respectively, are much more simple in structure than the TV camera unit 118 of the fourth embodiment (FIG. 9) which incorporates two optical systems, i.e., the magnifying optical system 121 and the wide-angle optical system 122.

An endoscope surgery system, which is the sixth embodiment of the invention, will be described with reference to FIGS. 16A, 16B and 16C. The sixth embodiment is identical to the fifth embodiment (FIG. 12), except that, as seen from FIG. 16A, the forceps 188 has three feature portions 201, 202 and 203 on the distal end portion of the insertion section 189.

If the first feature portion 201 is covered with, for example, blood while the surgeon is manipulating the forceps 188, the feature-extracting device 184 can no longer extract that part of the image data which represents the feature portion 201. If this happens, the controller 186 supplies a control signal to the device 184, causing the device 184 to extract that part of the image data which represents either the second feature portion 202 or the third feature portion 203.

Assume that the feature-extracting device 184 extracts that part of the image data which represents the second feature portion 202. In this case, the X-Y stage supporting the CCD 179 of the second TV camera nit 177 may be moved to align the center of the image of the second feature portion 202 with the center of the screen of the TV monitor 182. For instance, the X-Y stage is moved so that the center of the image of the second feature portion 202 may move to a point near a circle 204 whose center coincides with the center of the view field $R_4$ of the magnifying optical system 175 and which has a radius r, as illustrated in FIG. 16C.

Alternatively, the feature-extracting device 184 extracts that part of the image data which represents either the first feature portion 201 or the third feature portion 203. If so, the X-Y stage may be moved to align the center of the image of the portion 201 or 203 with the center of the screen of the TV monitor 182.

As described above, the forceps 188 has three feature portions 201, 202 and 203 at the its distal end portion. Should any one or two of these feature portions are covered with, for example, blood, making it difficult for the feature-extracting device 184 to extract those parts of the image data which represent these feature portions, the device 184 can extract the that part of the image data which represents the remaining feature portion. Thus, the sixth embodiment is advantageous in that the position of the distal end portion of the forceps 188 can be reliably detected.

Another endoscope surgery system, which is the seventh embodiment of the invention, will be described with reference to FIGS. 17, 18A, 18B and 19. The seventh embodiment is a modification of the fourth embodiment shown in FIGS. 9, 10A, 10B and 11. The components identical or similar to those of the fourth embodiment are denoted at the same reference numerals in FIGS. 9, 10A, 10B and 11, and will not be described in detail.

The seventh embodiment is characterized by a TV camera unit 211 removably connected to the ocular section 103 of the rigid scope 101. The TV camera unit 211 differs in structure from the TV camera unit 118 incorporated in the fourth embodiment.

Figure 17:
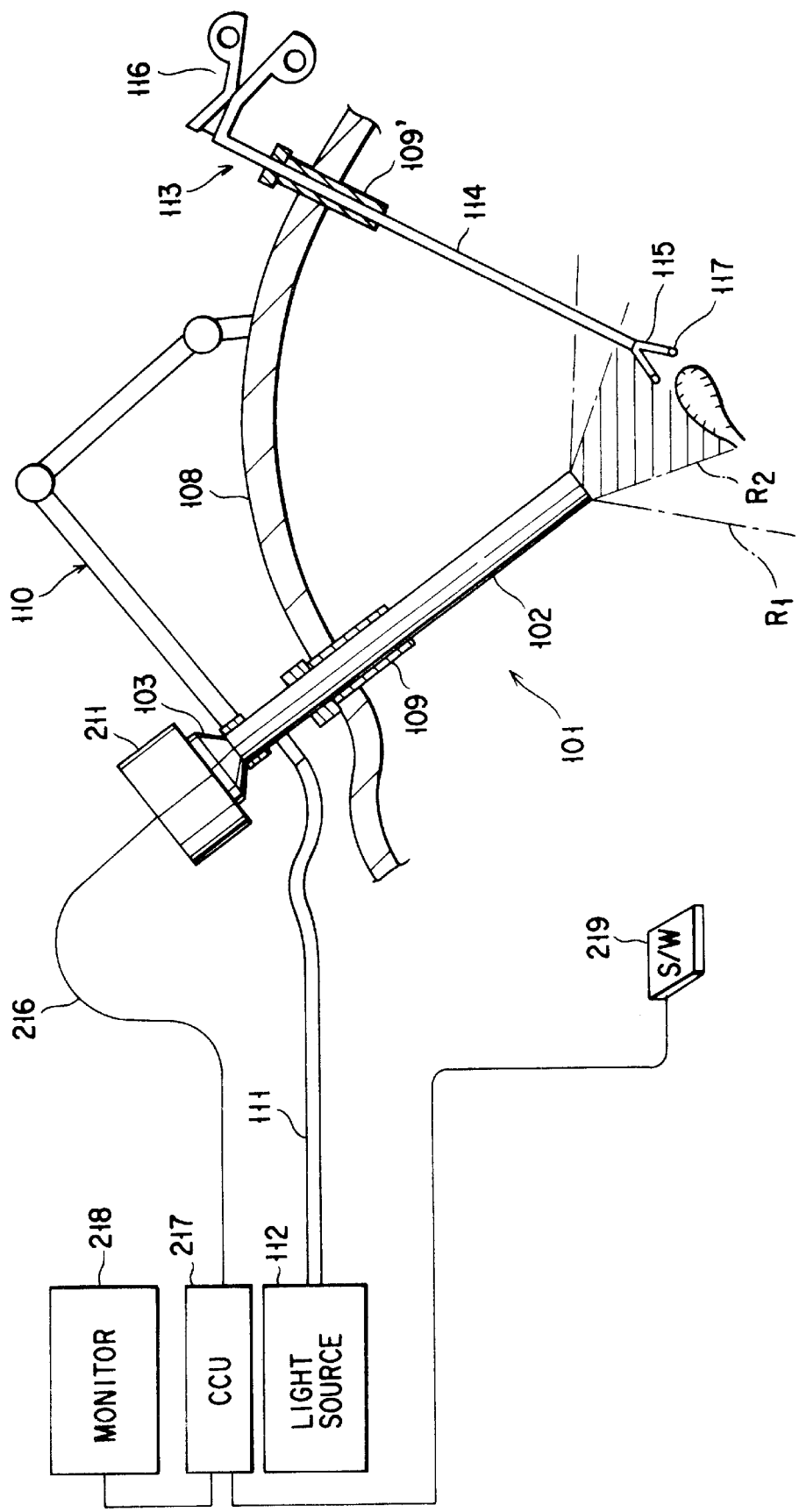
FIG. 17 is a diagram showing an endoscope surgery system according to a seventh embodiment of the present invention.
Figure 18A:
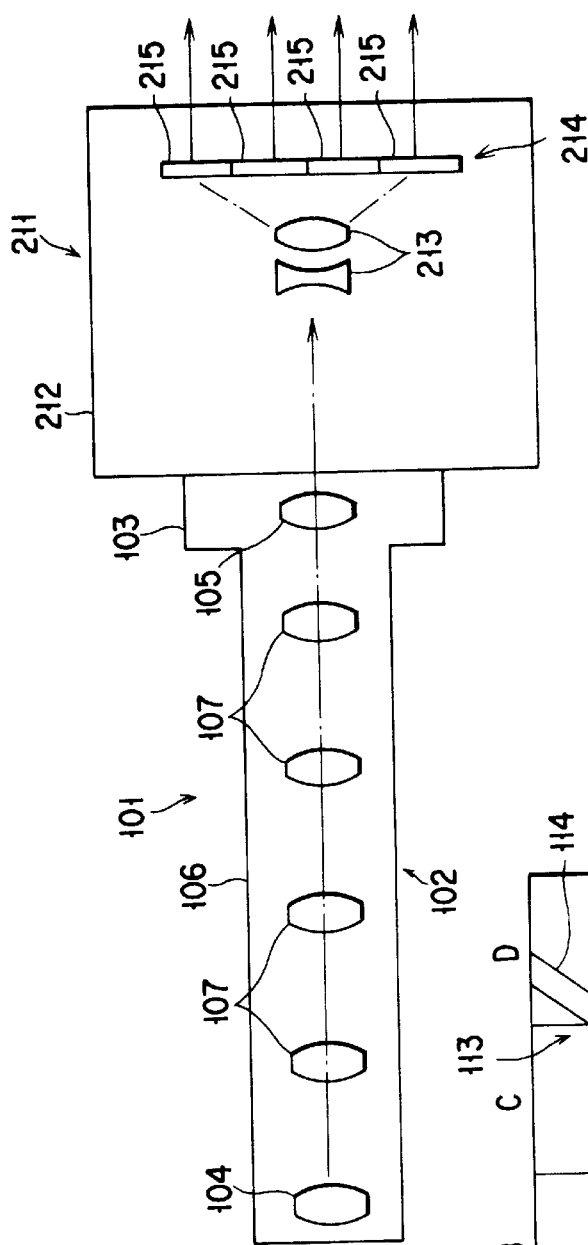
FIG. 18A is a diagram showing the rigid scope and the TV camera unit, both incorporated in the seventh embodiment.

As shown in FIG. 18A, the TV camera unit 211 comprises a casing 212, a lens unit 213, and an image pickup unit 214. The lens unit 213 and the image pickup unit 214 are provided within the casing 212. The image pickup unit 214 has a plurality of image pickup elements. The lens unit 213 opposes and is spaced apart from the ocular lens 105 incorporated in the ocular section 103 of the rigid scope 101. The image pickup unit 214 is located so as to from an optical image from the light supplied to it from the peritoneal cavity through the rigid scope 101. The image pickup elements of the unit 214 are solid-state elements. In the present embodiment, the unit 214 has 16 CCDs 215 arranged in four rows and four columns. As shown in FIG. 17, the TV camera unit 211 is connected by cable 216 to a camera control unit (CCU) 217. Also connected to the CCU 217 are a monitor 218 and a foot switch 219. The foot switch 219 may be replaced by a hand switch which can be removably attached to the handle 116 of the forceps 113.

Figure 18B:
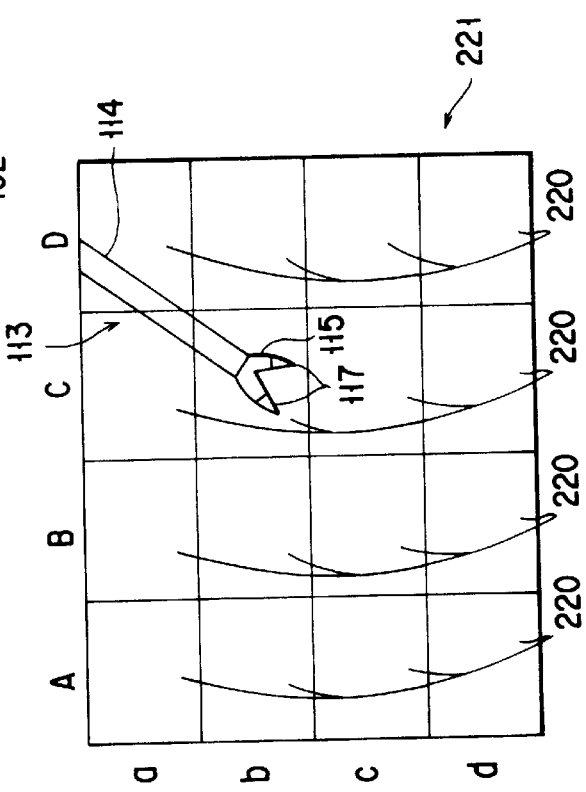
FIG. 18B is a diagram explaining how image data is stored in the frame memory incorporated in the seventh embodiment.

The CCU 217 has a frame memory unit 221. As shown in FIG. 18B, the frame memory unit 221 is comprised of 16 frame memories 220 (arranged at positions Aa to Dd), which are arranged in four rows and four columns. These frame memories 220 are connected to the 16 CCDs 215 of the image pickup unit 214, respectively.

Figure 19:
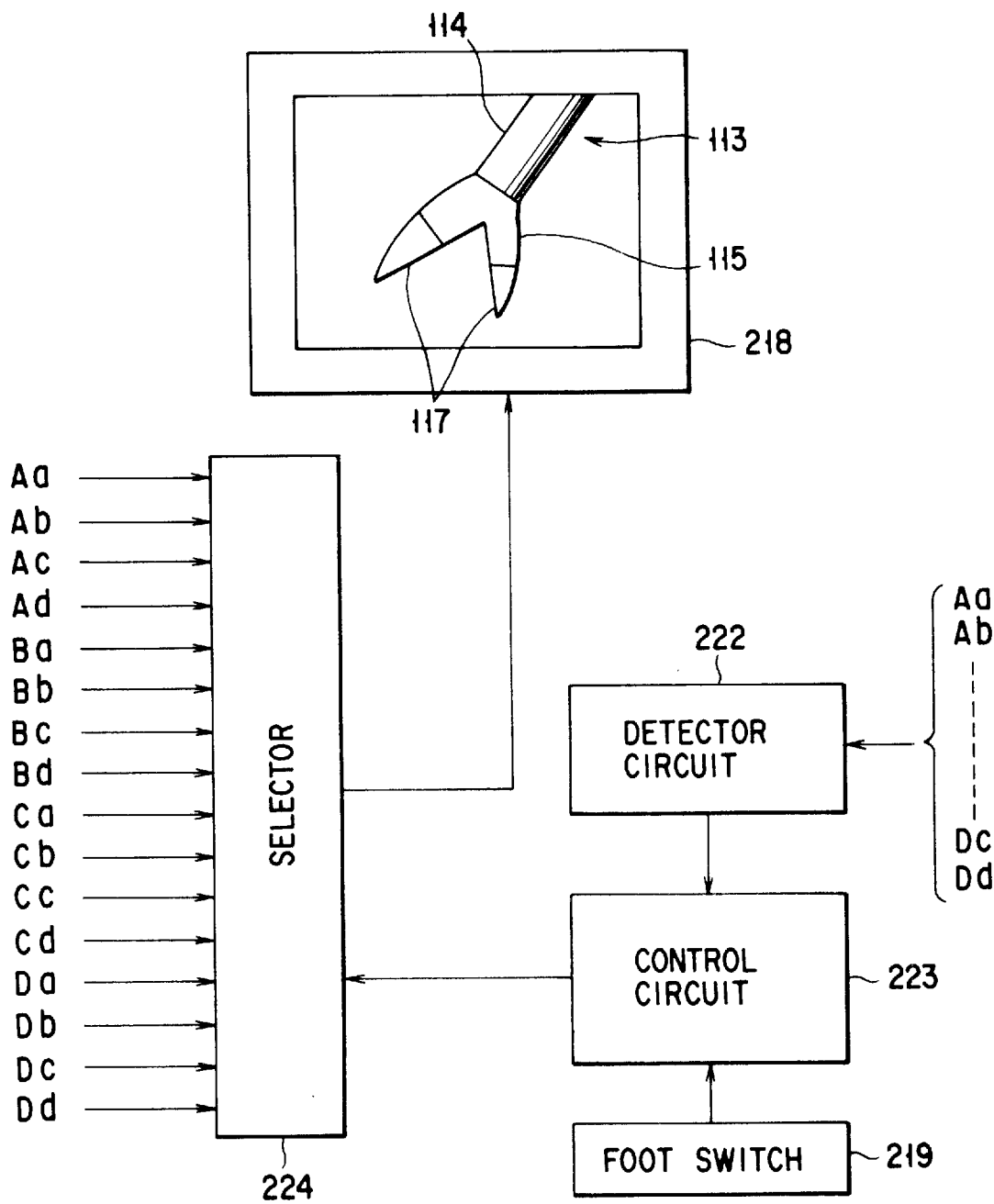
FIG. 19 is a block diagram showing the TV monitor and the control circuit, both provided in the seventh embodiment.

The CCU 217 further comprises a detector circuit 222, a control circuit 223, and a selector 224, as shown in FIG. 19. The detector circuit 222 is designed to detect the image data stored in the frame memories 220 of the frame memory unit 221. The foot switch 219 and the detector circuit 222 are connected to the control circuit 223. When controlled by a control signal generated by the control circuit 223, the selector 224 selects one of the frame memories 220. The image data stored in the frame memory selected is supplied to the monitor 218, which displays the image represented by the image data.

Whenever turned on, the foot switch 219 generates an ON signal, which is supplied to the control circuit circuit 223. Whenever turned off, the foot switch 219 generates an OFF signal to the control circuit 223. In response to the ON signal, the control circuit 223 switches the selector 224. In response to the OFF signal, the control circuit 223 does not switch the selector 224, maintaining the selector 224 in the same state.

The operation of the seventh embodiment, or the endoscope surgery system shown in FIG. 17, will be explained with reference to FIG. 17.

The surgeon observes the interior of the peritoneal cavity, using the rigid scope 101, while keeping the foot switch 219 off. If necessary, the surgeon inserts a pair of holding forceps 113 into the peritoneal cavity through the trocar 109' set in an opening incised in the abdominal wall 108. Then, the surgeon turns on the foot switch 219. An optical image of the interior of the cavity is transmitted to the image pickup unit 214 through the objective lens 104, relay lenses 107 and ocular lens 105, all provided in the insertion section 102 of the rigid scope 101, and further through the lens unit 213 provided in the TV camera unit 211.

In the image pickup unit 214, the CCDs 215 generate image data items from the optical image they have received. These image data items are stored into the frame memories 220 provided in the CCU 217. Assume that the image of the forceps 113 is applied to the CCDs 215 located at positions Cb, Ca and Da, as illustrated in FIG. 18B. Then, the image data items which represent the forceps 113 are stored into the three frame memories 220 arranged at positions Cb, Ca and DA and connected to those CCDs.

The signals output from the 16 frame memories 220 (located at positions Aa to Dd) are input to the detector circuit 222. The detector circuit 222 determines which frame memory stores the image data item representing the color marker 117 on the holding forceps 113. In the case where the image of the forceps 113 is applied to the CCDs 215 at positions Cb, Ca and Da as shown in FIG. 18B, it is determined that the frame memory at position Cb stores that image data.

The detector circuit 222 generates a signal designating the frame memory which stores the image data representing the holding forceps 113. This signal is supplied to the control circuit 223. The control circuit 223 controls the selector 224 in accordance with the input signal. Thus controlled, the selector 224 selects one of the frame memories 220 located at positions Aa to Dd. In the instance shown in FIG. 18B, the selector 224 selects the frame memory located at position Cb, whereby the image data stored in the selected frame memory is supplied to the monitor 218. As a result, the monitor 218 displays the distal end portion of the forceps 113, on which the color marker 117 is provided.

The seventh embodiment described above is advantageous in the following respects.

First, the surgeon need not move the rigid scope 101 to catch the distal end of the forceps 113 in the view field of the rigid scope 101. This is because, when the surgeon moves to the forceps 113 to a desired position, the selector 224 selects the frame memory 220 storing the image data representing the color marker 117, so that the monitor 218 displays the distal end portion of the forceps 113, on which the marker 117 is provided.

In addition, the view field of the rigid scope 101 is switched with high reliability since no mechanical means is employed to switch the view field.

Further, the image displayed by the monitor 218 hardly deteriorates since it is represented by one of the image data items generated by 16 CCDs 215 which constitute the image pickup unit 214 incorporated in the TV camera unit 211. Should it deteriorate, it would do so far less than in an image represented by a part of the image data which has been generated by a single CCD.

In the seventh embodiment, the image data items stored in the 16 frame memories 221 may be simultaneously supplied to the monitor 218 so that the monitor 218 displays the entire optical image provided by the image pickup unit 214. Alternatively, the image data items stored in some of the frame memories 221 may be simultaneously supplied to the monitor 218 so that the monitor 218 displays a specified part of the optical image. Further, the image data generated by the 16 CCDs 215 constituting the image pickup unit 214 in-cooperated in the TV camera unit 221 may be directly supplied to the monitor 218, not by way of the frame memories 220.

The rigid scope 101 may be held by an electrically driven manipulator (not shown) such that the color marker 117 on the distal end of the forceps 113 is located outside the view field of the rigid scope 101. If this happens, it suffices to operate the manipulator to move the color marker 117 into the view field, and to select one of the frame memories 220 which stores the data item representing the color marker 117.

Figure 20A:
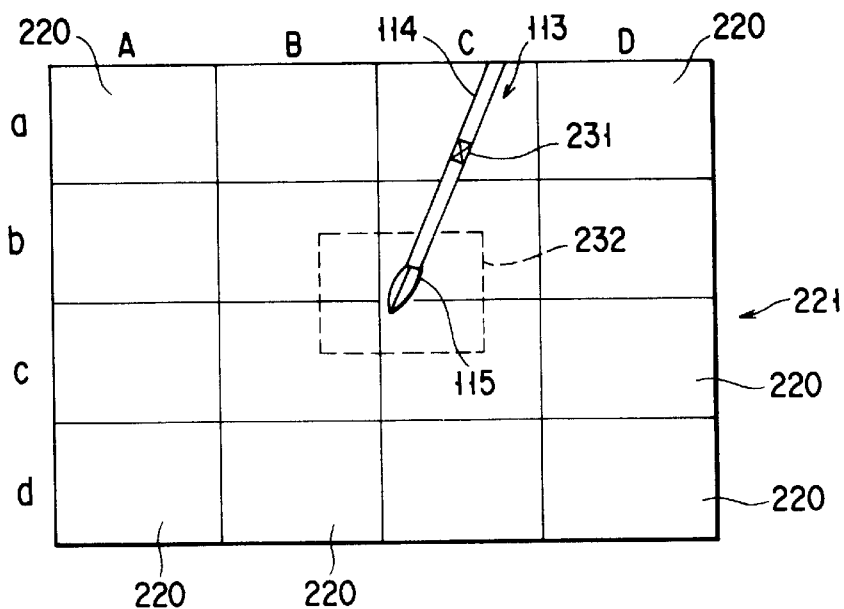
FIG. 20A is a diagram explaining how image data is stored in the frame memory incorporated in an endoscope surgery system according to an eighth embodiment of the invention.

Another endoscope surgery system, which is the eighth embodiment of the invention, will be described with reference to FIG. 20A. The eighth embodiment is identical to the seventh embodiment shown in FIGS. 17, 18A, 18B and 19, except that a color marker 231 is provided on the intermediate portion of the insertion section 114 of the holding forceps 113.

In the CCU 217, the detector circuit 222 detects the color marker 231 and generates a detection signal representing the position of the marker 231. The control signal is supplied to the control circuit 223. The control circuit 223 calculates the position of the tongs 115 attached to the holding forceps 113, from the position of the color marker 231. The selector 224 selects those of the frame memories 220 which are partly covered by a rectangular area which has the same size as each memory 220 and in which the image of the color marker 231 is located, as is illustrated in FIG. 20A. The data items stored in the frame memories 220, thus selected, are supplied to the monitor 218. The monitor 218 displays the image of the tongs 115 attached to the holding forceps 113, substantially in the center part of its screen.

With the eighth embodiment, the monitor 218 displays the distal end portion of the forceps 113 (i.e., the tongs 115) in the center part of its screen. This helps the surgeon to locate the image of the tongs 115 quickly on the monitor screen and, ultimately, to perform the surgery with high efficiency.

The image data generated by the 16 CCDs 215 constituting the image pickup unit 214 in-corporated in the TV camera unit 221 may be directly supplied to the monitor 218, not by way of the frame memories 220, as in the case of the seventh embodiment.

An endoscope surgery system according to the ninth embodiment of this invention will be described with reference to FIG. 20B. The ninth embodiment is characterized by the use of a rigid scope 241 of slant-view type. This rigid scope 241 comprises an insertion section 242 and an objective system provided in the distal end portion of the section 242. The objective system has its optical axis $O_2$ inclined at an angle $\alpha$ to the axis $O_1$ of the insertion section 242. The angle $\alpha$ is greater than 0°, but not exceeding 180°. Preferably, the angle $\alpha$ is 30°, for example. The objective system of the rigid scope 241 has a view angle $\beta$ of, for example, 70°. The view angle $\beta$ is so large that the axis $O_1$ of the insertion section 241 extends within the view angle $\beta$.

Figure 20B:
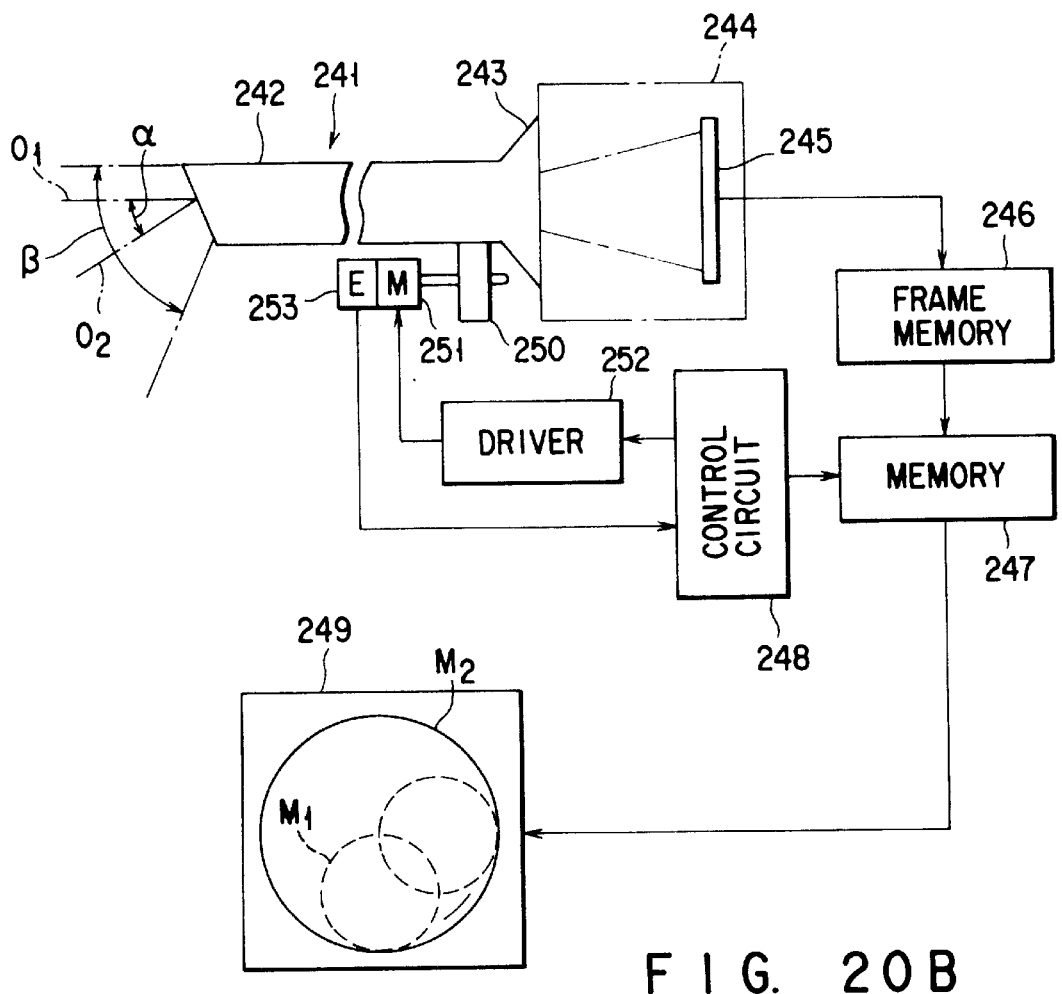
FIG. 20B is a diagram showing an endoscope surgery system according to a ninth embodiment of the present invention.

As shown on FIG. 20B, the rigid scope 241 has an ocular section 243, to which a TV camera unit 244 is removably connected. The TV camera unit 244 contains a CCD 245. The CCD 245 is connected to a frame memory 246, which in turn is connected to a memory 247. The memory 247 is connected to a control circuit 248 and a monitor 249. A drum 250 is mounted on the shaft of an electric motor 251. The drum 250 is set in contact with the circumferential surface of the proximal end portion of the rigid scope 241. When rotated by the motor 251, the drum 250 rotates the rigid scope 241 around its axis $O_1$. The electric motor 251 is connected to a driver 252, which in turn is connected to the control circuit 248. A rotary encoder 253 is fastened to the shaft of the motor 251 and electrically connected to the control circuit 248.

The operation of the ninth embodiment will be explained below.

The rigid scope 241 supplies an optical image to the TV camera unit 244, more precisely onto the light-receiving surface of the CCD 245. The CCD 245 converts the optical image into image data, which is stored into the frame memory 246. The image data is read from the frame memory 246 and stored into the memory 247.

In the meantime, the driver 252 drives the electric motor 251 under the control of the control circuit 248. The rigid scope 241 is thereby rotated around its axis $O_1$. Every time the rigid scope 241 is rotated through a predetermined angle, the rotary encoder 253 generates one signal. This signal is supplied to the control circuit 248. In response to the signal the circuit 248 causes the memory 247 to store the image data stored in the frame memory 246. Thus, the image data items generated by the CCD 245 are sequentially stored into the memory 247 via the frame memory 246 while the rigid scope 241 is being rotated around its axis $O_1$.

As long as the rigid scope 241 is rotated, the control circuit 248 generates a control signal, which is supplied to the memory 247. In response to the control signal the memory 247 supplies the image data items to the monitor 249, one after another. As a result, the monitor 249 displays the image of all objects that the scope 241 has scanned while rotating 360° around its axis $O_1$. In FIG. 20B, each small circle $M_1$ indicates an image which the monitor 249 displays as the scope 241 is rotated through the determine angle, and the large circuit $M_2$ the image which the monitor 249 displays as the scope 241 is rotated 360°.

As described, the image data items, each generated by the CCD 425 as the rigid scope 241 is rotated through the predetermined angle, are stored from the frame memory 246 into the memory 247, one after another. The image data items are sequentially read from the memory 247 to the monitor 249. Hence, all scanned by the scope 241 rotating 360° around its axis $O_1$ can be displayed on the monitor 249.

An endoscope surgery system according to the tenth embodiment of the present invention will be described, with reference to FIGS. 27A, 27B, 28A–28C, 29 and 30.

Figures 27A, 27B:
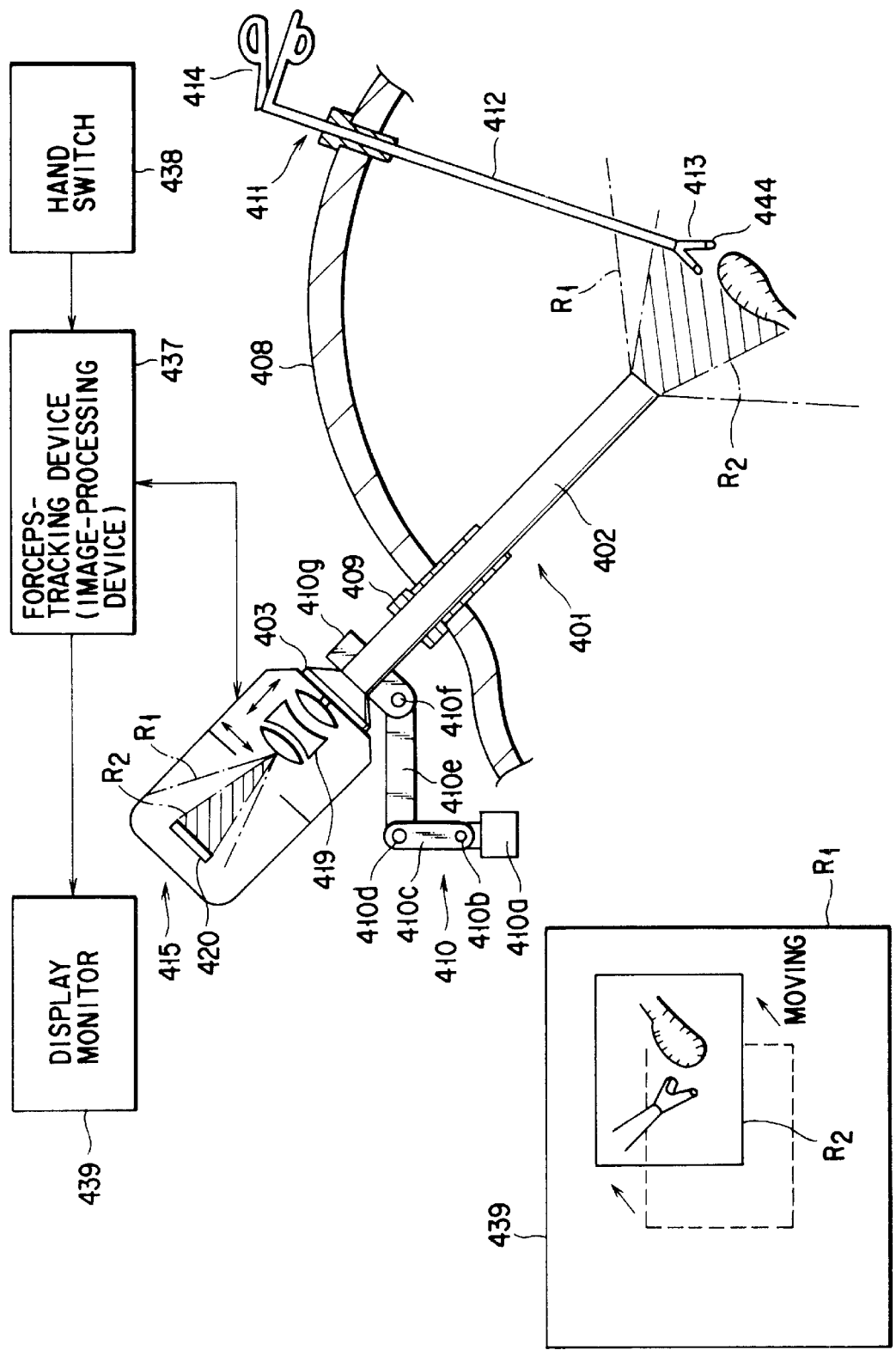
FIG. 27A is a diagram depicting an endoscope surgery system according to a tenth embodiment of the present invention.
FIG. 27B is a front view of the TV monitor incorporated in the tenth embodiment.

FIG. 27A is a diagram depicting this endoscope surgery system. As seen from FIG. 27A, the system has an endoscope 401 of direct-view type, such as a laparoscope. The endoscope 401 comprises an insertion section 402 and an ocular section 403. The insertion section 402 contains an objective lens 404 in its distal end, and the ocular section 403 contains an ocular lens 405.

The insertion section 402 is a barrel 406, which contains a plurality of relay lenses 407. The relay lenses 407 are located between the objective lens 404 and the ocular lens 405. They are spaced apart from one another. The optical system of the endoscope 401 further includes a distortion-compensating lens (not shown).

As seen from FIG. 27A, a trocar 409 is set in an opening incised in the abdominal wall 408 of a patient. The insertion section 402 of the endoscope 401 is inserted through the trocar 409 into the peritoneal cavity of the patient. The proximal portion of the insertion section 402 is movably held by a scope holder 410 which is a multi-joint structure. The scope holder 410 comprises a base 410a, three joints 140b, 410d and 410f, and two arms 410c and 410e, and a scope-holding member 410g. The base 410a is fixed in place. The first arm 410c is rotatably coupled by the first joint 410b to the base 410a. The second arm 410e is rotatably connected to the first arm 410c by the second joint 410d. The scope-holding member 410g is rotatably coupled by the third joint 410f to the second arm 410e. The scope-holding member 410g holds the endoscope 401.

A second trocar of the same type as the trocar 409 is set in an opening incised in the abdominal wall 408. Through this trocar, a pair of forceps 411 is inserted into the peritoneal cavity. The forceps 411 comprises an insertion section 412, a pair of tongs 413, and a handle 414. The tongs 413 are connected to the distal end of the insertion section 412. The handle 414 is connected to the proximal end of the insertion section 412. When the handle 414 is opened and closed, the tongs 413 are opened and closed by remote control. The forces 411 may be replaced by any other medical instrument such as ablation forceps, scissors, a laser probe, a suturing device, an electric knife, a stylus holder, and an ultrasonic suction device.

The TV camera 415 is removably attached to the ocular section 403 of the endoscope 401. The TV camera 415 is designed to generate image signals from the light supplied from the light supplied from the endoscope 401. As shown in FIG. 28A, the TV camera 415 comprises a casing 416. A partition 428 is provided in the casing 416, dividing the casing 416 into two component chambers 417 and 418. The first component chamber 417 contains optical elements 419 (e.g., a lens, a prism, a mirror, a zoom lens and the like) and image pickup device including a CCD 420. An optical image obtained at the ocular section 403 of the endoscope 401 is supplied, either in part or entirety, to the CCD 420 through the optical elements 419.

The second component chamber 418 contains a CCD-driving mechanism 421 for driving the CCD 420 along two axes extending at right angles to each other, in a plane perpendicular to the optical axis of the CCD 420. As shown in FIG. 28B, the mechanism 421 comprises two plates 422a and 422b, a set of four rollers 423a, and another set of four rollers 423b. Supported by the rollers 423a, the first plate 422a can move to the left and the right. Supported by the rollers 423b, the second plate 422b can move up and down. The first plate 422a has two guide slits 424a which extend vertically, and the second plate 422b has two guide slits 424b which extend horizontally.

A first pin 425a protrudes from the upper side of the first plate 422a and is loosely fitted in the helical groove of a feed screw 427a. The feed screw 427a is connected to the shaft of a first stepping motor 426a. When the first stepping motor 426a is driven, rotating the feed screw 427a, the first pin 425a is moved linearly. As a result, the first plate 422a is moved to the left or the right.

A second pin 425b protrudes from the right side of the second plate 422b and is loosely fitted in the helical groove of a feed screw 427b. The feed screw 427b is connected to the shaft of a second stepping motor 426b. When the second stepping motor 426b is driven, rotating the feed screw 427b, the second pin 425b is moved linearly. The second plate 422b is thereby moved upwards or downwards.

The partition 428 has an opening 430 in its center part. The opening 430 has a larger diameter than the base 429 on which the CCD 420 is mounted. The base 429 is secured to the slider 431 of the second component chamber 418. The slider 431 is made of material having a low coefficient of friction, such as polyacetal or high-molecular polyethylene.

Four operation pins 432 protrude from the lower surface of the slider 431. The operation pins 432 pass through the guide slits 424a of the first plate 422a and the guide slits 424b of the second plate 422b, at the intersections of these guide slits 424a and 424b. The slider 431 is arranged above the first plate 422a, with a leaf spring 432A interposed between it and the plate 422a. Due to the force applied to it by the spring 432A, the slider 431 abuts on the partition 428 and set in sliding contact therewith.

The slider 431 to which the CCD 420 is secured can move to the left and the right when the first stepping motor 426a is driven, and can move upwards and downwards when the second stepping motor 426b is driven. The stepping motors 426a and 426b constitute an actuator 433 which moves the CCD 420 (i.e., the image pickup device) incorporated in the TV camera 415. Instead of the actuator 433 there may be used an actuator which comprises DC servo motors, voice coils, piezoelectric elements, ultrasonic motors, or shape-memory alloy members.

As seen from FIG. 28C, a flexible printed wiring board 434 is connected at one end to the CCD 420. The other end of the printed wiring board 434 is connected to a CCD control circuit 435. The CCD control circuit 435 is held in place within the TV camera 415. The middle portion 436 of the flexible printed wiring board 434 is bend in the form of letter U and does not restrict the motion of the CCD 420.

As shown in FIG. 27A, a forceps-tracking device 437 is coupled to the TV camera 415. Connected to the device 437 are a switch 438 and a display monitor 439. The switch 438 is, for example, a foot switch, a hand switch or the like. The display monitor 439 is, for example, an HMD (Head Mounted Display) or the like.

Figure 29:
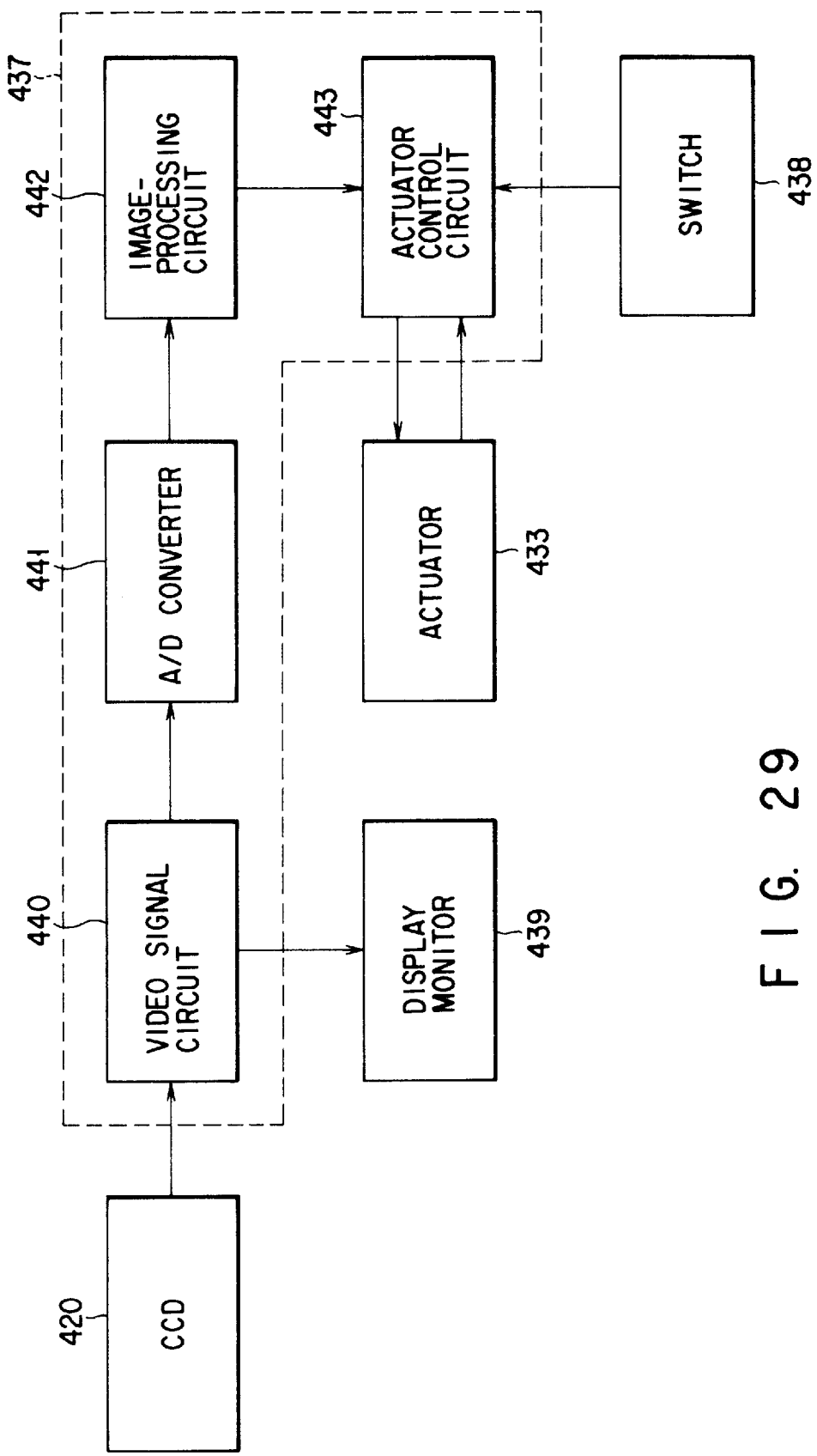
FIG. 29 is a block diagram showing the forceps-tracking device incorporated in the tenth embodiment.

As illustrated in FIG. 29, the forceps-tracking device 437 comprises a video signal circuit 440, an A/D converter 441, an image-processing circuit 442, and an actuator control circuit 443. The video signal circuit 440 is connected to the CCD 420 and the display monitor 439. It processes a video signal supplied from the CCD 420, converting it to a video signal such as an NTSC signal or an RGB signal. The video signal generated by the circuit 440 is input to the A/D converter 441. The A/D converter 441 converts the video signal to a digital signal, which is supplied to the image-processing circuit 442. From the digital signal the circuit 442 determines the position of the distal end of the forceps 411, the position of the CCD 420, the distance and direction in which the CCD 420 has moved, the position of the actuator 433, and the distance and direction in which the actuator 433 has moved. The circuit 442 generates data representing these positions, these distances and these directions. Thus, the image-processing circuit 442 functions to detect the position of the distal end of the forceps 411.

One of two alternative methods may be utilized to detect the position which the distal end of the forceps 411 takes. The first method is to detect the center of the color marker provided on the distal end of the forceps 411, as will be later explained with reference to FIG. 30. The second method is to determine the shape of the forceps 411 and compares the shape with models, thereby to detect the position of the distal end of the forceps 411, as will be later explained with reference to FIG. 32.

As shown in FIG. 29, the actuator 433 and the switch 438 are connected to the actuator control circuit 443. The circuit 443 controls the actuator 433 in accordance with the data which the image-processing circuit 442 has generated and which represent the position the distal end of the forceps 411 assumes, the position the CCD 420 takes, the direction and distance the CCD 420 has moved, the position the actuator 433 takes, and the direction and distance the actuator 433 has moved. Thus controlled, the actuator 433 drives the CCD-driving mechanism 421. The mechanism 421 moves the CCD 420 along two axes extending at right angles to each other, switching the view field of the TV camera 415.

As described above, the actuator 433 comprises the stepping motors 426a and 426b. Open-loop control is therefore carried out in the present embodiment. If the actuator 433 is replaced by one comprising DC motors, closed-loop control will be performed in which the DC motors are controlled by the signals fed back from rotary encoders.

The switch 438 has a push button for activating and deactivating the forceps-tracking device 437. While the push button remains depressed, the device 437 keeps operating to move the CCD 420 such that the display monitor 439 displays the distal end of the forceps 411, substantially in the center part of its screen. Assume that the distal end of the forceps 411 is displayed outside the center part of the monitor screen as illustrated in FIG. 27B. In this case, the surgeon pushes the button of the switch 438, whereby the CCD 420 is moved so that the image of the distal end of the forceps 411 moves to the center of the screen of the display monitor 439.

It will be explained how a surgeon operates the tenth embodiment to perform endoscope surgery.

The surgeon inserts the insertion section 402 of the endoscope 401 into the peritoneal cavity through the trocar 409 set in an opening incised in the abdominal wall 408 of the patient. Then, he or she inserts the forceps 411 into the peritoneal cavity through the second trocar set in an opening incised in the abdominal wall 408. The surgeon moves the forceps 411 such that the tongs 423 of the forceps 411 may be caught in the view field $R_1$ of the ocular section 403 of the endoscope 401.

As described above, the TV camera 415 is attached to the ocular section 403 of the endoscope 401. An optical image of the objects represent in a narrower view field $R_2$ is supplied to the CCD 420 through the optical elements 419 of the TV camera 415. The CCD 420 converts the optical image into image data.

As indicated above, the endoscope 401 and the TV camera 415 are removably coupled together, and the endoscope 401 can be easily disconnected from the TV camera 415. The endoscope 401, which is a direct-view type scope, can easily be replaced by a scope of a different type having a different view angle, such as a slant-view type rigid scope. Once disconnected from each other, the endoscope 401 and the TV camera 415 can be sterilized independently. Thus, the endoscope 401 which is inserted in part into a body cavity, may be sterilized in an autoclave, whereas the TV camera 415 containing electronic devices (e.g., the CCD 420) which will become less durable if sterilized may be subjected EOG sterilization less moderate than autoclave sterilization.

When the push button on the switch 438 is pushed while the TV camera 415 is forming an image from the light supplied from the endoscope 401, the forceps-tracking device 437 is activated to track the distal end of the forceps 411. As long as the device 437 operates, the video signals output from the CCD 420 are sequentially supplied via the A/D converter 441 to the image-processing circuit 442. The circuit 442 processes the video signals to determine the position of the distal end of the forceps 411, as will be explained with reference to the flow chart of FIG. 30.

To facilitate the determining of the position, a color marker 444 is provided on one of the tongs 413 attached to the distal end of the forceps 411, and a color correlation circuit is incorporated in the image-processing circuit 442.

At first, the optical image provided by the TV camera 415 is acquired (Step S1). This image is converted to a video signal, which is input to the color correlation circuit. The color correlation circuit detects the color of the color marker 444 provided on the tong 413 (Step S2). Further, the positions and orientations which the three axes (X, Y and Z axes) of the color marker 444 assume are detected. Rotational/parallel coordinate transform is performed based on the positions and orientations thus detected. The signal representing the color of the marker 444 is converted to binary signal (Step S3). The center of the color marker 444 is calculated (Step S4). The position of the distal end of the forceps 411 is inferred (Step S5). Then, the magnification and the coordinate axes are corrected (Step S6), thereby calculating the position the distal end of the forceps 411 takes.

The distance the CCD 420 has moved is calculated from the data representing the position of the distal end of the forceps 411 (Step S7). The data indicative of this distance is output (Step S8).

The signal output from the image-processing circuit 442 is input to the actuator control circuit 443. The circuit 443 generates a control signal from the position of the distal end of the forceps 411 and the distance the CCD 420 has moved, both calculated by the image-processing circuit 442. The control signal is supplied to the actuator 433.

Controlled by the control signal, both stepping motors 426a and 426b of the actuator 433 drive the CCD-driving mechanism 421. The mechanism 421 moves the CCD 420 on the slider 431, along two axes extending at right angles to each other and to the optical axis of the CCD 420. The view field of the TV camera 415 is thereby switched such that the TV camera 415 tracks the tongs 413 attached to the distal end of the forceps 411, as long as the forceps-tracking device 437 performs its function. As a result of this, the tongs 413 fixed to the distal end of the forceps 411, the position of which has been detected by the forceps-tracking device 437, are displayed in substantially a central part of the screen of the display monitor 439.

If it is desired, the tongs 413 do not have to be displayed in the center part of the screen of the display monitor 439. In this case, the surgeon pushes the button on the switch 438. The forceps-tracking device 437 is thereby activated, tracking the distal end of the forceps 411. Ultimately, the CCD-driving mechanism 421 moves the CCD 420, switching the view field of the TV camera 415, whereby the TV camera 415 tracks the tongs 413 until the image of the tongs 423 appears in the center part of the screen of the display monitor 439.

The tenth embodiment of the present invention is advantageous in the following respects.

First, as the surgeon moves the tongs 413 to a desired position, the view field of the endoscope 401 is automatically switched so that the tongs 413 are displayed in the center part of the screen of the display monitor 439. This is because the forceps-tracking device 437 keeps tracking the distal end of the forceps 411 as long as the button on the switch 438 remains depressed, causing the CCD-driving mechanism 421 to move the CCD 420 until the image of the tongs 423 appears in the center part of the monitor screen. The endoscope 401 is not moved at all as the view field is switched. Thus, the endoscope 401 would not bother the surgeon manipulating the forceps 411 or inflict pain on the patient.

Further, it is easy for the surgeon to switch the view field of the endoscope 401, even if he or she holds a medical instrument with one hand and another with the other hand. Once the surgeon has pushed the button on the switch 438, the view field is automatically changed as he or she moves the distal end of the forceps 411 to any desired position in the peritoneal cavity.

Still further, the surgeon need not ask an assistant to move the endoscope 401 to have the view field of the endoscope 410 located at a desired position. Since the surgeon neither requires an assistant's help nor needs to move the endoscope 401 to locate the view field at a desired position, the efficiency of the endoscope surgery can be enhanced.

Moreover, the endoscope surgery system can be provided at a relatively low cost. This is because the CCD-driving mechanism 421 for switching the view field of the endoscope 401 is less expensive than a mechanism which moves the endoscope 401 to switch the view field thereof.

In addition, since a whole image taken up by the CCD 420 is displayed on the light-receiving surface of the TV camera 415, the image displayed by the display monitor 439 can have high quality.

Furthermore, although the flexible printed wiring board 434 is repeatedly bent as the CCD 420 is moved, it is durable since its middle portion 436 is bent in the form of letter U.

Moreover, any dust in the CCD-driving mechanism 421 is prevented from sticking to the CCD 420. This is because the mechanism 421 is provided within the second component chamber 418 which is completely separated by the partition 428 and the slider 431 from the first component chamber 417 which contains the CCD 420.

FIG. 31 is a flow chart explaining another method of tracking the distal end of the forceps 411. In this alternative method, the shape of the tongs 413 attached to the distal end of the forceps 411 is detected, and the detected shape is compared with models to detect the position of the distal end of the forceps 411.

A shape marker is mounted on one of the tongs 413. This marker has a peculiar shape and can well be distinguished from any object present in the peritoneal cavity. A pattern-matching circuit (not shown) is incorporated in the image-processing circuit 442.

While the forceps-tracking device 437 remains activated, video signals are sequentially supplied from the video signal circuit 440 via the A/D converter 441 to the image-processing circuit 442. The circuit 442 processes the video signals, thereby to detects the position of the distal end of the forceps 411.

More specifically, the optical image provided by the TV camera 415 is acquired (Step S11). The optical image is converted into a video signal, which is input to the pattern-matching circuit provided in the image-processing circuit 442. The pattern-matching circuit determines the position of the shape marker from the image data generated by the TV camera 415 and representing the tongs 413. The circuit converts the image data into a binary signal and performs outline emphasis on the binary signal. To be more precise, the circuit detects the outline of the shape marker (Step S12). Then, it detects a straight line from the outline (Step S13). Next, the image-processing circuit 442 compares the shape of the tongs 413 with models (Step S14). The circuit 442 infers the position of the distal end of the forceps 411 (Step S15). Further, the circuit 442 corrects the magnification and the coordinate axes (Step S16), thereby calculating the position the distal end of the forceps 411 takes.

The distance the CCD 420 has moved is calculated from the data representing the position of the distal end of the forceps 411 (Step S17). The data indicative of this distance is output (Step S18).

The signal output from the image-processing circuit 442 is input to the actuator control circuit 443. The circuit 443 generates a control signal from the position of the distal end of the forceps 411 and the distance the CCD 420 has moved, both calculated by the image-processing circuit 442. The control signal is supplied to the actuator 433.

Controlled by the control signal, both stepping motors 426a and 426b of the actuator 433 drive the CCD-driving mechanism 421. The mechanism 421 moves the CCD 420 on the slider 431, along two axes extending at right angles to each other and to the optical axis of the CCD 420. The view field of the TV camera 415 is thereby switched such that the TV camera 415 tracks the tongs 413 attached to the distal end of the forceps 411, as long as the forceps-tracking device 437 performs its function.

The shape marker may not be used at all. If this is the case, the shape of the distal end of the forceps 411 may be compared with models, thereby to calculate the position of the distal end of the forceps 411.

Figures 32A, 32B:
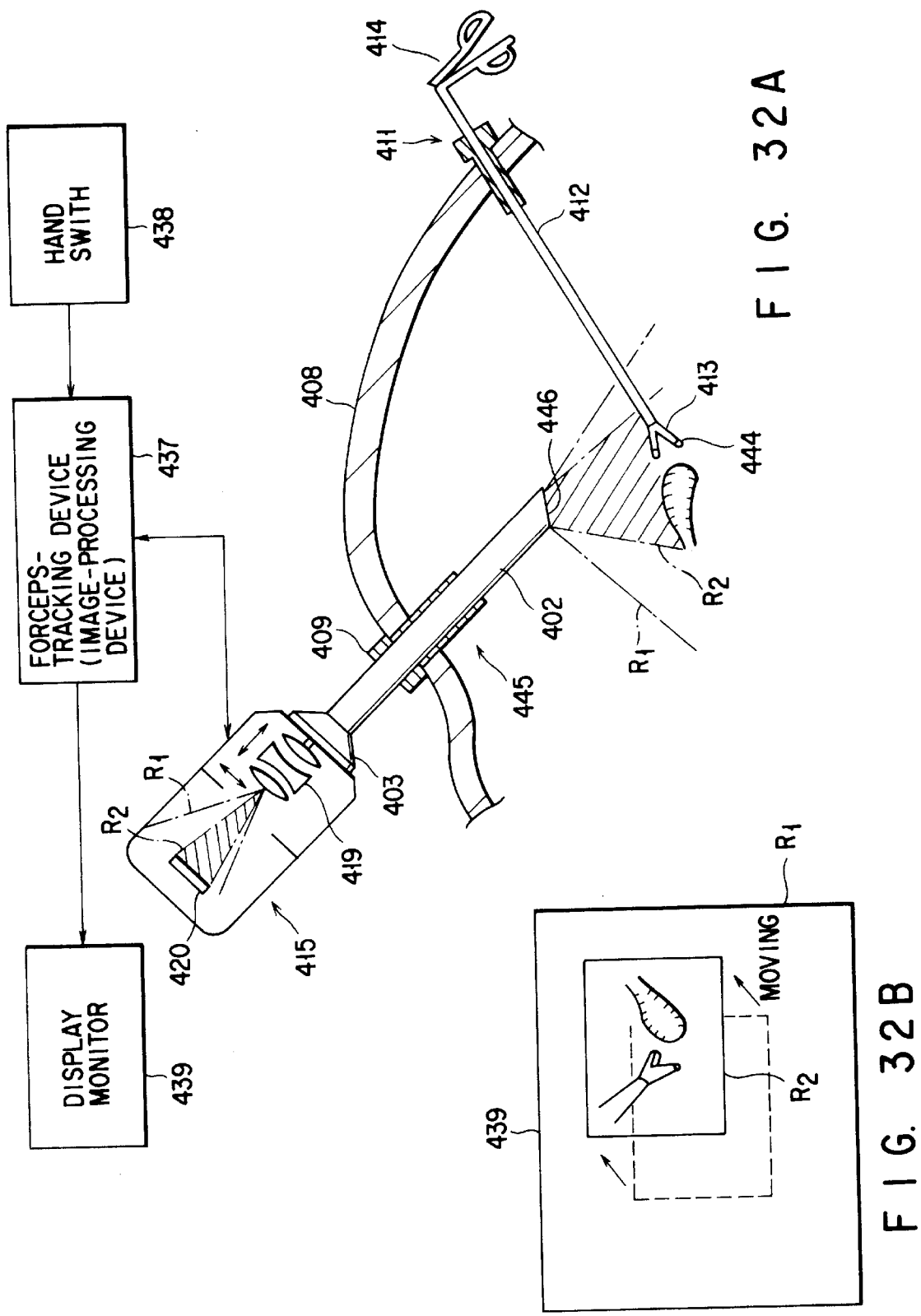
FIG. 32A is a diagram depicting an endoscope surgery system according to an eleventh embodiment of this invention.
FIG. 32B is a front view of the TV monitor incorporated in the eleventh embodiment.

An endoscope surgery system according to the eleventh embodiment of the invention will be described, with reference to FIGS. 32A and 32B.

The eleventh embodiment is a modification of the tenth embodiment shown in FIGS. 27A, 27B, 28A, 28B, 28C, 29 and 30. It differs from the tenth embodiment in that a scope 445 of slant-view type is used as shown in FIG. 32A, in place of the direct-view type endoscope 401. The scope 445 has an observation window 446 at the distal end of the insertion section 402. The window 446 is a slant-view type, inclined to the optical axis of the insertion section 402. Except for these features, the scope 455 is identical to the endoscope 401 incorporated in the tenth embodiment.

In the eleventh embodiment, as the CCD-driving mechanism 421 provided in the TV camera 415 moves the CCD 420, the view field of the scope 445 is switched. Hence, to have view field switched, the scope 445 need not be rotated around its optical axis as the ordinary slant-view type scope to which no CCD-driving mechanism is connected.

As in the tenth embodiment, the optical elements 419 of the TV camera 415 may be moved to switch the narrow view field $R_2$ with respect to the light-receiving surface of the CCD 420.

Another endoscope surgery system, which is the twelfth embodiment of this invention, will be described with reference to FIGS. 33A, 33B and 33C. The twelfth embodiment is a second modification of the tenth embodiment.

Figures 33A, 33B, 33C:
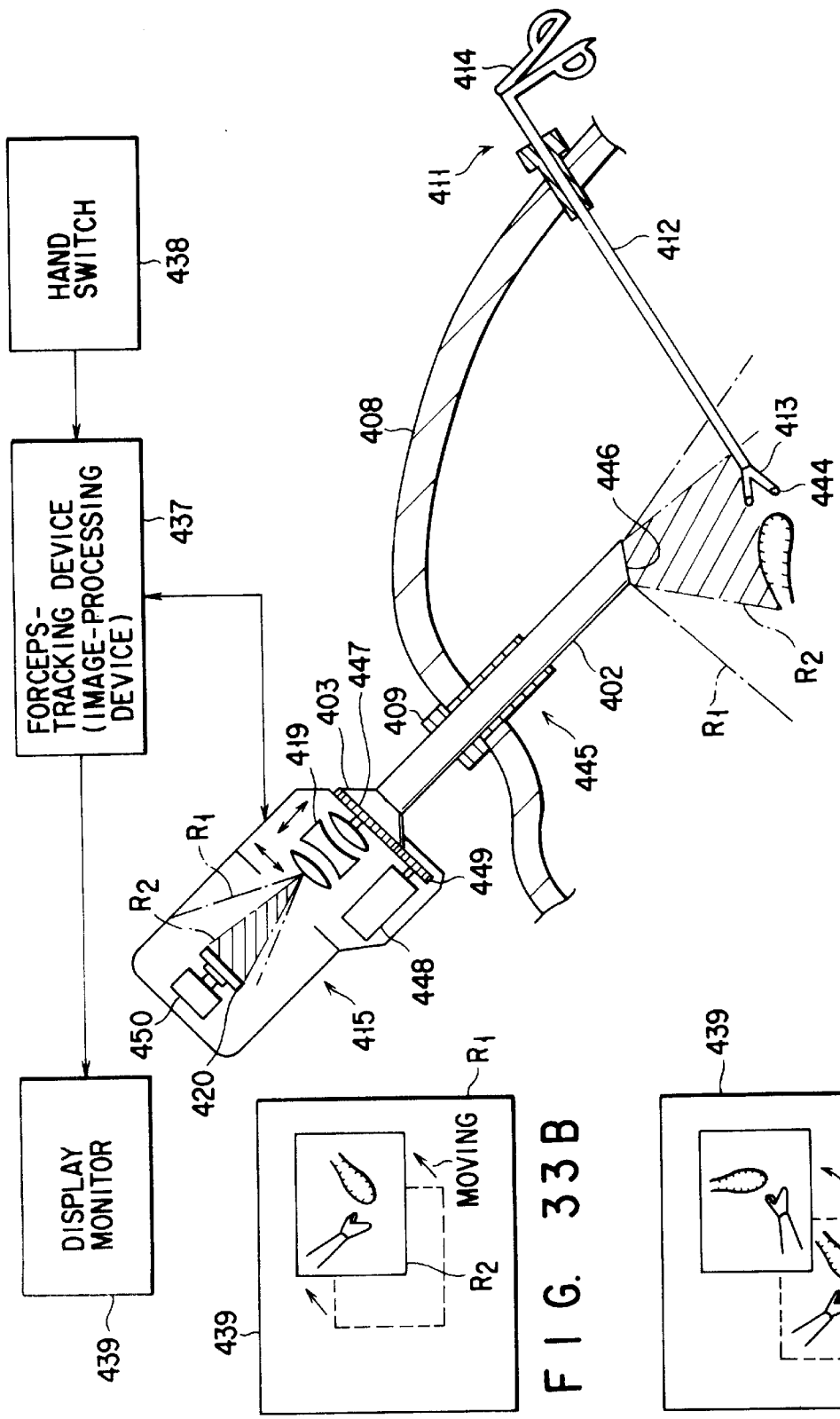
FIG. 33A is a diagram showing an endoscope surgery system according to a twelfth embodiment of this invention.
FIG. 33B is a front view of the TV monitor incorporated in the twelfth embodiment, showing an image of an instrument and an image of a tissue.
FIG. 33C is a front view of the TV monitor incorporated in the twelfth embodiment, showing the images of the instrument and tissue, which are rotated by about 90°.

A scope 445 of slant-view type is used as shown in FIG. 33A, in place of the direct-view type endoscope 401. The scope 445 has an observation window 446 at the distal end of the insertion section 402. The window 446 is a slant-view type, inclined to the optical axis of the insertion section 402. A TV camera 415 is rotatably connected to the scope 445. As shown in FIG. 33A, a gear 447 is mounted on the outer circumferential surface of the ocular section 403 of the scope 445. The TV camera 415 contains optical elements 419, a CCD 420, an actuator 448 (e.g., an electric motor), and an actuator 450. The first actuator 448 is used to rotate the scope 445 around its optical axis; it is connected to a gear 449 set in mesh with the gear 447 provided on the ocular section 403. Thus, the actuator 448 can rotate the scope 445 with respect to the TV camera 415. The second actuator 450 is designed to rotate the CCD 420 around the optical axis of the TV camera 415.

Except for the features described in the preceding paragraph, the twelfth embodiment is identical to the tenth embodiment.

The second actuator 450 drives the CCD-driving mechanism 421, which moves the CCD 420 to switch the view field of the scope 445 and, ultimately, move the image provided by the CCD 420 on the screen of the display monitor 439. In addition, the second actuator 448 rotates the slant-view type scope 448, whereby the scope 448 scans a larger region of the peritoneal cavity, detecting objects which would not otherwise be seen through the scope 448.

As the scope 448 is rotated, the image obtained by the scope 448 rotates on the screen of the display monitor 438 as illustrated in FIG. 33C. Nonetheless, the image can be rotated back to the initial position as shown in FIG. 33B, merely by rotating the CCD 420 in the opposite direction by means of the actuator 450. Both actuators 448 and 450 are controlled by the data which the forceps-tracking device 437 generates as long as the switch 438 remains depressed. The scope 445 and the CCD 420 are, therefore, automatically rotated and moved so that image of the distal end of the forceps 411 may be displayed in the center part of the display monitor 439.

The slant-view scope 445 may be replaced by a direct-view rigid scope of the type used in the tenth embodiment. In this case, the optical elements 419 provided in the camera 415 attached to the scope may be moved to switch the narrow view field $R_2$ of the TV camera 415.

Still another endoscope surgery system, which is the thirteenth embodiment of the invention, will be described with reference to FIGS. 34A to 34C, FIGS. 35A to 35C, and FIG. 36. This embodiment is a third modification of the tenth embodiment. It has zoom lens mechanism 451 for changing the magnification of the optical image projected on the light-receiving surface of the CCD 420 incorporated in the TV camera 415.

Figures 35A, 35B, 35C:
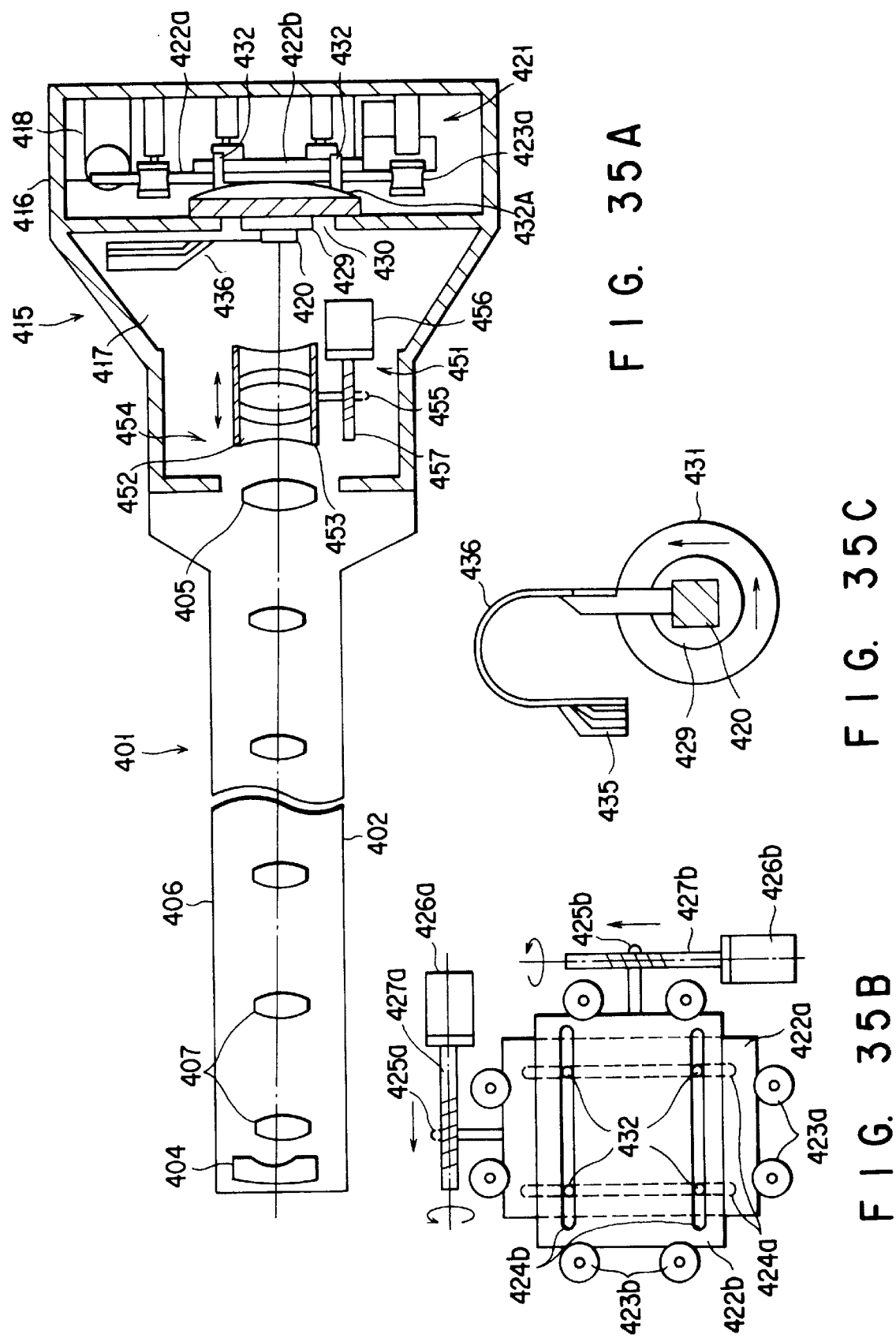
FIG. 35A is a longitudinal sectional view of the TV camera connected to the ocular section of the scope incorporated in the thirteenth embodiment.
FIG. 35B is a diagram showing the CCD-driving mechanism provided in the thirteenth embodiment.
FIG. 35C is a side view of the flexible printed board connected to the CCD incorporated in the thirteenth embodiment.

As shown in FIG. 35A, the zoom lens mechanism 451 has a zoom lens unit 454 comprised of a zoom lens 452 and a lens holder 453 holding the zoom lens 452. The zoom lens unit 454 is arranged between the ocular lens 405 of the scope 401 and the CCD 420. The unit 454 can be moved along its optical axis in the first component chamber 417 of the TV camera 415. A pin 455 protrudes from the lens holder 453 of the zoom lens unit 454.

The first component chamber 417 of the TV camera 415 contains a stepping motor 456 which serves as the drive means of the zoom lens mechanism 451. The shaft of the stepping motor 456 is connected to a feed screw 457. The pin 455 of the zoom lens unit 454 is loosely fitted in the helical groove of the feed screw 457. Hence, when the motor 456 is driven, rotating the feed screw 457, the pin 455 is moved linearly. The zoom lens unit 454 is thereby moved along its optical axis.

As seen from FIG. 34A, a switch unit 438 is connected to the forceps-tracking device 437, which in turn is connected to the TV camera 415. The switch unit 438 has three switches 458a, 458b and 458c. The first switch 458a is provided to activate and deactivate the forceps-tracking device 437. The second switch 438b and the third switch 458c are provided to move the zoom lens 454. The zoom lens unit 454 is moved to magnify the image formed on the CCD 420 when the second switch 458b is pushed, and to reduce that image when the third switch 458c is pushed.

Except for the features described above, the thirteenth embodiment is identical to the tenth embodiment. The components similar or identical to those of the tenth embodiment are designated at the same reference numerals in FIGS. 34A to 34C and FIGS. 35A to 35C, and will not be described in detail in the following explanation.

The operation of the thirteenth embodiment will be explained.

When the first switch 458a of the switch unit 438 is pushed while the TV camera 415 is forming an image from the light supplied from the scope 401, the forceps-tracking device 437 is activated to track the distal end of the forceps 411. As long as the device 437 operates, the video signals output from the CCD 420 are sequentially supplied via the A/D converter 441 to the image-processing circuit 442. The circuit 442 processes the video signals to determine the position of the distal end of the forceps 411, as will be explained with reference to the flow chart of FIG. 36.

First, the optical image provided by the TV camera 415 is acquired (Step S31). This image is converted to a video signal, which is input to the color correlation circuit. The color correlation circuit detects the color of the color marker 444 provided on the tong 413 (Step S32). Further, the positions and orientations which the three axes (X, Y and Z axes) of the color marker 444 assume are detected. Rotational/parallel coordinate transform is performed based on the positions and orientations thus detected. The signal representing the color of the marker 444 is converted to binary signal (Step S33). The center of the color marker 444 is calculated (Step S34). The position of the distal end of the forceps 411 is inferred (Step S35).

Then, the magnification is calculated from the position of the pin 455 of the actuator for driving the zoom lens unit 454 (Step S36). Since the stepping motor 456 serves to drive the zoom lens mechanism 451, the controller of the actuator can detect the position of the pin 455. The stepping motor 454 may be replaced by a DC motor, in which case the positioned of the pin 455 is detected by means of a rotary encoder.

If the axis along which the CCD 420 is moved to the left or the right does not coincide with the axis along which the CCD-driving mechanism 421 moves, the coordinate axes of the CCD 420 is corrected (Step S37). The distance the zoom lens unit 454 has moved is calculated.

The distance the CCD 420 has moved is calculated from the distance the zoom lens unit 454 has moved and from the reduction rate of the CCD-driving mechanism 421 (Step S38). Thereafter, the stroke of the CCD 420 is obtained (Step S39). The stroke is the distance for which the CCD 420 can move so long as the narrow view field $R_2$ of the CCD 420 remains in the broader view filed $R_1$ of the ocular lens 405 of the scope 401. The stroke of the CCD 420 varies with the magnification defined by the zoom lens mechanism 451.

The stroke of the CCD 420 is compared with the distance the CCD 420 has moved (Step S40). If the stroke is equal to or less than the distance, the image-processing circuit 442 outputs a signal representing the distance (Step S41). If the stroke is greater than the distance, the circuit 442 does not output the signal.

The signal output from the image-processing circuit 442 is input to the actuator control circuit 443. The circuit 443 generates a control signal from the position of the distal end of the forceps 411 and the distance the CCD 420 has moved, both calculated by the image-processing circuit 442. The control signal is supplied to the actuator 433.

Controlled by the control signal, both stepping motors 426a and 426b of the actuator 433 drive the CCD-driving mechanism 421. The mechanism 421 moves the CCD 420 on the slider 431, along two axes extending at right angles to each other and to the optical axis of the CCD 420. The view field of the TV camera 415 is thereby switched such that the TV camera 415 tracks the tongs 413 attached to the distal end of the forceps 411, as long as the forceps-tracking device 437 performs its function. As a result, the tongs 413 are displayed in the substantially central part of the screen of the display monitor 439.

The tongs 413 may not be displayed in the center part of the screen of the display monitor 439. In this case, the surgeon pushes the first switch 458a on the switch unit 438. The forceps-tracking device 437 is thereby activated, and the CCD-drive mechanism 421 is controlled until the image of the tongs 413 moves to the center part of the display monitor screen.

When the surgeon pushes the second switch 458b on the switch unit 438, the zoom lens unit 454 of the zoom lens mechanism 451 is moved to magnify the image formed on the light-receiving surface of the CCD 420. As shown in FIG. 34C, the image having a size R₃ and displayed in the center part of the screen expands to the size R₃' indicated by the solid lines. When the surgeon pushes the third switch 458c on the switch unit 438, the zoom lens unit 454 of the zoom lens mechanism 451 is moved in the opposite direction to reduce the image formed on the light-receiving surface of the CCD 420. In this case, the image having the size R₃' and displayed in the center part of the screen shrinks to the size R₃ indicated by the broken lines.

If the distal end of the forceps 411 is located outside the view field of the TV camera 415, it is necessary to drive the zoom lens mechanism 451, thereby to expand the view field into a wide-angle view field. As the view field is expanded, the image of the distal end appears on the screen of the display monitor 439. Then, the distal end of the forceps 411 can be tracked.

The thirteenth embodiment is advantageous in several respects.

First, as the surgeon moves the tongs 413 to a desired position, the view field of the scope 401 is automatically switched such that the tongs 413 is displayed in the center part of the screen of the display monitor 439. This is because the forceps-tracking device 437 keeps tracking the distal end of the forceps 411 as long as the first switch 458a on the switch unit 438 remains depressed, causing the CCD-driving mechanism 421 to move the CCD 420 until the image of the tongs 413 appears in the center part of the monitor screen. The scope 401 is not moved at all as the view field is switched, not bothering the surgeon manipulating the forceps 411 or inflicting pain on the part of the patient.

In addition, the view field of the scope 401 can be changed in size. More specifically, the view field is enlarged by pushing the second switch 458b, moving the zoom lens unit 454 in a direction along its optical axis to magnify the image formed on the light-receiving surface of the CCD 240. Alternatively, the view field is reduced by pushing the third switch 458c, moving the zoom lens unit 454 in the opposite direction along its optical axis to reduce the image formed on the light-receiving surface of the CCD 240.

Furthermore, it is easy for the surgeon to switch the view field of the scope 401, even while if he or she holds a medical instrument with one hand and another with the other hand, provided the surgeon has already pushed the button on the switch 438. The view field of the scope 401 is automatically changed as he or she moves the distal end of the forceps 411 to any desired position in the peritoneal cavity. The surgeon need not to instruct an assistant to move the endoscope 401 in order get the view field of the endoscope 410 located at a desired position, and the assistant need not keep holding the scope 401. This helps to increase the efficiency of the endoscope surgery.

Even if the distal end of the forceps 411 is located outside the view field of the TV camera 415, the tracking of the forceps 411 can be quickly resumed. Once the second switch 458a is pushed, the zoom lens mechanism 451 is driven, expanding the view field into a wide-angle view field until the image of the distal end appears on the screen of the display monitor 439. The distal end of the forceps 411 can then be tracked again.

An endoscope surgery system according to the fourteenth embodiment of the present invention will be described, with reference to FIGS. 37A and 37B. FIG. 37A shows the TV camera 415 incorporated in this endoscope surgery system.

The TV camera 415 is identical to its counterpart of the tenth embodiment, except that the base 429 of the CCD 420 is secured to the upper surface of the bottom 461 of the second component chamber 418 provided in the casing 416.

The first component chamber 417 provided in the casing 416 contains optical elements 419 (e.g., a lens, a prism, a mirror, a zoom lens and the like). The second component chamber 418 contains a movable lens unit 462 and a lens-driving mechanism 463. The lens unit 462 can be moved by the mechanism 463, along two axes extending at right angles to each other in a plane perpendicular to the optical axis of the TV camera 415. For example, the mechanism 462 moves the lens unit 462 upwards and downward, and to the left and the right.

The movable lens unit 462 comprises a focusing lens 464 and a lens frame 465. The focusing lens 464 is arranged between the optical elements 419 and the CCD 420. The lens frame 465 holds the focusing lens 464.

As shown in FIG. 37B, the lens-driving mechanism 463 comprises two rectangular frames 466a and 466b, a set of four rollers 467a, and another set of four rollers 467b. Supported by the rollers 467a, the first frame 466a can move to the left and the right. Supported by the rollers 467b, the second frame 466b can move up and down.

A first pin 468a protrudes from the upper side of the first frame 466a and is loosely fitted in the helical groove of a feed screw 470a. The feed screw 470a is connected to the shaft of a first stepping motor 469a. When the first stepping motor 469a is driven, rotating the feed screw 480a, the first pin 468a is moved linearly. As a result, the first frame 466a is moved to the left or the right.

A second pin 468b protrudes from the right side of the second frame 466b and is loosely fitted in the helical groove of a feed screw 470b. The feed screw 470b is connected to the shaft of a second stepping motor 469b. When the second stepping motor 469b is driven, rotating the feed screw 480b, the second pin 468b is moved linearly. The second frame 466b is thereby moved upwards and downwards.

The lens frame 465 of the movable lens unit 462 is fitted in the overlapping parts of the rectangular openings of the frames 466a and 466b. A leaf spring 471 is interposed between the lens frame 465 and the first frame 466a. Because of the force applied to it by the spring 471, the lens frame 465 abuts on the partition 428 and set in sliding contact therewith.

When the stepping motors 469a and 469b are driven, the frames 466a and 466b are moved, moving the focusing lens 464 (i.e., an optical element for picking up an image). Thus, the stepping motors 469a and 469b constitute an actuator 433 for switching the view field of the TV camera 415.

Except for the internal structure of the TV camera 415, the fourteenth embodiment is identical to the tenth embodiment. The components similar or identical to those of the tenth embodiment are denoted at the same reference numerals in FIGS. 37A to 37B, and will not be described in detail.

The endoscope surgery system is used, with the TV camera 415 attached to the ocular section 403 of the scope 401. The light applied through the ocular lens 405 provided in the ocular section 403 travels through the optical elements 419 contained in the first component chamber 417 and the focusing lens 464 provided is in the movable lens unit 462. It is projected onto the light-receiving surface of the CCD 420, forming thereon an optical image provided by the scope 401.

When the lens-driving mechanism 463 drives the movable lens unit 462, the focusing lens 464 on the unit 462 is moved along two axes extending at right angles to each other, in a plane perpendicular to the optical axis of the TV camera 415. For example, the focusing lens 464 is moved upwards or downwards and to the left or the right. The view field of the TV camera 415 is thereby switched in the same manner as in the tenth embodiment.

As in the tenth embodiment, the forceps-tracking device 437 keeps tracking the distal end of the forceps 411 while the switch 438 remains depressed. Hence, as the surgeon moves the forceps 411, moving the tongs 413 to a desired position, the view field of the TV camera 415 is switched such that the image of the tongs 413 appears in the center part of the monitor screen. As the surgeon moves the tongs 413 to a desired position, the view field of the scope 401 is automatically switched such that the tongs 413 is displayed in the center part of the screen of the display monitor 439. As the view field is switched, the scope 401 is not moved at all as in the tenth embodiment. The fourteenth embodiment can, therefore, achieves the same advantage as the tenth embodiment.

Further, the wiring board connected to the CCD 420 is not moved since the base 429 of the CCD 420 is secured to the upper surface of the bottom 461 of the second component chamber 418 provided in the casing 416. The wiring board is therefore more durable than the flexible printed wiring board 434 connected to the CCD 420 in the tenth embodiment and which is repeatedly bent as the CCD 420 is moved frequently.

Another endoscope surgery system, which is the fifteenth embodiment of this invention, will be described with reference to FIG. 38A.

The fifteenth embodiment is a first modification of the fourteenth embodiment shown in FIGS. 37A and 37B. It is characterized by the use of an optical adapter 481. The adapter 481 is arranged between the ocular section 403 of the scope 401 and the TV camera 415 containing a CCD 420. The optical adapter 481 comprises an optical element 419, a movable lens unit 462, and a lens-driving mechanism 463. The unit 462 and the mechanism 463 are identical to their counter-parts incorporated in the fourteenth embodiment.

To the optical adapter 481, the scope 401 and the TV camera 415 are removably coupled together. The scope 401 can therefore be easily disconnected from the TV camera 415. The scope 401, which is a direct-view type scope, can easily be replaced by a scope of a different type having a different view angle, such as a slant-view type rigid scope. Once disconnected from each other, the scope 401 and the TV camera 415 can be sterilized independently. Thus, the scope 401 which is inserted in part into a body cavity, may be sterilized in an autoclave, whereas the TV camera 415 containing electronic devices (e.g., the CCD 420) which will become less durable if sterilized may be subjected EOG sterilization less moderate than autoclave sterilization.

Still another endoscope surgery system, which is the sixteenth embodiment of the invention, will be described with reference to FIG. 38B.

The sixteenth embodiment is a second modification of the fourteenth embodiment shown in FIGS. 37A and 37B. It is characterized in two respects. First, the movable lens unit 462 and the lens-driving mechanism 463 are arranged in the ocular section 403 of the scope 401. Second, the CCD 420 is located in the TV camera 415 connected to the ocular section 403, as in the fifteenth embodiment. The sixteenth embodiment has the same advantages as the fifteenth embodiment.

Figures 39A, 39B:
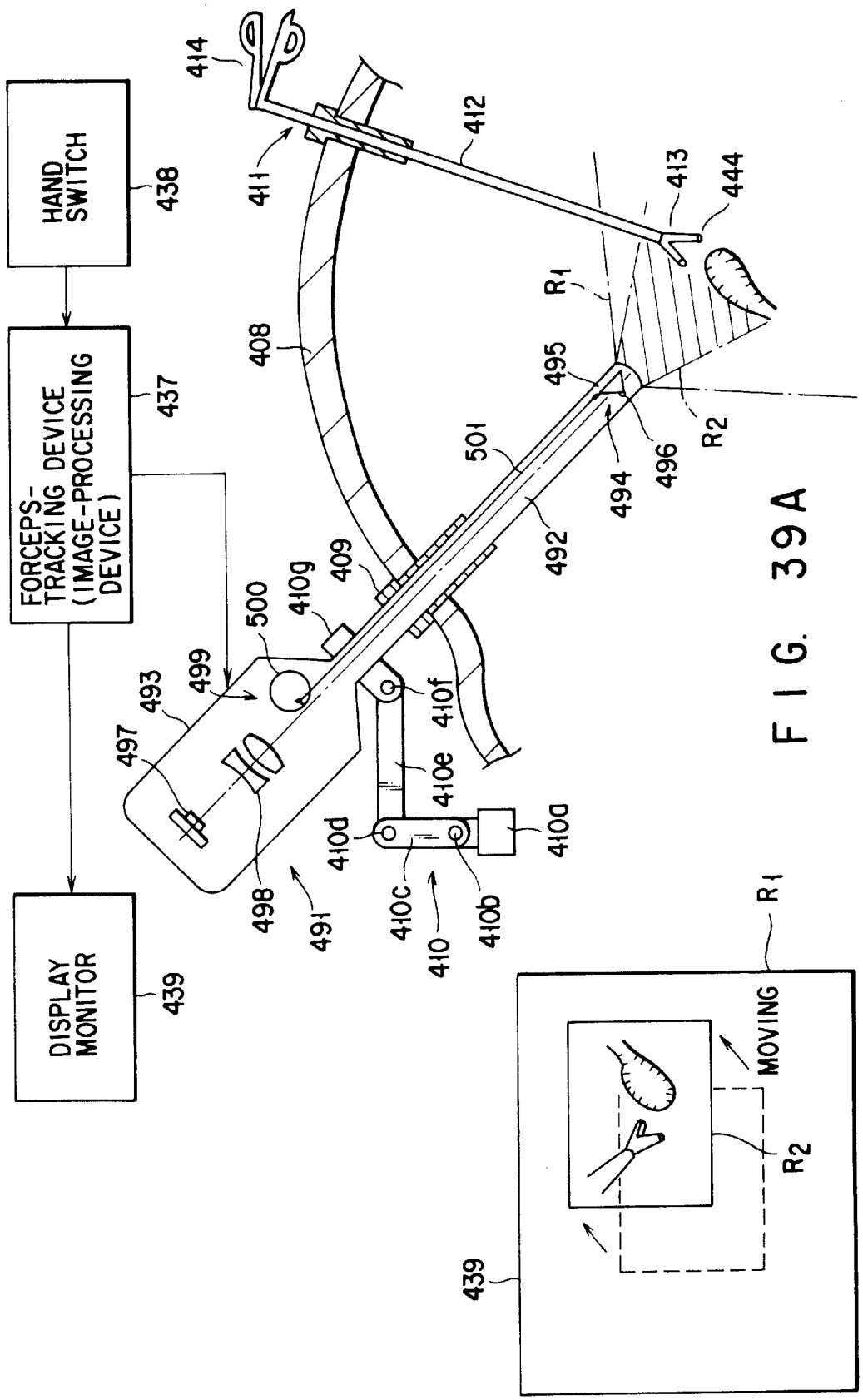
FIG. 39A is a diagram showing an endoscope surgery system according to a seventeenth embodiment of this invention.
FIG. 39B is a front view of the TV monitor provided in the seventeenth embodiment.

An endoscope surgery system according to the seventeenth embodiment of the present invention will be described, with reference to FIGS. 39A and 39B.

The seventeenth embodiment is characterized in that an electronic endoscope 491 is used. As shown in FIG. 39A, the electronic endoscope 491 comprises an insertion section 492 and an operation section 493. The operation section 493 is connected to the proximal end of the insertion section 492.

To perform endoscope surgery by using this system, the insertion section 492 is inserted into the peritoneal cavity of the patient through a trocar 409 set in an opening incised in the abdominal wall 408. The operation section 493 is movably held by a three-joint scope holder 410 of the same type employed in the tenth embodiment shown in FIG. 27A. A pair of forceps 411 is inserted into the peritoneal cavity through a trocar set in another opening incised in the abdominal wall 408.

In the distal end portion of the insertion section 492 there is provided an objective optical system 494. The objective optical system 494 has a prism 495 and a pin 496. The prism 495 is supported by the pin 496 and can rotate around the pin 496. The operation section 493 comprises a CCD 497, a focusing optical system 498, and a prism-operating unit 499. The CCD 497 is a solid-state image pickup device. The focusing optical system 498 is provided to receive the light applied through the prism 495 of the objective optical system 494 and forms an optical image on the light-receiving surface of the CCD 497. The prism-operating unit 499 is designed to rotate the prism 495 of the objective optical system 494.

A disc 500 is connected to the prism-operating unit 499. The disc 500 can be rotated by an actuator (not shown) such as a stepping motor. An operation rod 501 is connected at one end to the disc 500, and at the other end to the prism 495. When the disc 500 is rotated by the actuator, the operation rod 501 is moved along its axis. The prism 495 is thereby rotated around the pin 496 to switch the view field $R_2$ of the objective optical system 494 of the electronic endoscope 491.

The region $R_1$ in which the view field $R_2$ can be switched is defined by the window at the distal end of the insertion section 492. Needless to say, the view field $R_2$ is smaller than the region $R_1$. An optical image of any object present in the view field $R_2$ is supplied via the prism 495 to the focusing optical system 498 and finally formed on the light-receiving surface of the CCD 497.

A forceps-tracking device 437 of the same type as utilized in the tenth embodiment is connected to the operation section 493 of the endoscope 491. Connected to the forceps-tracking device 437 are a switch 438 and a display monitor 439. The switch 438 is, for example, a foot switch, a hand switch or the like. The display monitor 439 is, for example, an HMD (Head Mounted Display) or the like.

In operation, the light is supplied from the peritoneal cavity to the CCD 497 through the prism 495 and the focusing optical system 498, forming an optical image on the light-receiving surface of the CCD 497. The optical image is of the same size as the view field $R_2$ of the endoscope 491. Hence, it is smaller than the region $R_1$ in which the view field $R_2$ of the endoscope 491 can be switched. The CCD 497 converts the optical image into image data, which is supplied to the display monitor 439. The display monitor 439 displays the image picked up by the electronic endoscope 491.

As in the tenth embodiment, the forceps-tracking device 437 keeps tracking the distal end of the forceps 411 while the switch 438 remains depressed. More specifically, the prism-operating unit 499 is driven, rotating the disc 500 and moving the operation rod 501 along its axis. The prism 495 is thereby rotated around the pin 496, switching the view field $R_2$ of the objective optical system 494 of the electronic endoscope 491.

While the forceps-tracking device 437 is tracking the distal end of the forceps 411, the display monitor 439 displays the tongs 413 connected the distal end of the forceps 411, in the center part of its screen.

The tongs 413 may not be displayed in the center part of the screen of the display monitor 439. If this is the case, the surgeon pushes the button on the switch 438. Then, the CCD-driving mechanism 421 is controlled, moving the CCD 420. The view field of the electronic endoscope 491 is thereby switched, whereby the image of the tongs 413 is displayed in the center part of the screen of the display monitor 439.

As described above, as long as the forceps-tracking device 437 is tracking the distal end of the forceps 411, the prism-driving unit 499 is driven, rotating the prism 495 around the pin 496 and switching the view field $R_2$ of the objective optical system 494. Hence, when the surgeon moves the tongs 413 to a desired position, the view field of the scope 491 is automatically switched such that the tongs 413 is displayed in the center part of the screen of the display monitor 439. As the view field is switched, the scope 401 is not moved at all as in the tenth embodiment. The seventeenth embodiment can, therefore, achieves the same advantage as the tenth embodiment.

An endoscope surgery system according to the eighteenth embodiment of this invention will be described, with reference to FIGS. 40A and 40B. The eighteenth embodiment incorporates a modification of the zoom lens mechanism 451 (FIG. 35A) employed in the thirteenth embodiment.

Figure 40A:
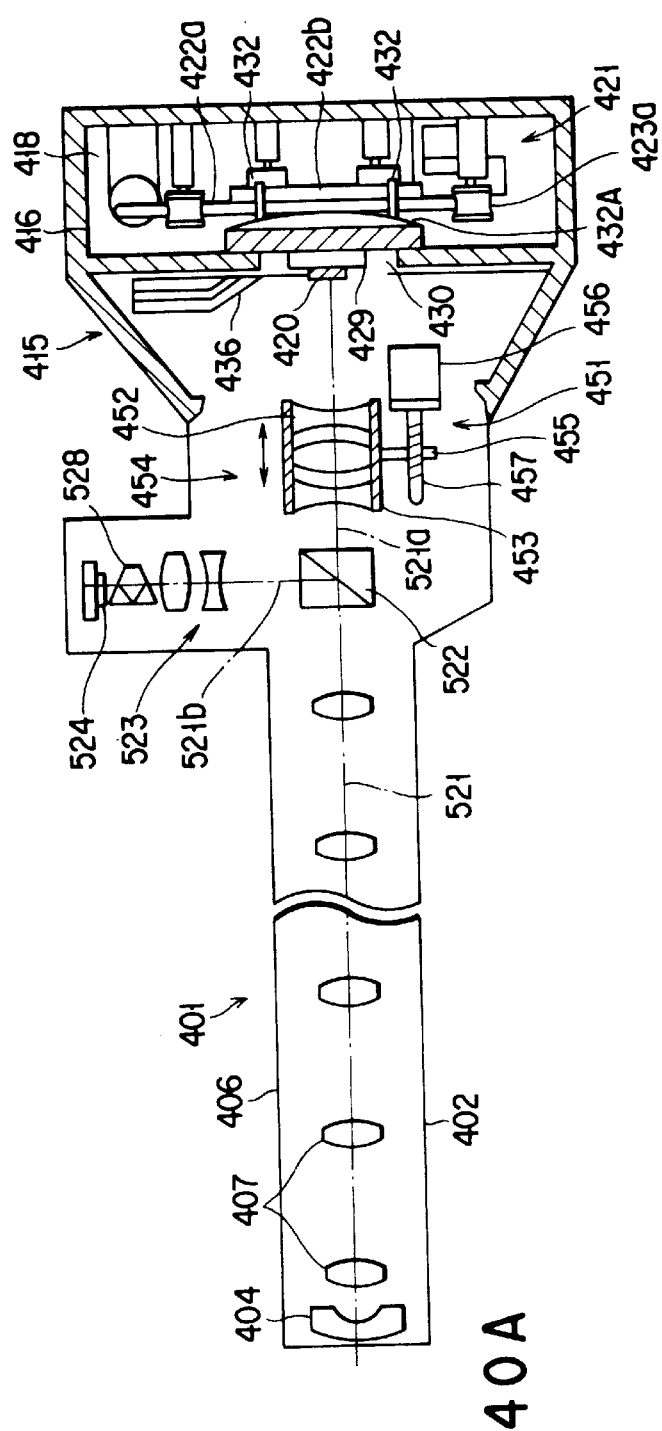
FIG. 40A is a longitudinal sectional view of the scope incorporated in a endoscope surgery system according to an eighteenth embodiment of the present invention.
Figure 40B:
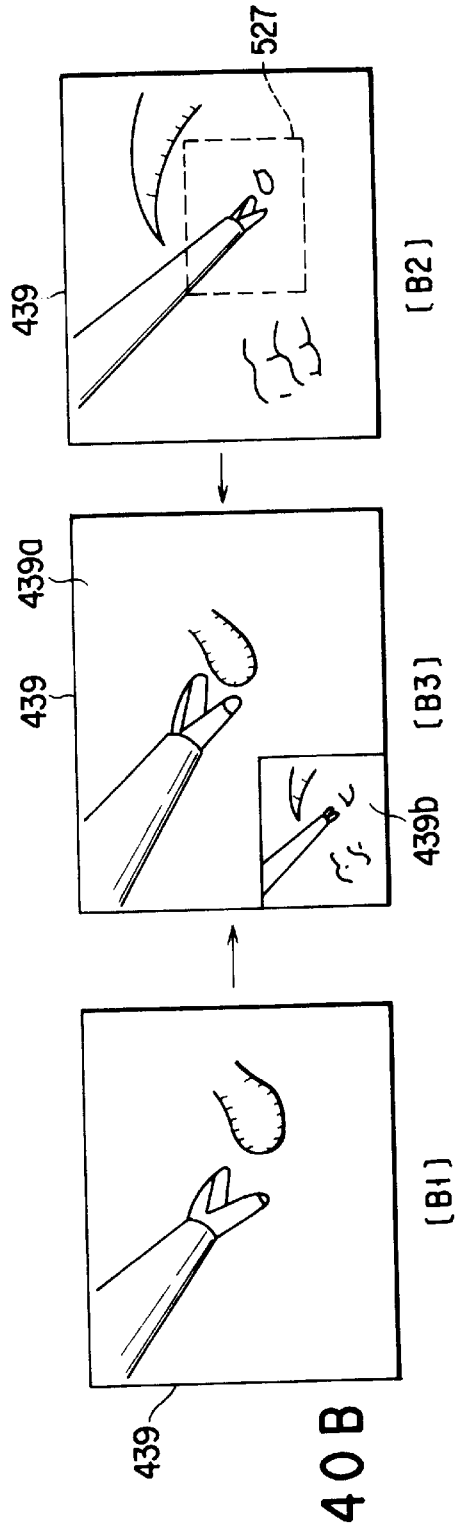
FIG. 40B are front views of the display monitor used in the eighteenth embodiment, explaining how the view field of the scope is switched.

As shown in FIG. 40A, the eighteenth embodiment has a scope 401 incorporating a zoom lens mechanism 451, and a TV camera 415 formed integral with the scope 401. The scope 401 has an image-supplying path 521 and a beam splitter 522 provided in the path 521. The beam splitter 522 is arranged at the input of a zoom lens unit 454. It splits a light beam supplied along the image-supplying path 521 into two beams and distributes the beams to a first branch path 521a and a second branch path 521b. The second branch path 521b extends substantially at right angles to the first branch path 521a. The optical image input to the scope 401 is supplied toward a zoom lens 452 through the first branch path 521a.

A first CCD 420 is arranged in the first branch path 521a. The optical image supplied along the first branch path 521a is projected as a narrow-angle image onto the first CCD 420 through the zoom lens 452. The first CCD 240 converts the narrow-angle image into a video signal, which is supplied to a display monitor 439. The monitor 349 displays an image B1 as shown in FIG. 40B.

A wide-angle lens unit 523, an image-inverting prism 528 and a second CCD 524 are provided in the second branch path 521b. The wide-angle lens unit 523 magnifies the optical image supplied from the beam splitter 522. The image-inverting prism 528 inverts the optical image supplied from the wide-angle lens unit 523. The inverted image is projected as a wide-angle image onto the second CCD 524. The second CCD 524 converts the wide-angle image into a video signal, which is supplied to the display monitor 439. The monitor 439 displays an image B2 as shown in FIG. 40B.

The scope 401 is removably attached to the TV camera 415 (not shown). The scope 401 can therefore be easily disconnected from the TV camera 415. The scope 401, which is a direct-view type scope, can easily be replaced by a scope of a different type having a different view angle, such as a slant-view type rigid scope. The optical unit including the second CCD 524 can be removed from the TV camera 415.

Figure 41:
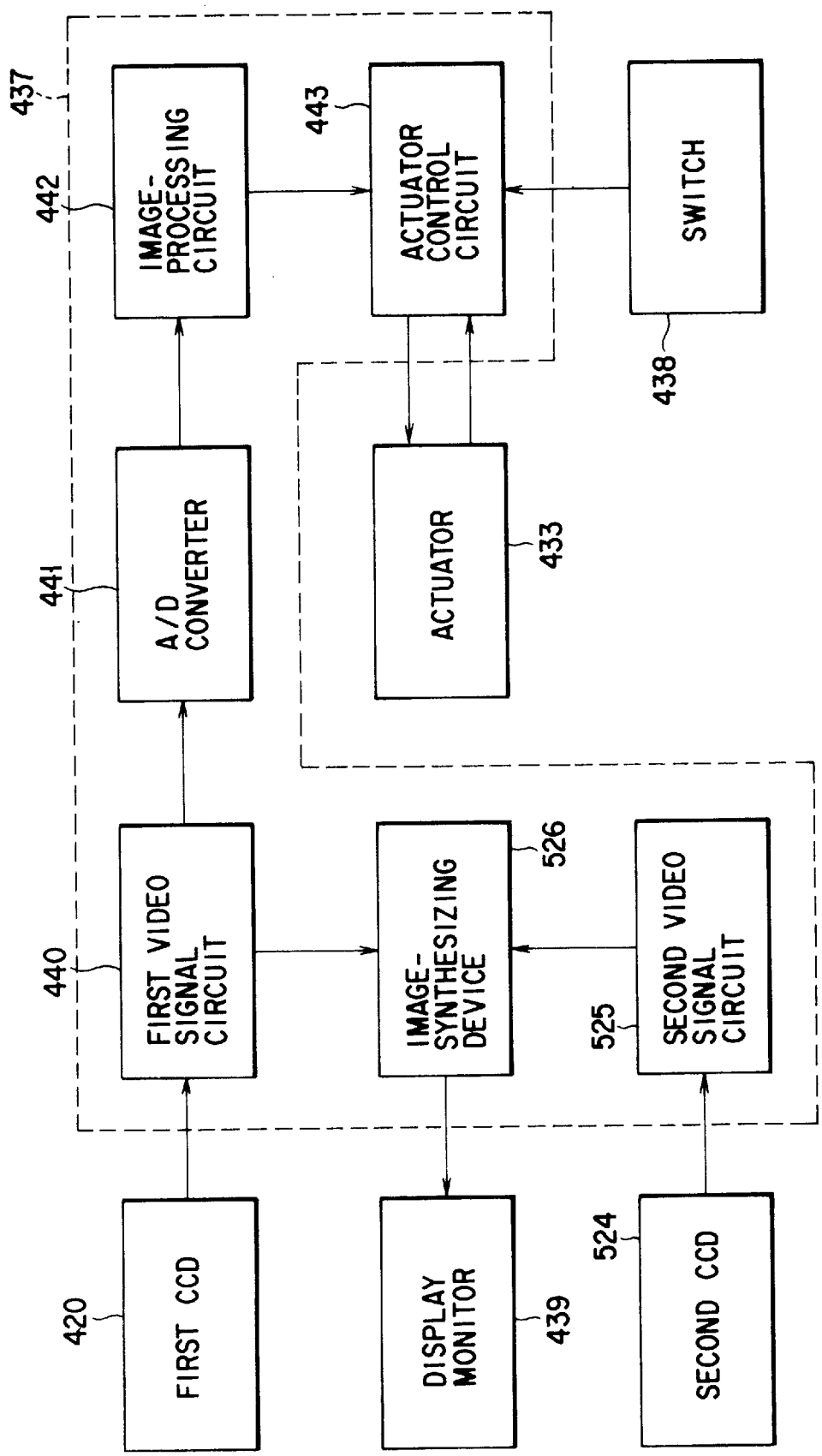
FIG. 41 is a block diagram illustrating the control means incorporated in the eighteenth embodiment and designed to switch the view field of the scope.
Figures 48A, 48B, 48C:
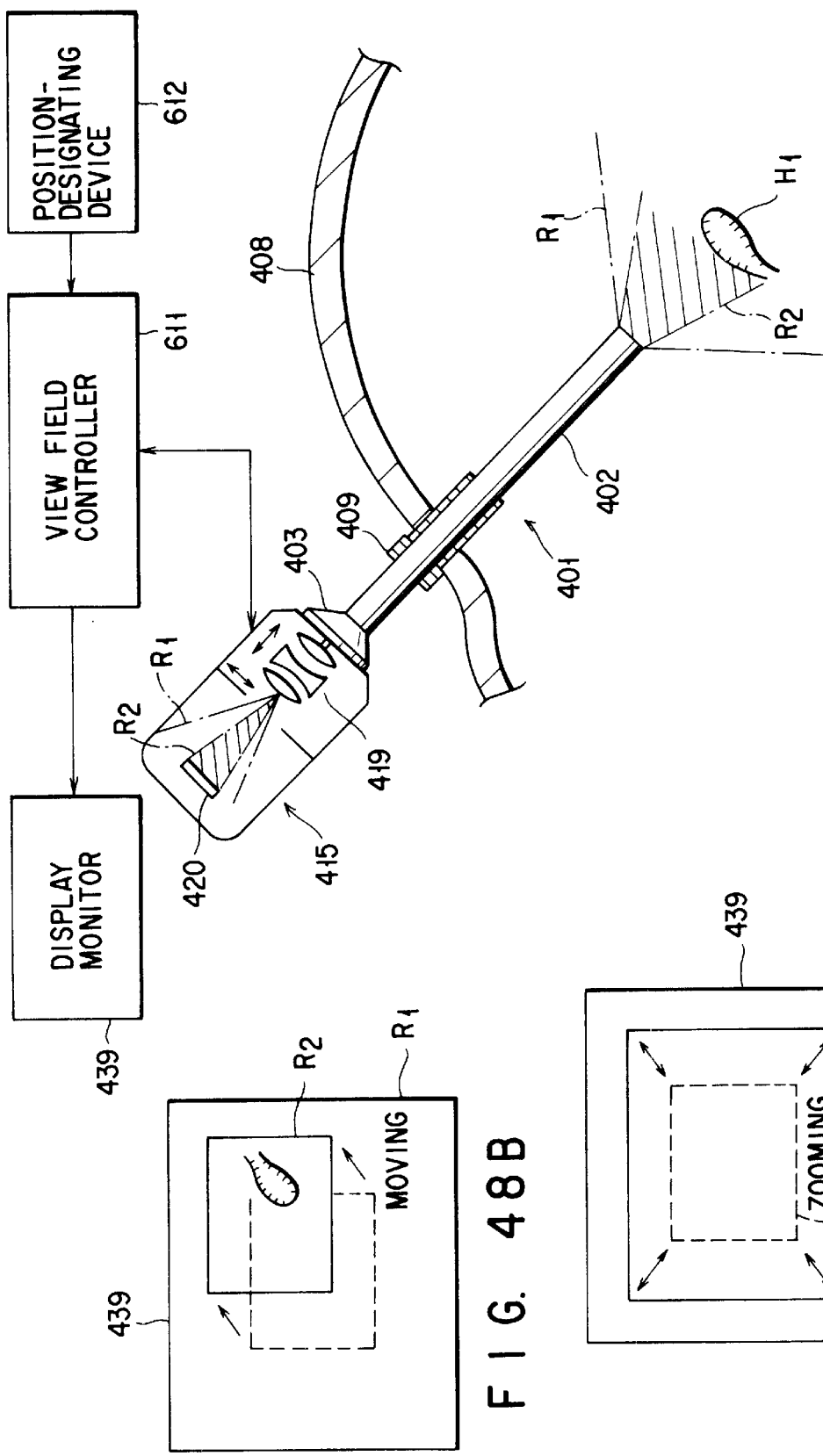
FIG. 48A is a diagram showing an endoscope surgery system according to a twenty-fourth embodiment of this invention.
FIG. 48B is a front view of the TV monitor provided in the twenty-fourth embodiment, explaining how the monitor displays an image of an instrument and an image of a tissue as the endoscope tracks the instrument.
FIG. 48C is a front view of the TV monitor shown in FIG. 34B, explaining how the monitor displays an image of an instrument and an image of a tissue as the endoscope performs zooming operation.

As shown in FIG. 41, the forceps-tracking device 437 comprises a first video signal circuit 440, an A/D converter 441, an image-processing circuit 442, an actuator control circuit 443, a second video signal circuit 525, and a image-synthesizing device 526. The first video signal circuit 440 is connected to the first CCD 420 which is provided in the first branch path 521a. The second video signal circuit 525 is connected to the second CCD 524 which is provided in the second branch path 521b.

The first video signal circuit 440, the second video signal circuit 525 and the display monitor 439 are connected to the image-synthesizing device 526. A video signal generated by the first CCD 420 is supplied to the first video signal circuit 440, and a video signal generated by the second CCD 524 is supplied to the second video signal circuit 525. Either video signal circuit converts the input video signal a video signal such as an NTSC signal or an RGB signal. The video signals generated by the video signal circuits 440 and 525 are supplied to the image-synthesizing device 526.

The image-synthesizing device 526 synthesizes the input video signals, producing a composite video signal. The composite video signal is supplied to the display monitor 439, which displays a composite image B3. As shown in FIG. 40B, the composite image B3 consists of a narrow-angle image B1 picked up by the first CCD 420 and a wide-angle image B2 picked up by the second CCD 524.

A push button and an image-switching button (either not shown) are provided on the switch 438. When the image-switching button is operated, the image displayed on the monitor 439 is switched among the narrow-angle image B1, the wide-angle image B2 and the composite image B3. When the wide-angel image B2 is displayed, a broken-line rectangle 527 is displayed, indicating the region of the narrow-angle image B1.

How the eighteenth embodiment operates will now be described.

First, the surgeon pushes the push button on the switch 438, activating the forceps-tracking device 437. As long as the push button remains depressed, the device 437 keeps operating to track the distal end of the forceps 411. The device 437 determines the position of the distal end of the forceps 411 from the wide-angle image B2 picked up by the second CCD 524 arranged in the second branch path 521b. It also determines, from the narrow-angle image B1 picked up by the first CCD 420 arranged in the fist branch path 521a, how much stepping motors 426a and 426b (i.e., an actuator 433 for a CCD-driving mechanism 421) have been driven to display the distal end of the forceps 411 in the center part of the screen of the monitor 439.

The actuator control circuit 443 incorporated in the forceps-tracking device 437 controls the actuator 433 of the CCD-driving mechanism 421. Thus controlled, the actuator 433 moves the first CCD 420. The view field of the scope 401 is thereby switched to track the distal end of the forceps 411. The tongs 413 attached to the distal end of the forceps 411 are thereby displayed, substantially in the center part of the screen of the display monitor 439.

The tongs 413 may not be displayed in the center part of the screen of the display monitor 439. In this case, the surgeon pushes the button on the switch 438. Then, the CCD-driving mechanism 421 is controlled, moving the CCD 420. The view field of the TV camera 415 is thereby switched, whereby the image of the tongs 423 is moved at a prescribed speed to the center part of the screen of the display monitor 439.

The surgeon may then push the image-switching button on the switch 438 to switch the image displayed on the display monitor 439, among the narrow-angle image B1, the wide-angle image B2 and the composite image B3.

The endoscope surgery system according to the eighteenth embodiment is advantageous in the following respects.

First, the surgeon can easily switch the view field of the scope 401, even while holding a medical instrument (e.g., the forceps 411) with one hand and another with the other hand, provided he or she has already pushed the button on the switch 438 to activate the forceps-tracking device 437. That is, the view field of the scope 401 is automatically switched as the surgeon moves the distal end of the forceps 411 to any desired position in the peritoneal cavity.

Further, the surgeon need not to instruct an assistant to move the endoscope 401 in order get the view field of the endoscope 401 located at a desired position, and the assistant need not keep holding the scope 401.

In addition, the scope 401 is not moved at all as the view field is switched, not bothering the surgeon manipulating the forceps 411 or inflicting pain on the part of the patient. This serves to increase the efficiency of the endoscope surgery.

As mentioned above, the display monitor 439 can simultaneously display the wide-angle image and the narrow-angle image. Observing the narrow-angle image (i.e., the magnified image) of the affected tissue, the surgeon can apply intricate treatment on the tissue. Seeing the wide-angle image, the surgeon can understand the conditions of the unaffected tissues located near the affected tissue and can therefore take precautions against possible damages to the unaffected tissues. Even if the image of the tongs 413 moves out of the narrow-angle image region 527, the surgeon can quickly locate the tongs 413 in the wide-angle image.

Furthermore, this endoscope surgery system can be provided at a relatively low cost. This is because the CCD-driving mechanism 421 for switching the view field of the endoscope 401 is less expensive than a mechanism which moves the endoscope 401 to switch the view field thereof.

Since the pixels of the CCD 420 are arranged in high density on the light-receiving surface of the TV camera 415, the image displayed by the display monitor 439 can have high quality.

Still further, the flexible printed wiring board 434 is durable since its middle portion 436 is bend in the form of letter U, though the printed wiring board 434 is repeatedly bent as the CCD 420 is moved.

Another endoscope surgery system, which is the nineteenth embodiment of the invention, will be described with reference to FIGS. 42A, 42B and 42C. This embodiment comprises a scope 401 and a TV camera 415, both of the types used in the tenth embodiment. It is characterized by a optical path 531 which has a specific structure for supplying an optical image.

As seen from FIG. 42A, the optical path 531 consists of a main optical path 531a and an auxiliary optical path 531b. These paths 531a and 531b extend parallel to each other. The main optical path 531a extends between an objective lens 404 and a CCD 420, both incorporated in the scope 401. A path-switching mechanism 532 is provided in the main optical path 531a. The mechanism 532 has two path-switching mirrors 533 and 534, which are spaced apart along the main optical path 531a. A wide-angle lens unit 535 is arranged in the main optical path 531a and located between the path-switching mirrors 533 and 534, for converting the optical image provided by the scope 401 to a wide-angle image.

As shown in FIG. 42A, the front path-switching mirror 533 located in front of the wide-angle lens unit 535 can be rotated around a support rod 536 between first and second positions indicated by broken lines and solid lines, respectively. When rotated to the first position, the front path-switching mirror 533 opens the main optical path 531a. When rotated to the second position, the front path-switching mirror 533 closes the main optical path 531a. The rear path-switching mirror 534 located at the rear of the wide-angle lens unit 535 can be rotated around a support rod 537 between first and second positions indicated by broken lines and solid lines, respectively. When rotated to the first position, the rear path-switching mirror 534 opens the main optical path 531a. When rotated to the second position, the rear path-switching mirror 534 closes the main optical path 531a. Both the front path-switching mirror 533 and the rear path-switching mirror 534 are simultaneously rotated by an optical path switching actuator (not shown) which is, for example, an electromagnetic coil.

As illustrated in FIG. 42A, two mirrors 538 and 538 are fixed in place at the input and output ends of the auxiliary optical path 531b, respectively. The front fixed mirror 538 opposes the front path-switching mirror 533 and spaced apart therefrom. The rear mixed mirror 539 opposes the rear path-switching mirror 534 and spaced apart therefrom. A narrow-angle lens 540 is arranged in the auxiliary optical path 531b and located between the fixed lenses 538 and 539, for converting the optical image provided by the scope 401 to a wide-angle image.

The nineteenth embodiment comprises a forceps-tracking device 437, a switch unit 438, and a display monitor 439, all being the same type as those used in the thirteenth embodiment (FIGS. 34A to 34C). The forceps-tracking device 437 is connected at its input to the TV camera unit 415 and at its output to the display monitor 439. The switch unit 438 is connected to the forceps-tracking device 437.

The switch unit 438 has three switches 458a, 458b and 458c. The first switch 458a is provided to activate and deactivate the forceps-tracking device 437. The second switch 438b and the third switch 458c are provided to drive the optical path switching actuator (not shown). When the second switch 458b is pushed, the actuator rotates both path-switching mirrors 533 and 534 to the first position indicated by broken lines. The optical image picked up by the scope 401 is thereby supplied to the CCD 420 through the wide-angle lens unit 535 set in the main optical path 531a. The CCD 420 receives the wide-angle image output by the lens unit 535 and converts it into a video signal. The video signal is supplied to the display monitor 439 via the forceps-tracking device 437. The monitor 439 displays a wide-angle image, as shown in FIG. 42B.

When the third switch 458c is pushed, the actuator rotates both path-switching mirrors 533 and 534 to the second position indicated by solid lines. The optical image is thereby supplied to the CCD 420 through the narrow-angle lens 540 placed in the auxiliary optical path 531b. The CCD 420 receives the narrow-angle image output by the narrow-angle lens 540 and converts it into a video signal. The video signal is supplied to the display monitor 439 via the forceps-tracking device 437. The monitor 439 displays a narrow-angle image, as shown in FIG. 42C.

The distal end of the forceps 411 may not be displayed in the center part of the screen of the display monitor 439. To see the distal end of the forceps 411 on the monitor screen, the surgeon pushes the second switch 458b. Both path-switching mirrors 533 and 534 are thereby rotated to the first position. As a result, the display monitor 439 displays the wide-angle image, as is illustrated in FIG. 42B. Then, the surgeon pushes the first switch 458a on the switch unit 438, thus activating the forceps-tracking device 437. The image of the distal end of the forceps 411 is thereby moved to the center part of the monitor screen.

With the nineteenth embodiment, as with the thirteenth embodiment, it is sufficient for the surgeon to push the second switch 458b and the first switch 458a in this order, to switch the narrow-angle image to the wide-angle image and then to automatically move the image of the distal end of the forceps 411 to the center part of the screen of the display monitor 439.

An endoscope surgery system according to the twentieth embodiment of the present invention will be described, with reference to FIGS. 43 and 44.

The twentieth embodiment has a scope 401 and a TV camera 415 connected to the scope 401. The scope 401 is of the same type as its counterpart of the tenth embodiment. The TV camera 415 contains a CCD-driving mechanism 421 which differs in structure from its counterpart of the tenth embodiment.

As shown in FIG. 43, the CCD-driving mechanism 421 has two U-shaped arms 551 and 552. The first arm 551 is connected at one end to the shaft of a first stepping motor 553. As seen from FIG. 44, the shaft of the first stepping motor 553 extends at right angles to the optical axis of the scope 401. The other end of the first arm 551 is coupled to the casing 416 of the TV camera 415 and can rotate around a pin 554. The second arm 552 is connected at one end to the shaft of a second stepping motor 555. As seen from FIG. 44, the shaft of the second stepping motor 554 extends at right angles to the shaft of the first stepping motor 553, in a plane perpendicular to the optical axis of the scope 401. The other end of the second arm 552 is coupled to the casing 416 and can rotate around a pin 556. Hence, the arms 551 and 552 can rotate around two axes which extend at right angles to each other and to the optical axis of the scope 401.

The arms 551 and 552 have CCD-guiding slits 557 and 558, respectively. A pin 559 extends through these slits 557 and 558, at the intersection thereof. The pin 559 is secured to a base 560. On the base 560 there is mounted a CCD 420. Hence, the base 560 is moved to the left or the right (FIG. 44) as the first arm 551 is rotated by the first stepping motor 553, and upwards or downwards as the second arm 552 is rotated by the second stepping motor 555. As a result, the CCD 420, which is mounted on the base 560, is moved in a plane perpendicular to the optical axis of the scope 401.

As described above, the stepping motors 553 and 555 are used to move the CCD 420 (i.e., the image pickup device) of the TV camera 415. The stepping motors 553 and 555 constitute an actuator which serves to switch the view field of the TV camera 415. Therefore, the twentieth embodiment can achieve the same advantage as the tenth embodiment.

An endoscope surgery system according to the twenty-first embodiment of the invention will be described, with reference to FIG. 45. This embodiment is identical to the tenth embodiment, except for the internal structure of the TV camera 415.

More specifically, as shown in FIG. 45, the TV camera 415 contains two prisms 571a and 571b. A nut 572a is secured to one side of the first prism 571a, and a nut 572b to one side of the second prism 571b. The first prism 571a is positioned in the extension of the optical axis of a scope 401.

A lens 573 is located between the ocular section 403 of the scope 401 and the first prism 571a. The lens 573 is supported by a lens frame 574. A strip 575 protrudes from the lens frame 574. The strip 575 has a screw hole, in which a screw 577 is set. The screw 577 is connected to the shaft of a stepping motor 576. Thus, when the stepping motor 576 is driven, the lens 573 is moved along the optical axis of the scope 401.

The nut 572a connected to the first prism 571a is set in engagement with a first screw 579, which is connected to the shaft of a first prism-driving stepping motor 578. When the stepping motor 578 is driven, the first screw 579 is rotated, whereby the first prism 571a is moved back or forth, along the optical axis of the scope 401.

The second prism 571b is arranged below the first prism 571a to receive the optical image supplied from the lens 573 and reflected from the first prism 571a. A CCD 420 is arranged beside the second prism 571b to receive the optical image reflected from the second prism 571b.

The nut 572b connected to the second prism 571b is set in engagement with a second screw 581, which is connected to the shaft of a second prism-driving stepping motor 580. When the stepping motor 580 is driven, the second screw 581 is rotated, whereby the second prism 571b is moved up or down, along the path in which the optical image is supplied from the first prism 571a.

As the first and second prisms 571a and 571b are moved, the lens 573 is moved along the optical axis of the scope 401, preventing the length of the optical path between the lens 573 and the CCD 420 from changing. The light input to the lens 573 is a parallel beam, and the CCD 420 is held in place at the focal distance of the lens 573.

The operation of the twenty-first embodiment will now be explained.

When first prism-driving stepping motor 578 is driven, the first prism 571a is moved along the optical axis of the TV camera 415. The optical image is thereby moved to the left or right (FIG. 45) on the light-receiving surface of the CCD 420. When the second prism-driving stepping motor 580 is driven, the second prism 571b is moved up or down. The optical image moves upwards or downwards (FIG. 45) on the light-receiving surface of the CCD 420. Thus, the view field of the TV camera 415 is switched.

The first prism-driving stepping motor 578 and the second prism-driving stepping motor 580 constitute an actuator 433 to switch the view field of the TV camera 415. As long as the forceps-tracking device 437 (not shown in FIG. 45) remains activated, the view field of the TV camera 415 is switched to track the distal end of the forceps 411 (not shown) in the same way as in the tenth embodiment. Thus, the twenty-first embodiment can achieve the same advantage as the tenth embodiment.

Another endoscope surgery system, which is the twenty-second embodiment of the invention, will be described with reference to FIG. 46.

The twenty-second embodiment is identical to the twenty-first embodiment shown in FIG. 45, except for two respects. First, two rotatable mirrors 591a and 591b are incorporated in the TV camera 415, in place of the movable prisms 571a and 571b. Second, a zoom lens 593 is utilized instead of the lens 573.

As illustrated in FIG. 46, the first mirror 591a is positioned in the extension of the optical axis of a scope 401. The zoom lens 593 is located between the ocular section 403 of the scope 401 and the first mirror 591a. The zoom lens 593 is supported by a lens frame 593. A strip 595 protrudes from the lens frame 574 and has a screw hole. A screw 597 is set in the screw hole and connected to the shaft of a stepping motor 596. Thus, when the stepping motor 596 is driven, the zoom lens 593 is moved along the optical axis of the scope 401.

The first mirror 591*a* is fastened to the shaft of a first mirror-rotating stepping motor 598. The second mirror 591*b* is located below the first mirror 591*a* and connected to the shaft of a second mirror-rotating stepping motor 599. The mirrors 591*a* and 591*b* can be rotated by the stepping motors 598 and 599, respectively. The first mirror 591*a* is inclined, usually at about 45°, and reflects an input beam downwards at about 90°, supplying the beam to the second mirror 591*b*. The second mirror 591*a* is inclined, usually at about 45°, and reflects the beam sideways at about 90°, applying the beam on to the light-receiving surf ace of a CCD 420.

The operation of the twenty-second embodiment will now be explained.

When first mirror-rotating stepping motor 598 is driven, the first mirror 591*a* is rotated. The optical image is thereby moved to the left or right (FIG. 46) on the light-receiving surface of the CCD 420. When the second mirror-rotating stepping motor 599 is driven, the second mirror 591*b* is rotated. The optical image is thereby moved upwards or downwards (FIG. 46) on the light-receiving surface of the CCD 420. Thus, the view field of the TV camera 415 is switched. Further, when the stepping motor 596 is driven, the lens frame 594 is moved back and forth, along the optical axis of the scope 401, thus moving the zoom lens 593 in the same direction. As a result, the optical image formed on the light-receiving surface of the CCD 420 is enlarged or reduced.

The first mirror-rotating stepping motor 598 and the second mirror-rotating stepping motor 599 constitute an actuator 433 to switch the view field of the TV camera 415. While the forceps-tracking device 437 (not shown in FIG. 45) remains activated, the view field of the TV camera 415 is switched to track the distal end of the forceps 411 (not shown) in the same way as in the tenth embodiment. Thus, the twenty-second embodiment can achieve the same advantage as the tenth embodiment.

An endoscope surgery system according to the twenty-third embodiment of the present invention will be described, with reference to FIGS. 47A and 47B.

The twenty-third embodiment is identical to the tenth embodiment, except that an organ-tracking device 602 is utilized in place of the forceps-tracking device 437. As shown in FIG. 47A, a color or shape marker 601 is mounted on an organ $H_1$ present in the peritoneal cavity of a patient. While activated, the organ-tracking device 602 keeps tracking the marker 601 provided on the organ $H_1$, determines the shape of the organ $H_1$, and performs pattern matching. Based on the results of the pattern matching, the device 602 moves the CCD 420 provided in a TV camera 415 such that the organ $H_1$ is displayed in the center part of the screen of a display monitor 439 connected to the organ-tracking device 602.

An endoscope surgery system according to the twenty-fourth embodiment of the present invention will be described, with reference to FIGS. 48A, 48B, 48C and 49.

The twenty-fourth embodiment is similar to the eleventh embodiment, but different in three respects. First, it has a view field controller 611 instead of the forceps-tracking device 437. Second, it has a position-designating device 612 instead of the switch 438. Third, it uses an HMD 613 in place of the TV monitor 439.

As shown in FIG. 49, the HMD 613 is mounted on the surgeon's head $H_2$. The position-designating device 612 comprises a sense coil 614 and a source coil 615. The sense coil 614 is secured to the HMD 613. Alternatively, the sense coil 614 may be held on the surgeon's head $H_2$ by means of a headband. The source coil 615 is held at a specific position in the endoscope surgery system. The sense coil 614 and the source coil 615 have three coil elements each, which are wound around three axes (X axis, Y axis, and Z axis) intersecting at right angles to one another. The position-designating device 612 further comprises a position sensor (not shown) which determines the positional relationship between the coils 614 and 615 from the mutual inductance thereof. The position sensor outputs a control signal which represents the position of the surgeon's head $H_2$. The control signal is supplied to the view field controller 611.

The view field controller 611 switches, enlarges or reduces the view field of a scope 401, in accordance with the control signal supplied from the position-designating device 612. As the surgeon D moves his or her head $H_2$ upwards, downwards, to the left, or to the right, the HMD 613 displays an image of an object which is located in front of the surgeon's eyes. When the surgeon D moves his or head $H_2$ forward, the image displayed by the HMD 613 is enlarged. When the surgeon D moves his or her head $H_2$ backwards, the image is reduced.

The surgeon D need not do anything, but move his or her head $H_2$, to switch, enlarge and reduce the view field of the scope 401. The view field controller 611 does accomplish this task in accordance with the control signal which has been generated by the position-designating device 612 and which represents the position of the surgeon's head $H_2$.

An endoscope surgery system according to the twenty-fifth embodiment of the invention will be described, with reference to FIG. 50. This embodiment is a first modification of the twenty-fourth embodiment shown in FIG. 48A, 48B and 48C and 49. As shown in FIG. 50, a position sensor 622 is secured to the headband 621 the surgeon D wears. Alternatively, the sensor 622 may be secured to the HMD 613 mounted on the surgeon's head $H_2$. The sensor 622 may be an acceleration sensor or a gyro sensor.

As the surgeon D moves his or her head $H_2$ upwards, downwards, to the left, or to the right, a TV monitor 439 of the same type used in the twenty-fourth embodiment displays an image of an object which is located in front of the surgeon's eyes. When the surgeon D moves his or head $H_2$ forward, the image displayed by the HMD 613 is enlarged. When the surgeon D moves his or her head $H_2$ backwards, the image is reduced.

An endoscope surgery system according to the twenty-sixth embodiment of the invention will be described, with reference to FIG. 51. This embodiment is a second modification of the twenty-fourth embodiment and characterized in that a speech recognition unit 631 is utilized in place of the position-designating device 612. The unit 631 is connected to a microphone 632.

The microphone 632 catches the surgeon's any oral instructions and converts them into a speech signal. The speech signal is supplied to the speech recognition unit 631. The unit 631 generates a control signal from the speech signal and supplies the control signal to a scope control section (not shown). In accordance with the control signal, the control section switches, enlarges or reduces the field view of a rigid scope 401. Thus, the surgeon D can have the view field of the scope 401 controlled as he or she wants, without performing any manual operation.

An endoscope surgery system according to the twenty-seventh embodiment of the invention will be described, with reference to FIG. 52A. The twenty-seventh embodiment is a third modification of the twenty-fourth embodiment. It is characterized in that a remote-control panel 641 is used in place of the position-designating device 612.

The remote-control panel 641 is attached to the operation section of the medical instrument used, the floor of the operating room, or a side of the operating bed. As shown in FIG. 52A, the panel 641 has two sets of buttons. The first set consists of an up-button 642a, a down-button 642b, a left-button 642c, and a right-button 642d. The surgeon may push these buttons 642a, 642b, 642c and 642c to move the image upwards, downwards, leftward and rightward on the screen of a TV monitor (not shown). The second set consists of an image-enlarging button 643a and an image-reducing button 643b. The surgeon may push these buttons 643a and 643b to drive the zoom lens built in the scope employed (not shown), thereby to enlarge and reduce the image displayed on the screen of the TV monitor.

The process of moving, enlarging or reducing the image does not interfere with the surgeon's manipulating of the medical instrument at all. Therefore, the remote-control panel 641 helps the surgeon to perform surgery with high efficiency.

An endoscope surgery system according to the twenty-eighth embodiment of the invention will be described, with reference to FIG. 52B. This embodiment is a fourth modification of the twenty-fourth embodiment. It is characterized in that a joy stick 651 is used, instead of the position-designating device 612.

The joy stick 651 is attached to the operation section of the medical instrument instrument used, the floor of the operating room, or a side of the operating bed. As shown in FIG. 52B, the joy stick 651 comprises an operation panel 652 and a rod 653 protruding upwards from the center part of the panel 652. Four position labels 654a to 654d are put on the panel 652, indicating upward, downward, leftward and rightward directions, respectively. The rod 653 can be inclined to the position labels 654a to 654d. It can also be pulled in the direction of arrow T and pushed in the direction of arrow W. The surgeon may incline the rod 653 to the labels 654a, 654b, 654c and 654d to move the image upwards, downwards, leftward and rightward on the screen of a TV monitor (not shown). Furthermore, the surgeon pull and push the rod 653 to drive the zoom lens built in the scope employed (not shown), thereby to enlarge and reduce the image displayed on the screen of the TV monitor.

The process of moving, enlarging or reducing the image does not interfere with the surgeon's manipulating of the medical instrument at all. The joy stick 651 assists the surgeon in enhancing the surgery efficiency.

An endoscope surgery system according to the twenty-ninth embodiment of the invention will be described, with reference to FIG. 53. The embodiment is a modification of the thirteenth embodiment illustrated in FIGS. 34A to 34C, 35A to 35C and 36. It has a TV camera 415 and an optical system having a single optical path.

The TV camera 415 is formed integral with or connected to a rigid scope (not shown), such as a laparoscope, for scanning an image picked up by the scope, either in part or in its entirety.

Figure 53:
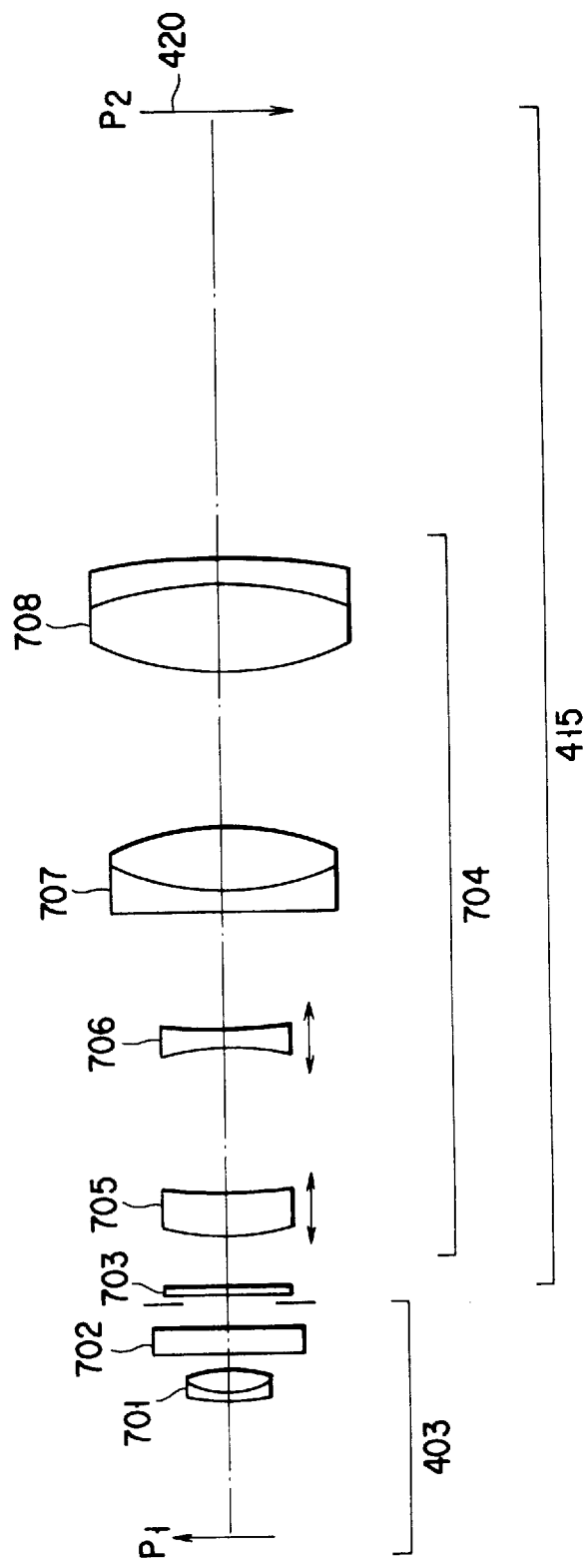
FIG. 53 shows the optical system incorporated in an endoscope surgery system according to a twenty-ninth embodiment of the present invention.

As shown in FIG. 53, the optical system comprises an ocular lens 701 and a glass cover 702, both provided in the ocular section 403 of the rigid scope. The optical system further comprises a glass cover 703 and a zoom lens unit 704, both incorporated in the TV camera 415 formed integral with or connected to the ocular section 403.

The zoom lens unit 704 comprises a compensator lens 705, a variator lens 706, and two lenses 707 and 708. The zoom lens unit 704 cooperates with the ocular lens 701 and the glass cover 702, both contained in the ocular section 403, to focusing an image $P_1$ provided by the objective lens (not shown) and relay lens (not shown) arranged in the barrel of the scope, thereby forming an optical image $P_2$ on the light-receiving surface of a CCD 420. The image $P_2$ can be magnified and reduced, by means of compensator lens 705 and the variator lens 706 of the zoom lens unit 704. Thus, the TV camera 415 can provide images of various sizes, ranging from a wide-angle image to a narrow-angle image.

The CCD 420 can be moved in a plane perpendicular to the optical axis of the rigid scope, by means of a CCD-driving mechanism (not shown). The distal end of the forceps inserted in the peritoneal cavity can therefore be tracked. The lens 708 is moved along the optical axis of the scope, achieving focusing of the image. The lens 708 may be moved by either a manual focusing mechanism having a dial or an automatic focusing mechanism having an actuator.

An endoscope surgery system according to the thirtieth embodiment of the invention will be described, with reference to FIG. 54. The thirtieth embodiment is a modification of the eighteenth embodiment illustrated in FIGS. 40A, 40B and 41. It has a TV camera 415 and an optical system having two optical paths, i.e., a first optical path 722a and a second optical path 722b.

The TV camera 415 is formed integral with or connected to a rigid scope (not shown), such as a laparoscope, for scanning an image picked up by the scope, either in part or in its entirety.

Figure 54:
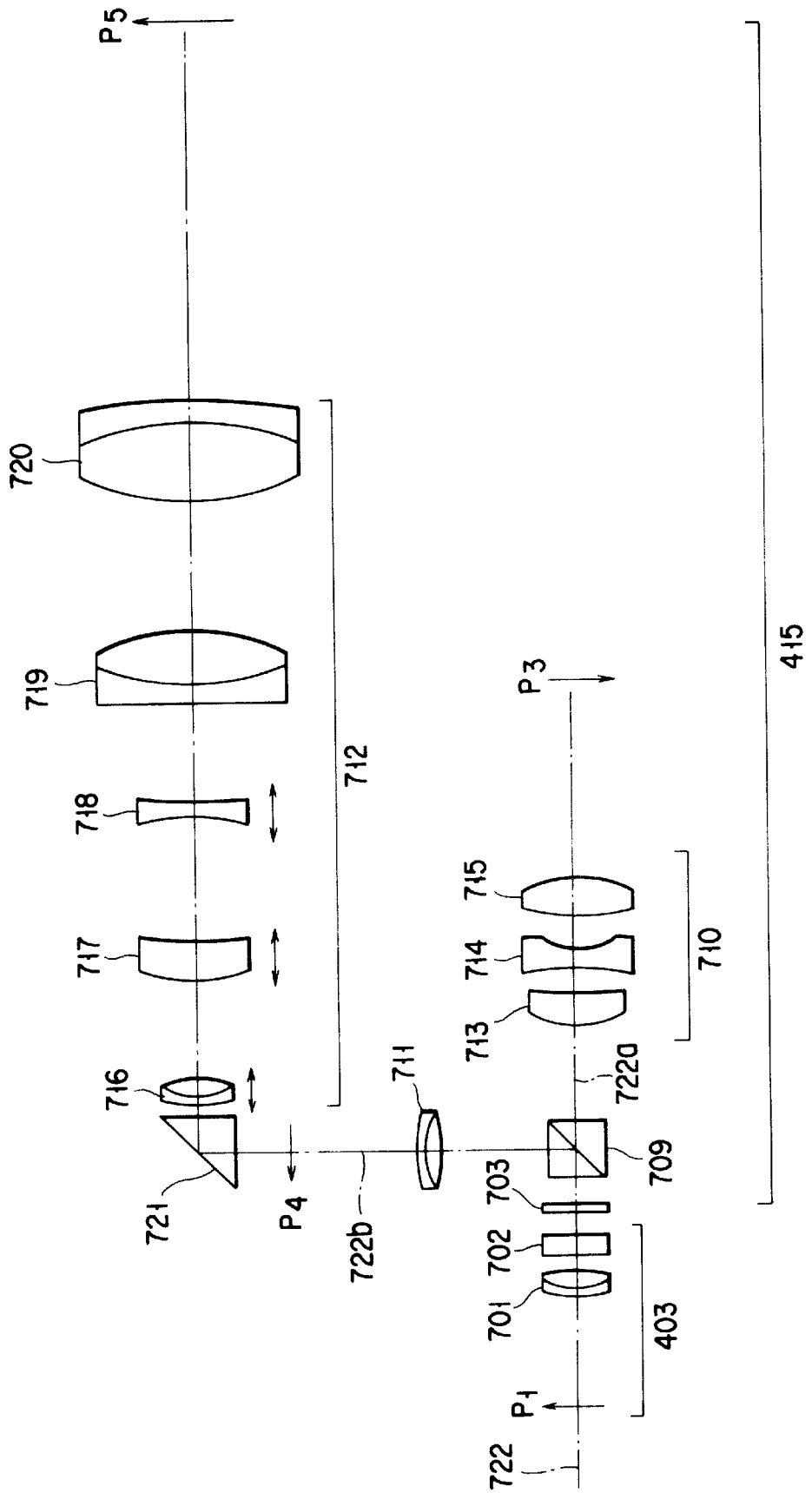
FIG. 54 shows the optical system incorporated in an endoscope surgery system according to a thirtieth embodiment of the invention.

As shown in FIG. 54, the optical system comprises an ocular lens 701 and a glass cover 702, both provided in the ocular section 403 of the rigid scope and arranged in the first optical path 722a. The optical system further comprises a glass cover 703, a beam splitter 709, a wide-angle optical unit 710, which are arranged in the first optical path 722a. The beam splitter 709 is located behind the cover glass 703, for splitting a light beam supplied from the glass cover 703 into two beams. These beams are distributed to the first optical path 722a and the second optical path 722b.

The wide-angle optical unit 710 is positioned in the first optical path 722a and behind the beam splitter 709. The unit 710 comprises three lenses 713, 714 and 715.

In the second optical path 722b there are arranged an intermediate image forming lens 711, a zoom lens unit 712, and a prism 721. The prism 721 is interposed between the lens 711 and the zoom lens unit 712. The zoom lens unit 712 comprises a focus-adjusting lens 716, a compensator lens 717, a variator lens 718, and two lenses 719 and 720.

The two beams split by the beam splitter 709 are supplied to the wide-angle optical unit 710 and the zoom lens unit 712. Namely, the image $P_1$ provided by the objective lens (not shown) and relay lens (not shown) which are arranged in the barrel of the scope is split into two part. The first part of the image $P_1$ is supplied to the first optical path 722a, and the second part of the image $P_1$ to the second optical path 722b.

The wide-angle optical unit 710 receives the first part of the image $P_1$ and converts it to a wide-angle image $P_3$. Meanwhile, the intermediate image forming lens 711 receives the second part of the image $P_1$ and converts it to an intermediate image $P_4$. The intermediate image $P_4$ is supplied to the zoom lens unit 712. The zoom lens unit 712 forms a narrow-angle image $P_5$ from the intermediate image $P_4$.

The wide-angle image $P_3$ is formed on the light-receiving surface of a first CCD 524 which is held in place. The narrow-angle image $P_5$ is formed on the light-receiving surface of a second CCD 420 which can be moved. By moving the second CCD 420 it is possible to switch the narrow-angle image $P_5$ and, hence, to track the distal end of forceps inserted in the peritoneal cavity.

Due to the use of the prism 721, the second optical path 722b extends substantially parallel to the first optical path 722a. Both CCDs 420 and 524 can therefore have their axes arranged in parallel to each other. The space the TV camera 415 occupies can be relatively small.

Since the second optical path 722b extends almost parallel to the first optical path 722a, it can be rendered as long as is desired. Nonetheless, the optical image is not deteriorated, because the lens 711 positioned between the beam splitter 709 and the prism 721 forms an intermediate image $P_4$, which is input to the zoom lens unit 712 via the prism 721.

In the optical system of the thirtieth embodiment, the beam forming the wide-angle image $P_3$ on the CCD 524 is substantially telecentric to the beam forming the narrow-angle image $P_5$ on the CCD 420. This prevents color shading from occurring in the CCD 420 or the CCD 524.

The ratio between the output beams of the beam splitter 709 can be set at the following value:

$$A:B=1:4 \tag{1}$$

where A is the amount of light applied to the first optical path 722a, and B is the amount of light applied to the second optical path 722b.

Since the amount B is four times the amount A, the narrow-angle image $P_5$ can be bright enough to be observed well.

The narrow-angle image $P_5$ is not inverted with respect to the image $P_1$ provided by the objective lens and the relay lens. This is because the image $P_1$ is turned by 90° at the beam splitter 709 and turned by 90° again at the prism 721. In addition, the focusing can be conducted, merely by moving the focus-adjusting lens 716 back and forth along the optical axis of the zoom lens unit 712. The lens 716 may be moved so, by means of either a manual focusing mechanism having a dial or an automatic focusing mechanism having an actuator.

An endoscope surgery system according to the thirty-first embodiment of the invention will be described, with reference to FIG. 55. This endoscope surgery system is a modification of the thirtieth embodiment shown in FIG. 54. It differs from the thirtieth embodiment only in that a narrow-angle optical unit 723 is used in place of the zoom lens unit 712.

As seen from FIG. 55, the narrow-angle optical unit 723 comprises four lenses 724, 725, 726 and 727. The unit 723 has magnification $\beta_T$, which is greater than the magnification $\beta_W$ of the wide-angle optical unit 710. That is, $\beta_T > \beta_W$.

As can be understood from FIG. 55, the beam splitter 709 receives an optical image $P_1$ provided by the objective lens (not shown) and relay lens (not shown) which are arranged in the barrel of a scope. The beam splitter 709 splits the image $P_1$ into two part, which are supplied to two optical paths 722a and 722b. The second part of the image $P_1$ supplied to the second optical path 722b is input to an intermediate image forming lens 711. The intermediate image forming lens 711 converts the second part of the image $P_1$ to an intermediate image $P_4$, which is supplied to the narrow-angle optical unit 723. The unit 723 forms a narrow-angle image $P_7$ from the intermediate image $P_4$.

The wide-angle image $P_3$ is formed on the light-receiving surface of a first CCD 524 which is held in place. The narrow-angle image $P_6$ is formed on the light-receiving surface of a second CCD 420 which can be moved. By moving the second CCD 420 it is possible to switch the narrow-angle image $P_6$ and, hence, to track the distal end of forceps inserted in the peritoneal cavity.

Due to the use of a prism 721 provided between the intermediate image forming lens 711 and the lens 724 of the zoom lens unit 723, the second optical path 722b extends substantially parallel to the first optical path 722a. Both CCDs 420 and 524 can therefore have their axes arranged in parallel to each other. The TV camera 415 can be made relatively compact.

The narrow-angle image $P_6$ is not inverted with respect to the image $P_1$ provided by the objective lens and the relay lens. This is because the image $P_1$ is turned by 90° at the beam splitter 709 and turned by 90° again at the prism 721. In addition, the focusing can be conducted, merely by moving the lens 724 back and forth along the optical axis of the zoom lens unit 723. The lens 724 may be moved so, by means of either a manual focusing mechanism having a dial or an automatic focusing mechanism having an actuator.

Another endoscope surgery system, which is the thirty-second embodiment of the invention will be described with reference to FIG. 56. This embodiment is a modification of the nineteenth embodiment shown in FIGS. 42A, 42B and 42C. It differs from the nineteenth embodiment only in the optical system of the TV camera 415.

Figure 56:
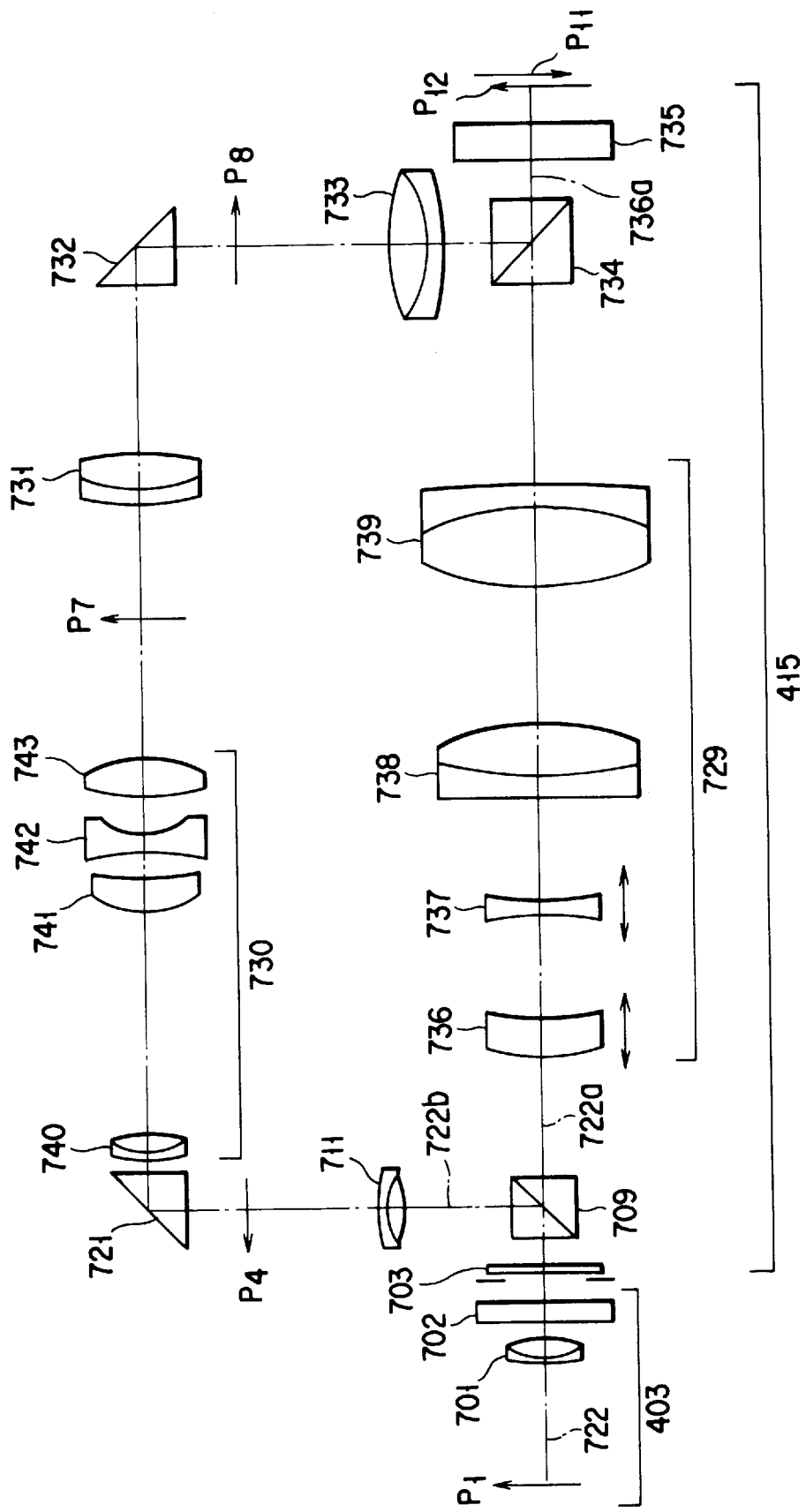
FIG. 56 shows the optical system incorporated in an endoscope surgery system according to a thirty-second embodiment of the present invention.

As illustrated in FIG. 56, the optical system comprises an ocular lens 701 and a glass cover 702, both provided in the ocular section 403 of the rigid scope and arranged in a first optical path 722a. The optical system further comprises a glass cover 703 and beam splitter 709. The The beam splitter 709 is located behind the cover glass 703, for splitting a light beam supplied from the glass cover 703 into two beams. These beams are distributed to the first optical path 722a and the second optical path 722b.

In the first optical path 722a there are arranged a zoom lens unit 729, a polarized beam splitter 734 and a liquid-crystal shutter 735, in the order they are mentioned. The zoom lens unit 728 is of the same type as used in the twenty-ninth embodiment (FIG. 53) and comprises a compensator lens 736, a variator lens 737, and two lenses 738 and 740.

In the second optical path 722b there are arranged a first intermediate image forming lens 711, a prism 721, a wide-angle optical unit 730, a second intermediate image forming lens 731, a prism 732, and a focusing lens 733 are arranged. The wide-angle optical unit 730 comprises four lenses 740, 741, 742 and 743. The prism 721 is located between the first intermediate image forming lens 711 and the wide-angle optical unit 730. The prism 732 is provided between the second intermediate image forming lens 731 and the focusing lens 733. The focusing lens 733 is positioned between the prism 732 and the polarized beam splitter 734.

The polarized beam splitter 734 is designed to polarize light beams input from the zoom lens unit 729 and the focusing lens 733.

The beam splitter 709 receives an optical image $P_1$ provided by the objective lens (not shown) and relay lens (not shown) which are arranged in the barrel of a scope. The beam splitter 709 splits the image $P_1$ into two part, which are supplied to two optical paths 722a and 722b. The first part of the image $P_1$ supplied via the zoom lens unit 729 to the polarized beam splitter 734. The beam splitter 734 polarizes the first part of the image $P_1$, which is supplied to the liquid-crystal shutter 735. The shutter 735 forms a narrow-angle image $P_{11}$.

Meanwhile, the second part of the image $P_1$ is supplied from the beam splitter 709 to the first intermediate image forming lens 711, which forms an intermediate image $P_4$. The intermediate image $P_4$ is supplied via the prism 721 to the wide-angle optical unit 730. The unit 730 forms a second intermediate image $P_7$, which is supplied to the prism 732 through the second intermediate image forming lens 731. The prism 732 forms a third intermediate image $P_8$. The image $P_8$ is supplied via the focusing lens to the polarized beam splitter 734. The beam splitter 734 polarizes the third intermediate image $P_8$, which is supplied to the liquid-crystal shutter 735. The shutter 745 forms a wide-angle image $P_{12}$.

The polarized state of the liquid-crystal shutter 735 is switched, thereby to select the narrow-angle image $P_{11}$ or the wide-angle image $P_{12}$. The wide-angle image $P_{12}$ can be displayed, and the distal end of forceps (not shown) can be tracked.

Focusing can be conducted, merely by moving the lens 740 back and forth along the optical axis of the wide-angle optical unit 730. The lens 740 may be moved so, by means of either a manual focusing mechanism having a dial or an automatic focusing mechanism having an actuator. Furthermore, the beam splitter 709 may be replaced by a rotatable mirror.

An endoscope surgery system according to the thirty-third embodiment of the invention will be described, with reference to FIGS. 57, 58, 59, 60A to 60C, and 61. The endoscope surgery system has a rigid scope 801 of direct-view type, such as a laparoscope.

Figure 58:
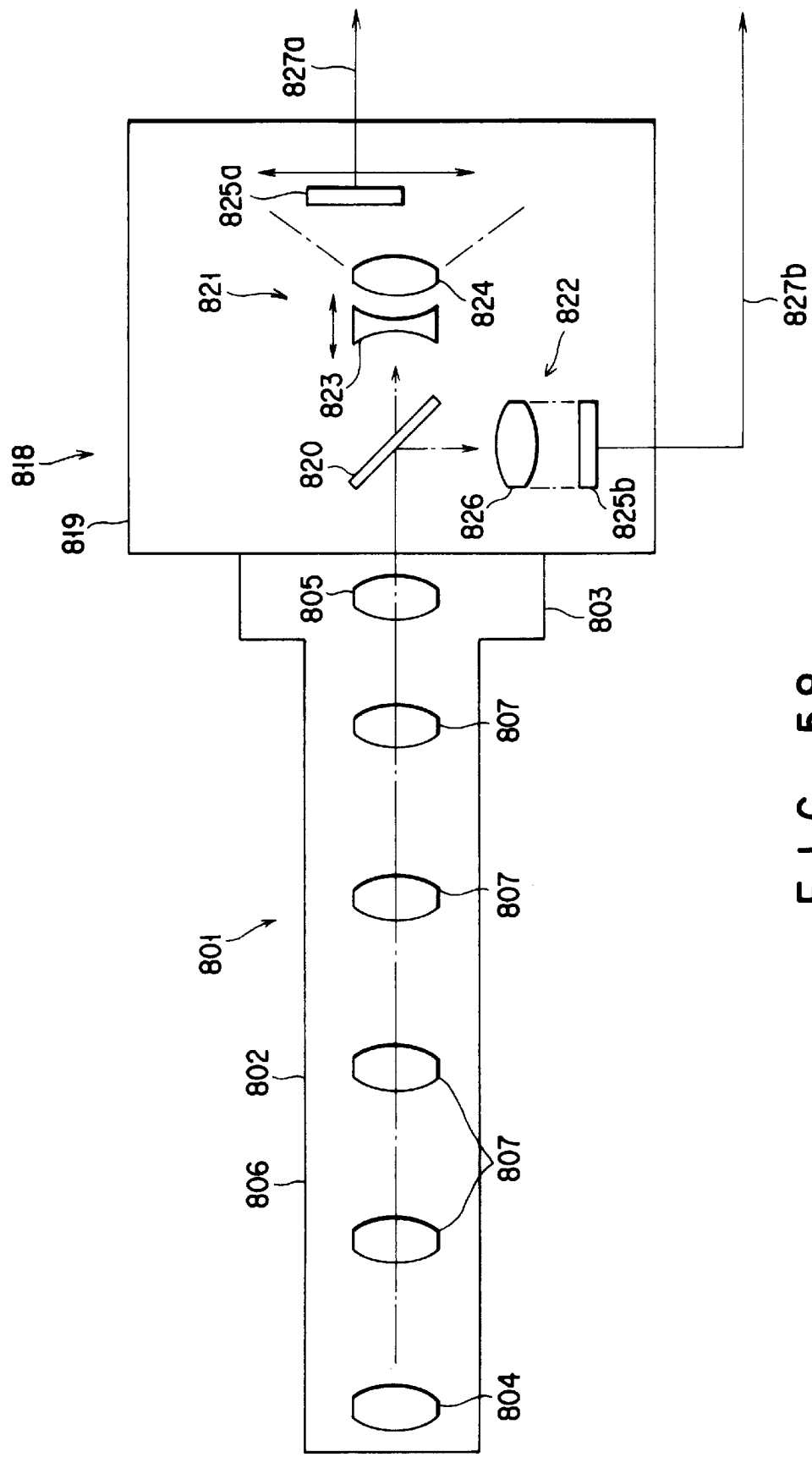
FIG. 58 is a diagram showing the rigid scope and the TV camera, both incorporated in the thirty-third embodiment.

As shown in FIG. 57, the rigid scope 801 comprises an insertion section 802 and an ocular section 803. As shown in FIG. 58, the insertion section 802 contains an objective lens 804 in its distal end, and the ocular section 803 contains an ocular lens 805. The barrel 806 of the insertion section 802 contains a plurality of relay lenses 807. The relay lenses 807 are located between the objective lens 804 and they ocular lens 805. They are spaced apart from one another. The optical system of the rigid scope 801 further includes a distortion-compensating lens (not shown).

As seen from FIG. 57, a trocar 809 is set in an opening incised in the abdominal wall 808 of a patient. The insertion section 802 of the rigid scope 801 is inserted through the trocar 809 into the peritoneal cavity of the patient. The proximal portion of the insertion section 802 is movably held by a scope holder 810 which is a multi-joint structure.

The insertion section 802 of the rigid scope 802 incorporates a light guide fiber (not shown) for applying illumination light to the distal end of the insertion section 802. Connected to the light guide is one end of alight guide cable 811. The other end of the cable 811 is connected to a light source 812 located outside the rigid scope 801.

As shown in FIG. 57, another trocar 809' is set in an opening incised in the abdominal wall 808, spaced apart from the first trocar 809. A pair of forceps 813, which is a medical instrument, is inserted through the second trocar 809' into the patient's peritoneal cavity. The forceps 813 comprises an insertion section 814, a pair of tongs 815, and a handle 816. Tongs 815 are connected to the distal end of the insertion section 814. The handle 816 is connected to the proximal end of the insertion section 814. When the handle 816 is opened and closed, the tongs 815 are opened and closed by remote control.

A color marker 817 is adhered to one of the tongs 815, enabling the surgeon to recognize the position of the tongs 815 easily. The color marker 817 is biologically adapted paint. The marker 817 is of a color quite different from those of the organs, such as green, yellow or the like. The forces 813 may be replaced by any other medical instrument such as ablation forceps, scissors, a laser probe, a suturing device, an electric knife, a stylus holder, and an ultrasonic suction device.

The TV camera unit 818 is removably attached to the ocular section 803 of the rigid scope 801. The TV camera unit 818 is designed to generate image signals from the light supplied from the light supplied from the rigid scope 801. As shown in FIG. 58, the unit 818 comprises a casing 819, a half mirror 820, a magnifying optical system 821, and a wide-angle optical system 822. The mirror 820 and both optical systems 821 and 822 are contained in the casing 819. The half mirror 820 opposes the ocular lens 805 provided in the ocular section 803 of the rigid scope 801 and is spaced apart from the ocular lens 805. The half mirror 820 splits an optical image supplied from the ocular section 803 into two images. The first image passes through the half mirror 820 and is supplied to the magnifying optical system 821, while the second image is reflected by the half mirror 820 is supplied to the wide-angle optical system 822.

The half mirror 820 can be replaced by an optical reflector such as a prism.

As illustrated in FIG. 58, the magnifying optical system 821 comprises a zoom lens 823, a focusing lens 824, and a single-plate CCD (first CCD) 825a having a mosaic filter. The wide-angle optical system 822 comprises a focusing lens 826 and a single-plate CCD (second CCD) 825b having a mosaic filter. The CCD 825a of the magnifying optical system 821 is mounted on an X-Y stage (not shown) which can move in a horizontal plane, along X axis and Y which intersect with each other at right angles. The X-Y stage is driven by an actuator (not shown, either) such as a DC servo motor, a stepping motor, a voice-coil motor, or the like. The zoom lens 823 of the magnifying optical system 821 is driven by an actuator (not shown), which may be a DC servo motor, a stepping motor, a voice-coil motor, or the like.

As shown in FIG. 57, the TV camera unit 818 is connected by video-signal cables 827a and 827b to two CCUs (Camera Control Units) 828a and 825b. The unit 818 is also connected by a control-signal cable 829 to a view-field switching unit 830. The CCU 825a incorporated in the magnifying optical system 821 is connected to the first CCU 828a by the video-signal cable 827a. The CCD 825b provided in the wide-angle optical system 822 is connected by the video-signal cable 827b to the second CCU 828b. The actuator for driving the X-Y stage and the actuator for driving the zoom lens, both incorporated in the TV camera unit 818, are connected to the view-field switching unit 830 by the control-signal cable 829.

The CCUs 828a and 828b are connected to a video mixer 831 provided outside the rigid scope 801. The vide mixer 831 is connected to a TV monitor 832. The second CCU 828b is also connected to the view-field switching unit 830. Connected to the unit 830 are two foot switches 833a and 833b. While the first foot switch 833a remains depressed, the endoscope surgery system operates in suturing/tying mode. While the second foot switch 833b remains depressed, the system operates in view field switching mode. A zooming switch (not shown) is connected to the second foot switch 833b.

Figure 59:
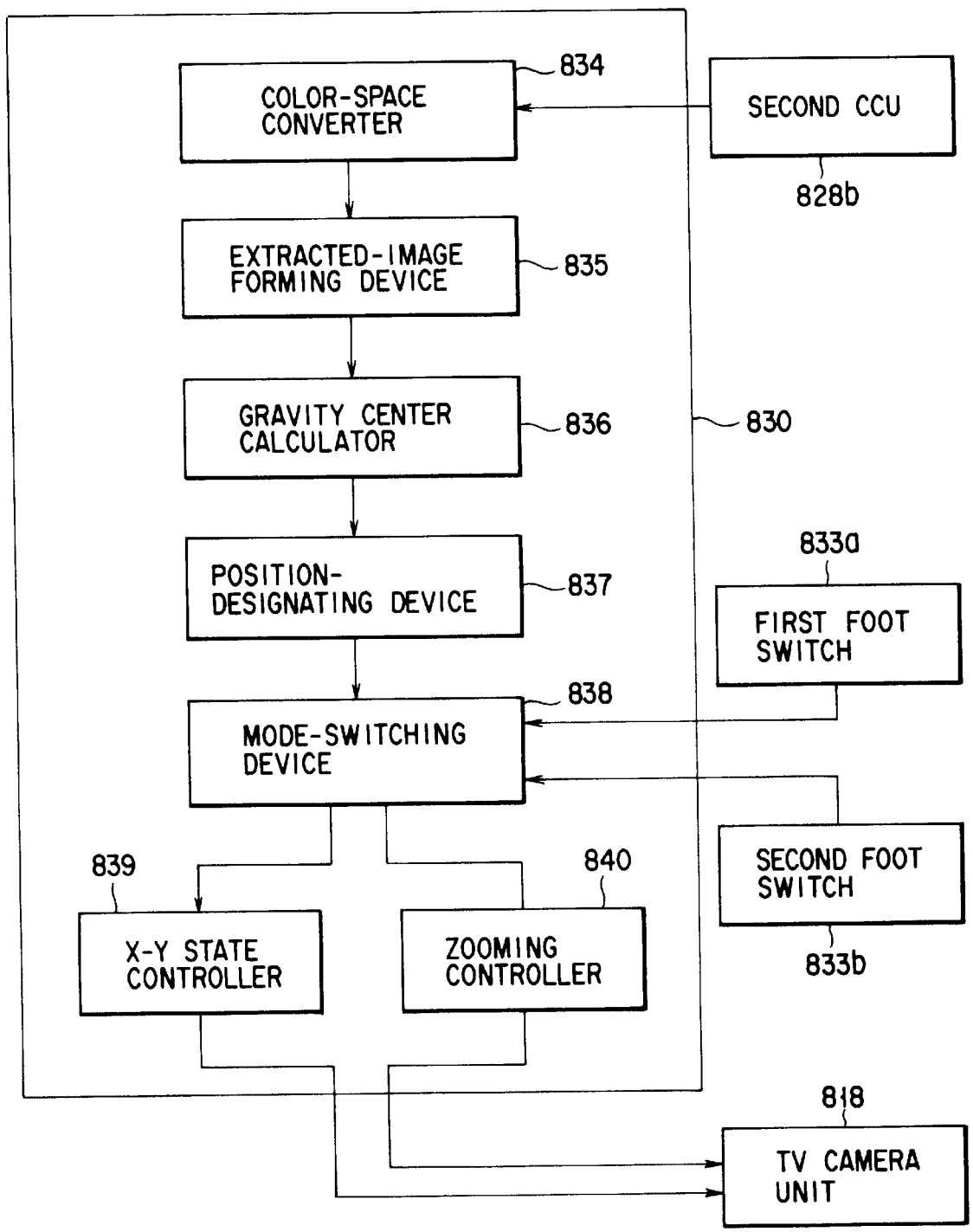
FIG. 59 is a block diagram of the view field control unit incorporated in the thirty-third embodiment.

FIG. 59 is a block diagram of the view-field switching unit 830. As can be understood from FIG. 59, the unit 830 comprises a color-space converter 834, an extracted-image forming device 835, a gravity center calculator 836, a position-designating device 837, a mode-switching device 838, an X-Y stage controller 839, and a zooming controller 840. The color-space converter 834 is connected to the second CCU 828b to received a signal supplied therefrom. The extracted-image forming device 835 is connected to the converter 834 to receive a signal supplied therefrom. The gravity center calculator 836 is connected to the device 835 for receiving a signal supplied therefrom. The position-designating device 837 is connected to the mode-switching device 838. The device 838 is connected to the X-Y stage controller 839, and a zooming controller 840. Connected to the device 838 are the first foot switch 833a and the second foot switch 833b.

The actuator for driving the X-Y stage provided in the TV camera unit 818 is connected to the X-Y stage controller 839. A control signal generated by the controller 839 is input to the actuator for driving the X-Y stage. The actuator for driving the zoom lens provided in the TV camera unit 818 is connected to the zooming controller 840.

The operation of the thirty-third embodiment will now be explained.

At first, the surgeon inserts the insertion section 802 of the rigid scope 801 held by the scope holder 810 is inserted into the patient's peritoneal cavity through the first trocar 809 set in the opening incised in the abdominal wall 808, as illustrated in FIG. 57. Next, the surgeon inserts the forceps 814 into the peritoneal cavity through the second trocar 809' set in the opening incised in the abdominal wall 808. As shown in FIG. 57, the forceps 813 is positioned such that its tongs 815 is located within the view field $R_1$ of the wide-angle optical system 821.

An optical image of the objects in the view field $R_1$ is supplied through the rigid scope 801 to the TV camera unit 818 connected to the ocular section 803 of the unit 818. In the TV camera unit 818, the half mirror 820 spits the optical image into two. The first image passing through the half mirror 820 is supplied to the magnifying optical system 821, and the second image reflected by the half mirror 820 is supplied to the wide-angle optical system 822. In the magnifying optical system 821, the firs image is supplied to the first CCD 825a. In the wide-angle optical system 822, the second image is supplied to the second CCD 825b.

To suture a tissue present in the peritoneal cavity, the surgeon operates the first foot switch 833a, which generates an ON signal. As a result, the endoscope surgery system is set into the suturing/tying mode. The ON signal is supplied to the mode-switching device 838 of the view-field switching unit 830. Upon receipt of the ON signal, the mode-switching device 838 supplies a suturing/tying signal to the zooming controller 840.

In response to the suturing/tying signal, the zooming controller 840 drives the actuator of the magnifying optical system 821, whereby the zoom lens 823 is repeatedly moved back and forth along the optical axis of the system 821. As a result of this, a wide-angle image of the tongs 815 and a magnified image thereof are alternately displayed by the TV monitor 832, as is illustrated in FIGS. 60A and 60B. Seeing both images displayed alternately, the surgeon can apply a suture to the tissue and to tie a blood vessel or a nervous tissue.

The view-field switching unit 830 may be designed so as to determine whether a suture is being applied to the tissue or the needle is being replaced with another. When the surgeon finishes applying the suture to the tissue, the magnifying optical system 821 operates to display a magnified image on the TV monitor 832. When the surgeon finishes exchanging the needle with another, the system 821 operates to display a wide-angle image on the TV monitor 832.

To switch the view field of the TV camera unit 818, the surgeon operates the second foot switch 833b, which generates an ON signal. As a result, the endoscope surgery system is set into the view field switching mode. The ON signal is supplied to the mode-switching device 838 of the view-field switching unit 830. Upon receipt of the ON signal, the mode-switching device 838 supplies a view field switching signal to the X-Y stage controller 839. The controller 839 controls the XY stage in accordance with the view field switching signal, whereby the first CCD 825a is moved in a plane perpendicular to the optical axis of the magnifying optical system 821. As a result, the view filed of the TV camera unit 818 is switched.

How the view field of the TV camera unit 818 is switched will be explained in detail.

A video signal generated by the second CCD 825a of the wide-angle optical system 822 is input to the color-space converter 834 provided in the view-field switching unit 830. The converter 834 converts the color component for each pixel to a color-difference signals (Y, B-Y, R-Y) and a color space such as an HSI (Hue, Saturation, Intensity) space.

The color-difference signals and the color space are input to the extracted-image forming device 835. The device 835 determines whether or not each input color-space signal represents a pixel color which falls within a preset color range. If the color-space signal represents a pixel color falling with the color range, the device 835 imparts intensity 0 to the color-space signal. Otherwise, the device 835 imparts intensity 1 to the color-space signal. Therefore, the device 835 outputs binary image data which consists of "0" bits representing black pixels and "1" bits representing white pixels.

The binary image data output from the extracted-image forming device 835 is supplied to the gravity center calculator 836. The gravity center calculator 836 calculates the center of the black portion of the image represented by the binary image data. The calculator 836 generates pixel data representing the coordinates of the black pixel located at the center of the black portion of that image. The pixel data is input to the position-designating device 837.

The position-designating device 837 obtains the difference between the coordinates of the black pixel and the coordinates of a point at which this black pixel should be displayed on the TV monitor 832, for example the very center of the TV monitor screen. The difference, thus obtained, is supplied as an image-moving signal to the mode-switching device 838. When the surgeon operates the second foot switch 833b in this condition, the device 838 supplies the image-moving signal to the XY stage controller 839. Upon receipt of the image-moving signal, the controller 839 generates and supplies a control signal to the actuator for driving the X-Y stage provided in the TV camera unit 818.

The actuator drives the X-Y stage, whereby the first CCD 825a of the magnifying optical system 821 is moved along the X and the Y axes, for the distances represented by the image-moving signal which the position-designating device 837 has generated. As a result, the black pixel located at the center of the black portion of that image is displayed at the center of the screen of the TV monitor 832.

The optical image supplied to the magnifying optical system 821 from the half mirror 820 passes through the zooming lens 823. The lens 823 magnifies the image, a part of which is focused on the first CCD 825a by the focusing lens 824. The zooming lens 823 magnifies the intra-cavity image. The image magnified is supplied to the ocular lens 805. Hence, only a part of the magnified image is formed on the first CCD 825*a*, and the surgeon can see an enlarged image of the objects represent in the peritoneal cavity.

The color of the color marker 817 adhered to one of the tongs 815 of the forceps 813 may be designated as one to be extracted, and the center of the screen of the TV monitor 832 may be set in the view-field switching unit 830 as the position where the tongs 815 should be displayed. If the tissue to be treated may be displayed in an edge part of the view field of the magnifying optical system 821, though the color marker 817 is within the view field of the wide-angle optical system 822 of the rigid scope 801. In this case, it is difficult for the surgeon to treat the tissue, while observing the image of the tissue and the image of the tongs 815, both displayed on the TV monitor screen. To have the tissue displayed at the center of the view field, the surgeon moves the forceps 813 to the tissue and clamps the tissue with the tongs 815, and then turns on the second foot switch 833*b*. Then, the first CCD 825*a* is moved such that the distal end of the forceps 813 is caught at the center of the view field of the magnifying optical system 821. Thus, the distal end of the forceps 813 is tracked.

When the zooming switch (not shown) provided on the second switch 833*b* is pushed, the mode-switching device 838 supplies a zooming signal to the zooming controller 840. The zooming controller 840 generates a signal representing the distance for which the zoom lens 823 should be moved. This signal is supplied to the actuator for driving the zoom lens 823. The actuator moves the zoom lens 823 for that distance, along a line perpendicular to the first CCD 825*a*.

The video mixer 831 receives the signals output from the first CCU 828*a* and the second CCU 828*b*. From these signals the video mixer 831 generates two image data items which respectively represent the magnified image formed by the first CCD 825*a* and the wide-angle image formed by the second CCD 825*b*. These image data items are supplied to the TV monitor 832. The TV monitor 832 displays the magnified image and the wide-angle image simultaneously. Alternatively, it displays either the magnified image or the wide-angle image. It should be noted that the magnified image is of the objects of interest, whereas the wide-angle image is of the objects of interest and other objects located near the objects of interest.

The position where the tongs 815 should be displayed on the screen of the TV monitor 832 can be altered. The first foot switch 833*a* and the second foot switch 833*b* for setting the system the suturing/tying mode and the view field switching mode, respectively, may be replaced by hand switches which may be provided on the handle 816 of the forceps 813. Moreover, the focusing lens 824 may be fastened to the XY stage so that it may serve to switch the view field.

As described above, the thirty-third embodiment can be operated in two modes. In the suturing/tying mode, a magnified image and a wide-angle image can be alternately displayed on the screen of the TV monitor 832. In the view field switching mode, the view field can be switched in accordance with the position of the distal end of the forceps 813. Hence, the various view fields can be provided without using two or more devices, enabling the surgeon to perform the surgery with high efficiency.

As mentioned above, the half mirror 820 provided in the casing 819 of the TV camera unit 818 distributes the optical image supplied from the ocular section 803 of the scope 801, to two optical paths. The half mirror 820 can be replaced by an optical reflector such as a prism.

As shown in FIG. 61, pigments 841*a*, 841*b* and 841*c* of different colors may be applied to the tissues which exist in the peritoneal cavity and which the surgeon needs to treat. In this case, the first CCD 825*a* can be moved to switch the view field so that those parts of the tissues which are colored with pigments 841*a*, 841*b* and 841*c* may be displayed, one at a time at the center part to the screen of the TV monitor 832. Thus, the images of the tissues can be moved to the center of the TV monitor screen.

Alternatively, clips of different colors may be secured to the tissues to be treated. Further, the shape of the distal end of the forceps 813 may be detected, and pattern matching is carried out to determine where the distal end of the forceps 813 is located in the peritoneal cavity.

An endoscope surgery system according to the thirty-fourth embodiment of the invention will be described, with reference to FIG. 62. The thirty-fourth embodiment is a modification of the thirty-third embodiment. It differs in the structure of the view-field switching unit 830.

The view field switching unit 830 has two additional components, i.e., a motion detector 851 and a zoom in/out controller 852. The motion detector 851 is provided for detecting the motion of the distal end of forceps. In the unit 830, the color-space converter 834, the extracted-image forming device 835, the gravity center calculator 836, and the position-designating device 837 constitute a view field switching control block, and the motion detector 851 and the zoom in/out controller 852 constitute a suturing/tying control block 854. In all other aspects the view-field switching unit 830 is identical to its counterpart of the thirty-third embodiment. The components similar or identical to those of the thirty-third embodiment will not be described in detail.

In operation, the video signal generated by the second CCD 825*b* incorporated in the wide-angle optical system 822 is supplied to the motion detector 851. The motion detector 851 detects the motion of the forceps 813. The motion detector 851 processes the input video signal to determine whether the forceps 813 is manipulated to apply a suture to a tissue or to exchange the needle with another. The detector 851 generates a signal indicating the application of suture or the passing of suture and supplies the signal to the zoom in/out controller 852. If the signal indicates the application of suture, the controller 852 generates a control signal for zooming in the zoom lens 823. If the signal indicates the application of suture, the controller 852 generates a control signal for zooming out the zoom lens 823. More precisely, the zoom in/out controller 852 generates a zoom-in control signal when the motion detector 851 detects that the tongs 815 has been rotated to apply the suture to the tissue, and generates a zoom-out control signal when the motion detector 851 detects that the tongs 815 has been opened and closed to exchange the needle with another.

An endoscope surgery system according to the thirty-fifth embodiment of the invention will be described, with reference to FIGS. 63A to 63D.

Figure 63A:
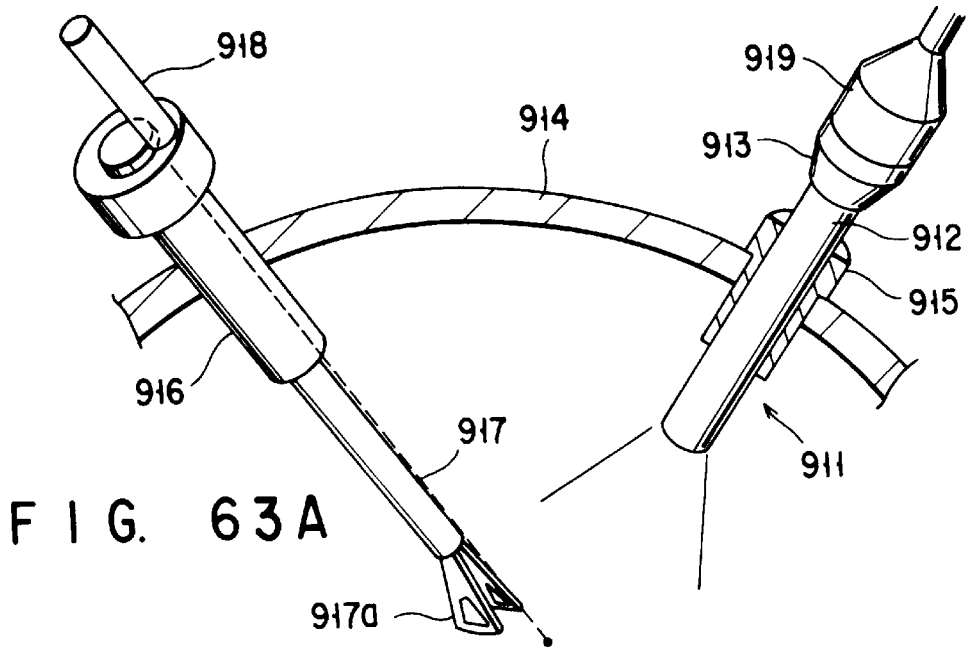
FIG. 63A is a diagram illustrating the scope and the medical instrument, both used in an endoscope surgery system according to a thirty-fifth embodiment of this invention.

As shown in FIG. 63A, this system comprises a rigid scope 911 of direct-view type, such as a laparoscope. The rigid scope 911 comprises an insertion section 912 and an ocular section 913 connected to the proximal end of the insertion section 912. The insertion section 912 is inserted in the peritoneal cavity of a patient through a trocar 915 which is set in an opening incised in the abdominal wall 914.

A second trocar 916 is set in an opening incised in the abdominal wall 914. Through the second trocar 916 a medical instrument 917 is inserted in the peritoneal cavity, for treating a tissue or holding an organ in the peritoneal cavity.

A laser pointer 918 is attached to the second trocar 916. The laser pointer 918 contains a semiconductor laser, which emits a laser beam. The laser pointer 918 is positioned such that the laser beam extends substantially parallel to the axis of the second trocar 916. The laser pointer 918 may be attached to the medical instrument 917, not to the second trocar 916.

Figure 63B:
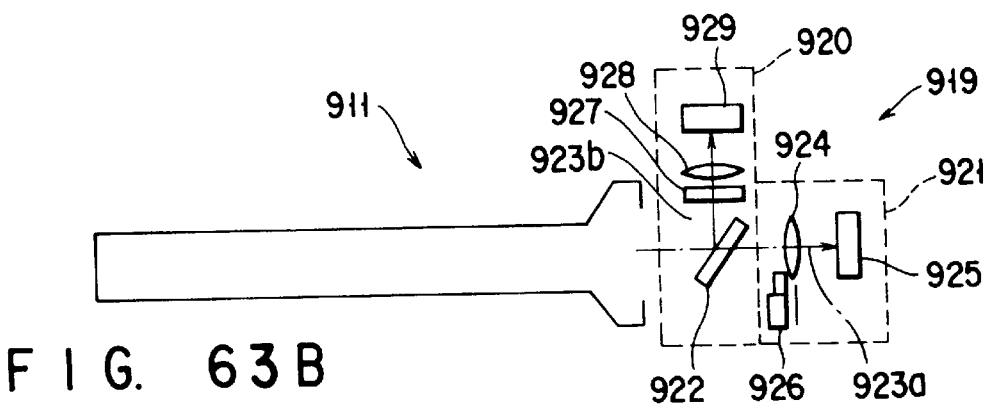
FIG. 63B is a diagram showing the rigid scope and the TV camera, both incorporated in the thirty-fifth embodiment.

A TV camera unit 919 is connected to the ocular section 913 of the rigid scope 911. As shown in FIG. 63B, the TV camera unit 919 comprises an adapter 920 and a TV camera 921. The adapter 920 contains a half mirror 922, which opposes the ocular section 913 and is spaced apart therefrom. The half mirror 922 receives an optical image from the ocular section 913 and distributes it to two optical paths 923a and 923b present in the TV camera unit 919. The half mirror 922 can be replaced by a beam splitter.

The TV camera unit 919 contains an optical element 924 and a first image pickup device 925, both arranged in the first optical path 923a. The optical image distributed to the first optical path 923a is supplied via the optical element 924 and focused onto the first image pickup device 925. The first pickup device 925 generates a video signal representing an endoscopic image. The TV camera unit 919 contains an actuator 926, too. The actuator 929 is provided to move the optical element 924 in a direction at right angles to the first optical path 923a.

The adapter 920 contains a filter 927, an optical element 928 and a second image pickup device 929, besides the half mirror 922. The filter 927 receives the optical image distributed by the half mirror 922 to the second optical path 923b, and allows the passage of only the laser beam. The laser beam is applied through the optical element 928 to the second image pickup device 929. The second image pickup device 929, which is either a CCD or a PSD, generates a video signal representing an image of the laser beam.

Figures 63C, 63D:
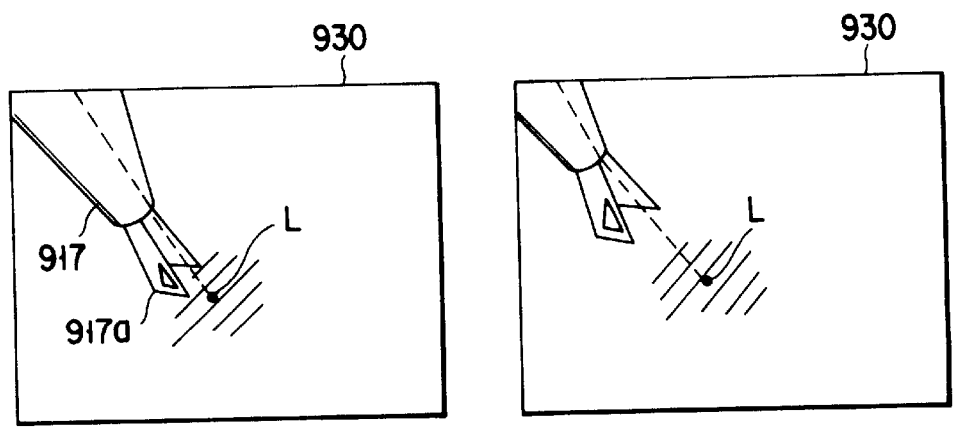
FIG. 63C shows an image provided by the rigid scope used in the thirty-fifth embodiment, illustrating a tissue located near the medical instrument.
FIG. 63D shows an image provided by the rigid scope used in the thirty-fifth embodiment, illustrating a tissue located far from the medical instrument.

The video signal generated by the first image pickup device 925 and the video signal generated by the second image pickup device 929 are supplied to a TV monitor 930. As a result, the TV monitor 930 displays an image of the distal end of the medical instrument 917, together with an image of the laser-beam spot L, as is illustrated in FIGS. 63C and 63D.

It will be explained how a surgeon perform endoscope surgery by using the system according to the thirty-fifth embodiment.

First, the surgeon inserts the insertion section 912 of the rigid scope 911 into the peritoneal cavity through the first trocar 915. Further, he or she inserts the medical instrument 917 into the cavity through the second trocar 916. The surgeon moves the insertion section 912 such that the tongs 917a attached to the distal end of the instrument 917 is caught in the view field of the ocular section 913 of the rigid scope 911.

In the TV camera unit 919, the half mirror 922 divides the optical image of the interior of the cavity into two parts. The first part of the image is distributed to the first optical path 923a and supplied through the optical element 924 to the first image pickup device 925. The first pickup device 925 generates a video signal representing an endoscopic image. Meanwhile, the second part of the image is distributed to the second optical path 923b and supplied to the filter 927. The filter 927 allows the passage of only the laser beam. The laser beam is applied through the optical element 928 to the second image pickup device 929. The device 929 generates a video signal representing an image of the laser beam.

The video signals generated by the first and second image pickup devices 925 and 929 are supplied to the TV monitor 930. The TV monitor 930 displays an image of the distal end of the medical instrument 917, together with an image of the laser-beam spot L, as is illustrated in FIGS. 63C and 63D. FIG. 63C shows the image of the laser-beam spot L located close to the image of the tongs 471a, while FIG. 63D shows the image of the laser-beam spot L located far from the image of the tongs 471a.

While the interior of the cavity is being observed, the center of the image displayed by the TV monitor 930 is calculated from the video signal which has been generated by the second image pickup device 929 and which represents the laser-beam spot L. The actuator 926 is driven in accordance with the position the center of the image displayed by the TV monitor 930. The actuator 926 moves the optical element 924 such that the center of the image moves to the center of the TV monitor screen.

The medical instrument 917 and the second trocar 916 are coaxial with each other. The laser beam emitted from the semiconductor laser pointer 918 attached to the trocar 916 is therefore applied to an organ to which the surgeon has moved the instrument 917. The laser beam form a spot L on the organ which the surgeon is going to treat. The actuator 926 is moves the optical element 924 such that the image of the organ is displayed in the center part of the screen of the TV monitor 930. Hence, the surgeon can easily switch the view field of the rigid scope 911 by moving the medical instrument to the organ he or she will treat.

An endoscope surgery system according to the thirty-sixth embodiment of the present invention will be described, with reference to FIGS. 66 to 69.

As may be understood from FIG. 66, the thirty-sixth embodiment is a modification of the another embodiment. It is characterized in two respects. First, no components equivalent to the magnetic sensor unit 873, the magnetic sensor 874 and the magnetism source 875 are used. Second, a view field controller 931 is connected to a CCU 880, which in turn is connected to a TV monitor 832.

Figure 64:
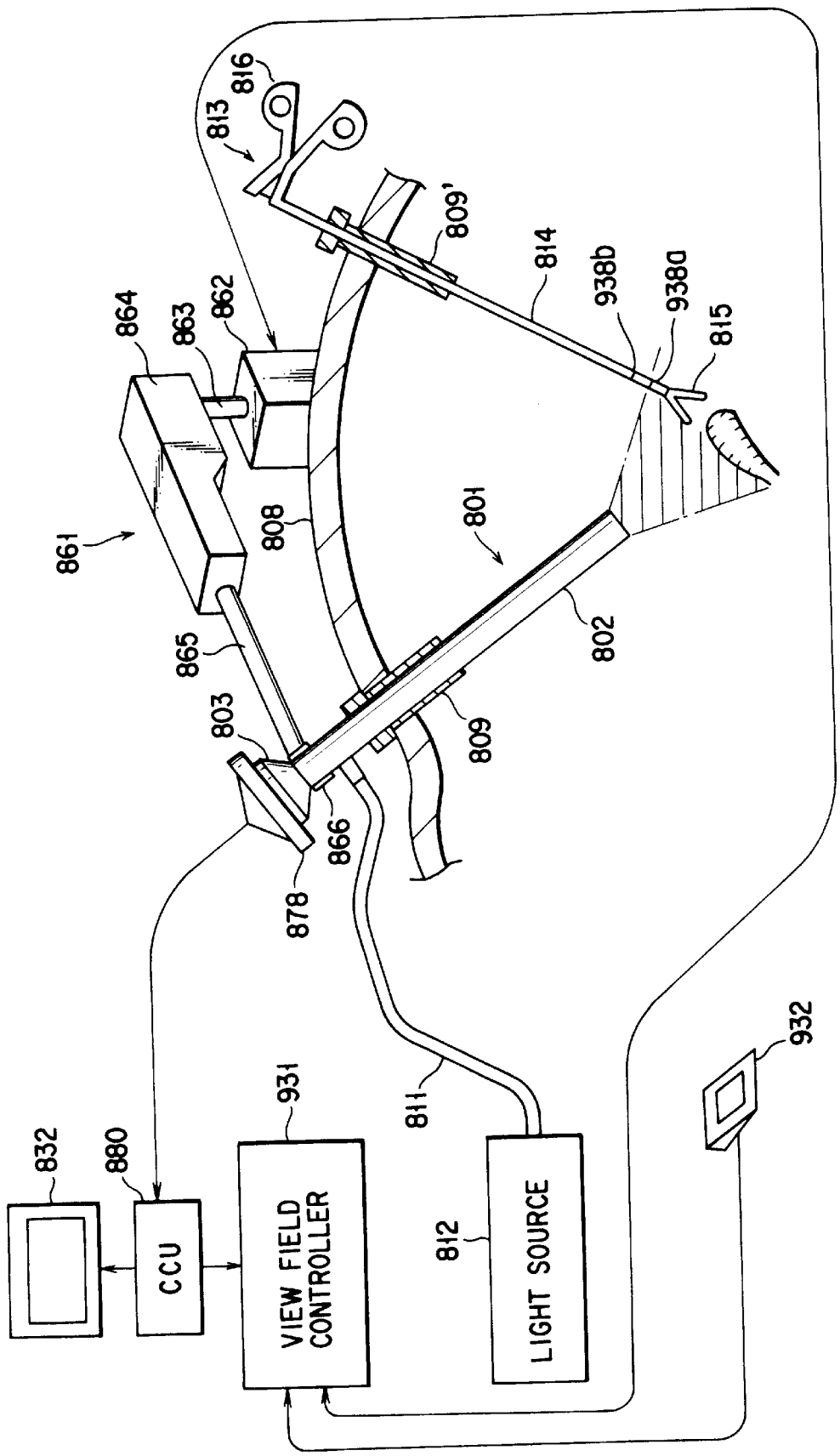
FIG. 64 is a diagram representing an endoscope surgery system according to a thirty-sixth embodiment of this invention.

As shown in FIG. 64, a foot switch 932 and an electric manipulator 861 are connected to the view filed controller 931. The manipulator 861 holds a rigid scope 801. As illustrated in FIG. 65, the view field controller 931 comprises a color-space converter 933, an extracted-image forming device 934, a gravity center calculator 935, a position-inferring device 936, and a position-designating device 937. It is the position-designating device 937 to which the foot switch 932 is connected.

As shown in FIG. 66, the insertion section 802 of the rigid scope 801 is inserted into the peritoneal cavity through the abdominal wall 808, and the insertion section 814 of a forceps 813 is inserted into the cavity through the abdominal wall 808. Two color markers 938a and 938b of different colors are provided on the distal end portion of the insertion section 814. Each of the markers is of a color quite different from those of the organs, such as green, yellow or the like. The markers 938a and 938b are spaced part for a distance A, and the marker 938a is located at a distance B from the tips of the tongs 815 attached to the distal end of the forceps 813.

FIG. 67 shows an image of the distal end portion of the forceps 813, including the tongs 815.

In operation, an optical image of the interior of the cavity is supplied from the rigid scope 801 to the CCD (not shown) provided in a TV camera adapter 878. The CCD generates a video signal from the optical image. The video signal is supplied via the CCU 880 to the view field controller 931.

In the view field controller 931, the color-space converter 933 and the extracted-image forming device 934 process the video signal. They designate the colors of the color markers 938a and 938b attached to the distal end of the forceps 813 as extracted colors, and output binary image data representing only the image of the distal end of the forceps 813.

In the view field controller 931, the video signal is input to the gravity center calculator 935. The view field controller 931 calculates the centers of the color markers 938a and 938b and generates signals representing the centers calculated. These signals are supplied to the position-inferring device 936. The device 936 infers the position of the distal end of the forceps 813 and produces the data representing this position. The data is supplied to the position-designating device 937. The device 937 finds the difference between the data representing the position of the distal end of the forceps 813 and the pixel data representing a designated position on the TV monitor screen, at which to display the distal end. The difference is the distance by which to move the image of the distal end to the designated position. The data representing the distance is supplied to the electric manipulator 861 when the surgeon turns on the foot switch 932.

How the position-inferring device 936 infers the position of the distal end of the forceps 813 will be explained.

The position of the distal end, $(x_0, y_0)$, can be calculated as follows:

$$(x_0, y_0) = (B/A^*(x_2-x_1)+x_2, B/A^*(y_2-y_1)+y_2) \quad (1)$$

where $(x_1, y_1)$ is the position of the color marker 938b, $(x_2, y_2)$ is the position of the color marker 938a, A is the distance between the color markers 938a and 938b, and B is the distance between the color marker 938a and the tips of the tongs 815.

The first color marker 938b may not be seen, concealed behind an organ or covered with body fluid. In this case, the position $(x_0, y_0)$ is inferred as follows:

$$(x_0, y_0) = (B/A^*(x_2'-x_1')+x_2, B/A^*(y_2'-y_1')+y_2) \quad (2)$$

where $(x_1', y_1')$ and $(x_2', y_2')$ are the positions the markers 938b and 939a assume immediately before the first marker 938b becomes invisible.

Further, the second color marker 938a may not be seen, hidden behind an organ or covered with body fluid. If this is the case, the position $(x_0, y_0)$ is inferred as follows:

$$(x_0, y_0) = ((B+A)/A^*(x_2'-x_1')+x_1, (B+A)/A^*(y_2'-y_1')+y_1) \quad (3)$$

where $(x_1', y_1')$ and $(x_2', y_2')$ are the positions the markers 938b and 939a assume immediately before the second marker 938b becomes invisible.

Three color markers, instead of two, may be provided on the distal end portion of the forceps 813, and the positions of two of three markers may be used to calculate the position of the distal end of the forceps 813. In addition, the foot switch 932 may be replaced by a hand switch which is attached to the handle 816 of the forceps 813.

Provided on the distal end portion of the forceps 813, not on the tongs 815, the color markers 938a and 938b remain visible on the screen of the TV monitor 832 during the endoscope surgery. Even if the tongs 815 are located behind an organ or a tissue and inevitably becomes invisible, the position of the distal end of the forceps 813 can be detected reliably.

Furthermore, even if the color marker 938a or 938b becomes invisible, hidden behind an organ or covered with body fluid, the present position of the distal end of the forceps 813 can be inferred from the positions which the markers 938b and 939a had assumed immediately before the second marker 938b became invisible. This enables the surgeon to switch the view field of the rigid scope 801, while performing the endoscope surgery.

In the thirty-sixth embodiment, the electric manipulator 861 holding the rigid scope 801 is used as means for switching the view field of the scope 801. Instead, an XY stage supporting an CCD may be incorporated in a magnifying optical system of the type employed in the first embodiment and may be moved to switch the view field of the scope 801.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An endoscope system comprising:

an endoscope;

a holder for holding said endoscope;

an image pickup section including an image pickup optical system for receiving an endoscopic image from said endoscope, a path branch for branching an optical path of said image pickup optical system into a first optical path and a second optical path, a wide angle image pickup element provided in the first optical path for forming a wide angle image from the endoscopic image, and a magnified image pickup element provided in the second optical path for forming a magnified image from the endoscopic image;

a display for displaying an image provided by said image pickup section;

an object identifier for identifying an object observed through said endoscope;

a position detector for detecting a position of the object from a wide angle image formed by said wide angle image pickup element of said image pickup section, and for generating position data representing the detected position; and a view field switching control mechanism for moving the magnified image formed by said magnified pickup element of said image pickup section in accordance with said position data, without moving said endoscope, to thereby switch a view field of said endoscope.

2. The system according to claim 1, wherein said view field switching control mechanism includes a switch for actuating a change of said view field.

3. The system according to claim 1, wherein said image pickup section includes a magnification controller for controlling one of said wide angle image pickup element and said magnified image pickup element to form an image in a desired magnification.

4. The system according to claim 1, further comprising an instrument insertable into the patient's body, and wherein said object identifier comprises a colored member provided on a distal end portion of said instrument, and said position detector comprises a color extractor for processing data representing the endoscopic image to thereby extract data representing a position of the colored member.

5. The system according to claim 1, further comprising an instrument insertable into the patient's body, and wherein said object identifier comprises an emphasized outline of a distal end portion of said instrument, and said position detector comprises a data processing circuit for processing data representing the endoscopic image to thereby extract data representing a position of the emphasized outline of the distal end of said instrument.

6. The system according to claim 1, wherein said view field switching control mechanism comprises an actuator for driving said magnified image pickup element, and a position designator for calculating a distance which the actuator is to be driven and for designating a position to which the actuator is to be driven.

7. The system according to claim 1, wherein said view field switching control mechanism comprises an actuator for driving a focusing lens provided in said magnified image pickup element, and a position designator for calculating a distance which the actuator is to be driven and for designating a position to which the actuator is to be driven.

* * * * *